United States Patent
Bloom et al.

(10) Patent No.: US 10,636,512 B2
(45) Date of Patent: Apr. 28, 2020

(54) IMMUNO-ONCOLOGY APPLICATIONS USING NEXT GENERATION SEQUENCING

(71) Applicant: CoFactor Genomics, Inc., St. Louis, MO (US)

(72) Inventors: Ryan J. Bloom, San Francisco, CA (US); Jon R. Armstrong, San Diego, CA (US)

(73) Assignee: COFACTOR GENOMICS, INC., St. Louis, MO (US)

( * ) Notice: Subject to any disclaimer, the term of this patent is extended or adjusted under 35 U.S.C. 154(b) by 0 days.

(21) Appl. No.: 16/056,406

(22) Filed: Aug. 6, 2018

(65) Prior Publication Data

US 2019/0018926 A1 Jan. 17, 2019

Related U.S. Application Data

(63) Continuation of application No. PCT/US2018/042176, filed on Jul. 13, 2018.

(60) Provisional application No. 62/532,921, filed on Jul. 14, 2017, provisional application No. 62/658,418, filed on Apr. 16, 2018.

(51) Int. Cl.
| | |
|---|---|
| G01N 33/48 | (2006.01) |
| G16B 30/00 | (2019.01) |
| G06K 9/62 | (2006.01) |
| G16B 20/00 | (2019.01) |
| G16B 25/00 | (2019.01) |
| G16B 40/00 | (2019.01) |
| G16B 25/10 | (2019.01) |
| G16B 20/20 | (2019.01) |
| G01N 33/574 | (2006.01) |
| G16B 5/00 | (2019.01) |

(52) U.S. Cl.
CPC ........... *G16B 30/00* (2019.02); *G06K 9/6229* (2013.01); *G06K 9/6243* (2013.01); *G16B 20/00* (2019.02); *G16B 20/20* (2019.02); *G16B 25/00* (2019.02); *G16B 25/10* (2019.02); *G16B 40/00* (2019.02); *G01N 33/574* (2013.01); *G01N 2800/52* (2013.01); *G16B 5/00* (2019.02)

(58) Field of Classification Search
None
See application file for complete search history.

(56) References Cited

U.S. PATENT DOCUMENTS

| | | | |
|---|---|---|---|
| 6,789,069 B1 | 9/2004 | Barnhill et al. | |
| 7,117,188 B2 | 10/2006 | Guyon et al. | |
| 7,308,364 B2 | 12/2007 | Shaughnessy et al. | |
| 7,371,736 B2 | 5/2008 | Shaughnessy et al. | |
| 7,475,048 B2 | 1/2009 | Weston et al. | |
| 7,771,932 B1 | 8/2010 | Groux et al. | |
| 7,970,718 B2 | 6/2011 | Weston et al. | |
| 8,043,815 B2 | 10/2011 | Li et al. | |
| 8,236,503 B2 | 8/2012 | Faham et al. | |
| 8,420,885 B2 | 4/2013 | Clarke et al. | |
| 8,481,271 B2 | 7/2013 | Galon et al. | |
| 8,580,497 B2 | 11/2013 | Stratton et al. | |
| 8,741,662 B2 | 6/2014 | Van Eyk et al. | |
| 8,759,006 B2 | 6/2014 | Reiter et al. | |
| 9,002,682 B2 | 4/2015 | Kasabov | |
| 9,279,159 B2 | 3/2016 | Robins et al. | |
| 9,291,625 B2 | 3/2016 | Semizarov et al. | |
| 9,340,830 B2 | 5/2016 | Downing et al. | |
| 9,551,034 B2 | 1/2017 | Cowens et al. | |
| 9,589,099 B2 | 3/2017 | Tang et al. | |
| 9,678,078 B2 | 6/2017 | Trieu | |
| 10,095,829 B2 | 10/2018 | Lazar et al. | |
| 10,282,588 B2 | 5/2019 | Comaniciu et al. | |
| 2003/0049635 A1 | 3/2003 | Sommer et al. | |
| 2004/0162679 A1 | 8/2004 | Li | |
| 2005/0048463 A1 | 3/2005 | Deng et al. | |
| 2006/0074824 A1 | 4/2006 | Li | |
| 2007/0065844 A1 | 3/2007 | Golub et al. | |
| 2007/0172844 A1 | 7/2007 | Lancaster et al. | |
| 2008/0312199 A1 | 12/2008 | Glinsky | |
| 2009/0171590 A1 | 7/2009 | Puskas et al. | |
| 2009/0186024 A1 | 7/2009 | Nevins et al. | |
| 2009/0215037 A1 | 8/2009 | Ma et al. | |
| 2010/0041048 A1 | 2/2010 | Diehl et al. | |
| 2010/0112628 A1 | 5/2010 | Gernez et al. | |
| 2010/0113299 A1 | 5/2010 | Von Hoff et al. | |

(Continued)

FOREIGN PATENT DOCUMENTS

| | | |
|---|---|---|
| CA | 2638844 C | 5/2016 |
| CN | 103608033 B | 6/2016 |

(Continued)

OTHER PUBLICATIONS

Lu, Peng, Aleksey Nakorchevskiy, and Edward M. Marcotte. "Expression deconvolution: a reinterpretation of DNA microarray data reveals dynamic changes in cell populations." Proceedings of the National Academy of Sciences 100.18 (2003): 10370-10375.*

(Continued)

*Primary Examiner* — Anna Skibinsky

(74) *Attorney, Agent, or Firm* — Wilson Sonsini Goodrich & Rosati

(57) ABSTRACT

Provided herein are systems and methods for generating an immune-oncology profile from a biological sample. The immune-oncology profile can include the proportion or percentage of immune cells, expression of immune escape genes, and/or mutational burden. The immune-oncology profile may allow the generation of classifiers for making prognostic or diagnostic predictions.

13 Claims, 17 Drawing Sheets

(56) References Cited

U.S. PATENT DOCUMENTS

| | | |
|---|---|---|
| 2010/0286232 A1 | 11/2010 | Schmittgen et al. |
| 2011/0288781 A1 | 11/2011 | Bevilacqua et al. |
| 2012/0004854 A1 | 1/2012 | Fernandez et al. |
| 2012/0115138 A1 | 5/2012 | Deigner et al. |
| 2013/0143222 A1 | 6/2013 | Ellsworth et al. |
| 2013/0190194 A1 | 7/2013 | Tang |
| 2014/0228233 A1* | 8/2014 | Pawlowski .......... C12Q 1/6886 506/9 |
| 2014/0330583 A1 | 11/2014 | Madhavan et al. |
| 2015/0065352 A1 | 3/2015 | Faham et al. |
| 2015/0072876 A1 | 3/2015 | Zuckerman et al. |
| 2015/0199477 A1 | 7/2015 | Kilpinen et al. |
| 2015/0292033 A1 | 10/2015 | Wang et al. |
| 2015/0294062 A1 | 10/2015 | Quon et al. |
| 2016/0002732 A1* | 1/2016 | Harkin ................. C12Q 1/6886 506/9 |
| 2016/0042120 A1 | 2/2016 | Danaher |
| 2016/0071432 A1 | 3/2016 | Kurowski et al. |
| 2016/0217253 A1 | 7/2016 | Newman et al. |
| 2016/0222118 A1 | 8/2016 | Chen et al. |
| 2016/0265050 A1 | 9/2016 | Sahin et al. |
| 2016/0299146 A1 | 10/2016 | Garraway et al. |
| 2016/0321561 A1 | 11/2016 | Röder et al. |
| 2017/0073774 A1 | 3/2017 | Lo et al. |
| 2017/0198039 A1 | 7/2017 | Wong |
| 2017/0211143 A1 | 7/2017 | Shendure et al. |
| 2017/0233808 A1 | 8/2017 | Haining et al. |
| 2017/0260585 A1 | 9/2017 | Lapointe et al. |
| 2017/0260590 A1 | 9/2017 | Eltoukhy et al. |
| 2017/0267977 A1 | 9/2017 | Huang et al. |
| 2017/0321285 A1 | 11/2017 | Kobayashi |
| 2017/0363626 A1 | 12/2017 | Johnson |
| 2018/0020918 A1 | 1/2018 | Redei |
| 2018/0032665 A1 | 2/2018 | Tang et al. |
| 2018/0253591 A1 | 9/2018 | Madabhushi et al. |
| 2019/0134174 A1* | 5/2019 | Jones .............. A61K 39/001106 |
| 2019/0338369 A1* | 11/2019 | Van Allen .......... C07K 16/2818 |

FOREIGN PATENT DOCUMENTS

| | | |
|---|---|---|
| DK | 3002337 T3 | 2/2019 |
| EP | 1356289 A2 | 10/2003 |
| EP | 1511855 A4 | 2/2006 |
| EP | 1012240 B1 | 3/2008 |
| EP | 2577535 A2 | 4/2013 |
| EP | 2183393 B1 | 6/2014 |
| EP | 2389453 B1 | 11/2015 |
| EP | 2856153 B1 | 1/2018 |
| JP | 2013146278 A | 8/2013 |
| KR | 20130105296 A | 9/2013 |
| KR | 101540647 B1 | 8/2015 |
| WO | WO-02074918 A2 | 9/2002 |
| WO | WO-02066684 A3 | 10/2003 |
| WO | WO-2006094836 A2 | 9/2006 |
| WO | WO-2007106507 A2 | 9/2007 |
| WO | WO-2008121866 A2 | 10/2008 |
| WO | WO-2009152437 A2 | 12/2009 |
| WO | WO-2013188860 A1 | 12/2013 |
| WO | WO-2013192570 A1 | 12/2013 |
| WO | WO-2014092457 A1 | 6/2014 |
| WO | WO-2014179357 A1 | 11/2014 |
| WO | WO-2014184744 A1 | 11/2014 |
| WO | WO-2016197131 A1 | 12/2016 |
| WO | WO-2017055319 A1 | 4/2017 |
| WO | WO-2018165103 A1 | 9/2018 |
| WO | WO-2019084559 A1 | 5/2019 |

OTHER PUBLICATIONS

Geladi, Paul, and Bruce R. Kowalski. "Partial least-squares regression: a tutorial." Analytica chimica acta 185 (1986): 1-17.*

Arreola, Rodrigo, et al. "Immunomodulatory effects mediated by serotonin." Journal of immunology research 2015 (2015). pp. 1-21.*

Newman, et al. Robust enumeration of cell subsets from tissue expression profiles. Nat Methods. May 2015; 12(5): 453-457. Published online Mar. 30, 2015. doi: 10.1038/nmeth.3337.

Racle, et al. Simultaneous enumeration of cancer and immune cell types from bulk tumor gene expression data. eLife. 2017; 6: e26476. Published online Nov. 13, 2017. doi: 10.7554/eLife.26476.

Jamieson, et al.: Gene-Expression Profiling to Predict Responsiveness to Immunotherapy. Cancer Gene Therapy. 24(3): 134-140 (2016).

Mohammadi, et al.: A Critical Survey of Deconvolution Methods for Separating Cell Types in Complex Tissues. Proceedings of the IEEE. 105(2): 340-366 (2017).

PCT/US2018/042176 International Search Report and Written Opinion dated Nov. 7, 2018.

Rognerud, J. J.: Bioinformatics Approaches to Deconvolute Phenotype-Specific Immune Cells from Complex Tissue. Master's Thesis, University of Oslo, Department of Informatics. 1-104 (2016).

\* cited by examiner

IMMUNO-ONCOLOGY APPLICATIONS USING NEXT GENERATION SEQUENCING

CROSS-REFERENCE

This application is a continuation of International Application No. PCT/US2018/042176, filed Jul. 13, 2018, which claims the benefit of U.S. Provisional Patent Application No. 62/532,921, filed Jul. 14, 2017, and U.S. Provisional Patent Application No. 62/658,418, filed Apr. 16, 2018, each of which is entirely incorporated herein by reference.

BACKGROUND

Cancer is a complex group of diseases involving abnormal cell growth with the potential to invade or spread to other parts of the body. Millions of new cases of cancer occur globally each year. Understanding the immune and tumor profile may help with diagnosis and treatment.

SUMMARY

In an aspect, disclosed herein are methods for generating an immune-oncology profile using ribonucleic acid (RNA) sequencing data, comprising: (a) obtaining RNA sequencing data from a sample obtained from a subject; (b) evaluating at least a subset of the RNA sequencing data to determine level of gene expression for at least one immune modulatory gene; (c) analyzing at least a subset of the RNA sequencing data to calculate a mutational burden based on a plurality of genes from Table 5; (d) applying a deconvolution algorithm to at least a subset of the RNA sequencing data to identify and quantify one or more cell types that are present in the sample based on a plurality of expression signature genes from Tables 1A-1E; and (e) generating an immune-oncology profile based on the level of gene expression determined in (b), the mutational burden calculated in (c), and the one or more cell types quantified in (d). In some instances, the plurality of expression signature genes comprises at least one gene from each of Tables 1A, 1B, 1C, 1D, and 1E. In some instances, the plurality of expression signature genes comprises at least 10, 20, 30, 40, 50, 60, 70, 80, 90, or 100 genes from Table 2, 3, or 4. In some instances, the immune-oncology profile comprises a predicted response to a therapeutic intervention. In some instances, the predicted response is a positive response or a negative response to the therapeutic intervention. In some instances, the positive response comprises tumor regression, slowing tumor progression, or halt of tumor progression. In some instances, the negative response comprises tumor progression, lack of response to the therapeutic intervention, or a combination thereof. In some instances, the therapeutic intervention comprises an immune-therapy. In some instances, the therapeutic intervention further comprises radiation, chemotherapy, surgery, or a combination thereof. In some instances, the method further comprises providing a recommendation based on the immune-oncology profile. In some instances, the recommendation is to start, stop, change, or continue a therapeutic intervention. In some instances, the method further comprises using the profile to provide a therapeutic intervention to the subject. In some instances, the therapeutic intervention is an active immunotherapy, a passive immunotherapy, or a combination thereof. In some instances, the therapeutic intervention is a cancer vaccine, cytokine therapy, immune cell therapy, antibody therapy, or a combination thereof. In some instances, the antibody therapy comprises introducing tumor-targeting monoclonal antibodies, immune cell activating antibodies, or a combination thereof. In some instances, the immune-oncology profile comprises a predicted level of resistance to one or more therapeutic agents based on one or more cancer gene expression signatures identified in (d). In some instances, in (c), the deconvolution algorithm applies a deconvolution matrix to the RNA sequencing data to quantify the one or more cell types that are present in the sample. In some instances, the deconvolution matrix comprises a plurality of immune cell expression signature genes. In some instances, the deconvolution matrix comprises a plurality of tumor cell expression signature genes. In some instances, the deconvolution matrix comprises a plurality of cell types, each cell type comprising a plurality of expression signature genes, wherein expression counts for each expression signature gene is normalized across the plurality of cell types. In some instances, the deconvolution algorithm identifies and quantifies the one or more cell types that are present in the sample using linear least-squares regression (LLSR), quadratic programming (QP), perturbation model for gene expression deconvolution (PERT), robust linear regression (RLR), microarray microdissection with analysis of differences (MMAD), digital sorting algorithm (DSA), or support vector regression. In some instances, in (c) the mutational burden is calculated across at least 500 genes. In some instances, in (c) the mutational burden is calculated across at least 1000 genes. In some instances, in (c) the mutational burden is calculated across at least 2000 genes. In some instances, in (c) the plurality of genes includes at least 500 genes. In some instances, in (c) the plurality of genes includes at least 1000 genes. In some instances, in (d) the plurality of expression signature genes includes at least 100 cell expression signature genes. In some instances, in (d) the plurality of expression signature genes includes at least 200 cell expression signature genes. In some instances, in (d) the plurality of expression signature genes includes genes having a bimodal expression signature between at least two cell types with no more than a 50% overlap between modes. In some instances, in (d) the deconvolution algorithm requires no more than 200 cell expression signature genes to identify and quantify the one or more cell types with at least 90% accuracy for 100 independent samples. In some instances, in (d) the one or more cell types includes at least one leukocyte cell type, stromal cell type, tumor cell type, or a combination thereof. In some instances, in (d) the one or more cell types comprise at least 10 leukocyte types. In some instances, in (d) the one or more cell types comprise at least 20 leukocyte types. In some instances, in (d) the one or more cell types comprise at least 1 tumor cell type. In some instances, (a) comprises obtaining RNA molecules from the sample and measuring the level of gene expression on the RNA molecules. In some instances, (a) comprises obtaining RNA molecules from the sample and performing reverse transcription polymerase chain reaction on the RNA molecules to generate complementary deoxyribonucleic acid (cDNA) molecules, and sequencing the cDNA molecules. In some instances, the cDNA molecules are tagged with unique molecular identifiers and amplified by polymerase chain reaction prior to sequencing. In some instances, (a) comprises performing next generation RNA sequencing on a cDNA library generated from the sample. In some instances, the at least one immune modulatory molecule is CTLA-4, PD-L1, LAG-3, KIR, TIM-3, CECAM1, VISTA, TIGIT, CD73, or a combination thereof. In some instances, the sample is a tumor biopsy. In some instances, the sample is at least one formalin-fixed paraffin-embedded (FFPE) curl. In some instances, the sample has an RNA integrity number (RIN) of no more than 6.0. In some instances, the sample has an RNA integrity number (RIN) of no more than 2.0. In some instances, the sample comprises RNA molecules at least 200 nucleotides in size that constitute no more than 90% of total RNA in the sample. In some instances, the sample comprises RNA molecules at least 200 nucleotides in size that constitute no more than 60% of total RNA in the sample. In some instances, the sample comprises RNA molecules at least 200 nucleotides in size that constitute no more than 30% of total RNA in the sample. In some instances, the sample is obtained from skin, blood, brain, bladder, bone, bone marrow, breast, colon, stomach, esophagus, ovary, uterus, gallbladder, fallopian tube, testicle, kidney, liver, pancreas, adrenal gland, cervix, endometrium, head or neck, lung, prostate, thymus, thyroid, lymph node, or urinary bladder. In some instances, the subject has cancer. In some instances, the method further comprises presenting the immune-oncology profile as a report with graphical elements representing the level of gene expression determined in (b), the mutational burden calculated in (c), and the one or more cell types identified and quantified in (d). In some instances, the level of gene expression determined in (b) is displayed on the report in combination with a reference expression level. In some instances, the mutational burden calculated in (c) is displayed along a single axis having a range between low and high mutational burden. In some instances, the one or more cell types identified and quantified in (d) are displayed in a pie chart indicating a percentage of each cell type in the sample.

In another aspect, disclosed herein are methods for recommending a therapeutic intervention using ribonucleic acid (RNA) sequencing data, comprising: (a) obtaining RNA sequencing data from a sample obtained from a subject; (b) evaluating at least a subset of the RNA sequencing data to determine level of gene expression for at least one immune modulatory gene; (c) analyzing at least a subset of the RNA sequencing data to calculate a mutational burden based on a plurality of genes from Table 5; (d) applying a deconvolution algorithm to at least a subset of the RNA sequencing data to identify and quantify one or more cell types that are present in the sample based on a plurality of expression signature genes from Tables 1A-1E; (e) generating an immune-oncology profile based on the level of gene expression determined in (b), the mutational burden calculated in (c), and the one or more cell types quantified in (d); and (f) recommending a therapeutic intervention based on the immune-oncology profile.

In another aspect, disclosed herein are methods for predicting a clinical outcome using ribonucleic acid (RNA) sequencing data, comprising: (a) obtaining RNA sequencing data from a sample obtained from a subject; (b) evaluating at least a subset of the RNA sequencing data to determine level of gene expression for at least one immune modulatory gene; (c) analyzing at least a subset of the RNA sequencing data to calculate a mutational burden based on a plurality of genes from Table 5; (d) applying a deconvolution algorithm to at least a subset of the RNA sequencing data to identify and quantify one or more cell types that are present in the sample based on a plurality of expression signature genes from Tables 1A-1E; (e) generating an immune-oncology profile based on the level of gene expression determined in (b), the mutational burden calculated in (c), and the one or more cell types quantified in (d); and (f) making a prediction of a clinical outcome to a therapeutic intervention based on the immune-oncology profile, the prediction having a positive predictive value of at least 90% for at least 100 independent samples.

In another aspect, disclosed herein are methods for providing a therapeutic intervention based on ribonucleic acid (RNA) sequencing data, comprising: (a) obtaining RNA sequencing data from a sample obtained from a subject; (b) evaluating at least a subset of the RNA sequencing data to determine level of gene expression for at least one immune modulatory gene; (c) analyzing at least a subset of the RNA sequencing data to calculate a mutational burden based on a plurality of genes from Table 5; (d) applying a deconvolution algorithm to at least a subset of the RNA sequencing data to identify and quantify one or more cell types that are present in the sample based on a plurality of expression signature genes from Tables 1A-1E; (e) generating an immune-oncology profile based on the level of gene expression determined in (b), the mutational burden calculated in (c), and the one or more cell types quantified in (d); and (f) providing a therapeutic intervention based on the immune-oncology profile.

In another aspect, disclosed herein are systems for generating an immune-oncology profile using ribonucleic acid (RNA) sequencing data, comprising: a database comprising the RNA sequencing data from a sample obtained from a subject; and one or more computer processors that are coupled to the database, wherein the one or more computer processors are individually or collectively programmed to: (a) evaluate at least a subset of the RNA sequencing data to determine level of gene expression for at least one immune modulatory gene; (b) analyze at least a subset of the RNA sequencing data to calculate a mutational burden based on a plurality of genes from Table 5; (c) apply a deconvolution algorithm to at least a subset of the RNA sequencing data to identify and quantify one or more cell types that are present in the sample based on a plurality of expression signature genes from Tables 1A-1E; and (d) generate an immune-oncology profile based on the level of gene expression determined in (a), the mutational burden calculated in (b), and the one or more cell types quantified in (c). In some instances, the plurality of expression signature genes comprises at least one gene from each of Tables 1A, 1B, 1C, 1D, and 1E. In some instances, the plurality of expression signature genes comprises at least 10, 20, 30, 40, 50, 60, 70, 80, 90, or 100 genes from Table 2, 3, or 4. In some instances, the immune-oncology profile comprises a predicted response to a therapeutic intervention. In some instances, the predicted response is a positive response or a negative response to the therapeutic intervention. In some instances, the positive response comprises tumor regression, slowing tumor progression, or halt of tumor progression. In some instances, the negative response comprises tumor progression, lack of response to the therapeutic intervention, or a combination thereof. In some instances, the therapeutic intervention comprises an immune-therapy. In some instances, the therapeutic intervention further comprises radiation, chemotherapy, surgery, or a combination thereof. In some instances, the one or more computer processors are programmed to provide a recommendation based on the immune-oncology profile. In some instances, the recommendation is to start, stop, change, or continue a therapeutic intervention. In some instances, the profile is used to provide a therapeutic intervention to the subject. In some instances, the therapeutic intervention is an active immunotherapy, a passive immunotherapy, or a combination thereof. In some instances, the therapeutic intervention is a cancer vaccine, cytokine therapy, immune cell therapy, antibody therapy, or a combination thereof. In some instances, the antibody therapy comprises introducing tumor-targeting monoclonal antibodies, immune cell activating antibodies, or a combination thereof. In some instances, the immune-oncology profile comprises a predicted level of resistance to one or more therapeutic agents based on one or more cancer gene expression signatures identified in (d). In some instances, in (c), the deconvolution algorithm applies a deconvolution matrix to the RNA sequencing data to quantify the one or more cell types that are present in the sample. In some instances, the deconvolution matrix comprises a plurality of immune cell expression signature genes. In some instances, the deconvolution matrix comprises a plurality of tumor cell expression signature genes. In some instances, the deconvolution matrix comprises a plurality of cell types, each cell type comprising a plurality of expression signature genes, wherein expression counts for each expression signature gene is normalized across the plurality of cell types. In some instances, the deconvolution algorithm identifies and quantifies the one or more cell types that are present in the sample using linear least-squares regression (LLSR), quadratic programming (QP), perturbation model for gene expression deconvolution (PERT), robust linear regression (RLR), microarray microdissection with analysis of differences (MMAD), digital sorting algorithm (DSA), or support vector regression (SVR). In some instances, in (c), the mutational burden is calculated across at least 500 genes. In some instances, in (c), the mutational burden is calculated across at least 1000 genes. In some instances, in (c), the mutational burden is calculated across at least 2000 genes. In some instances, in (c) the plurality of genes includes at least 500 genes. In some instances, in (c) the plurality of genes includes at least 1000 genes. In some instances, in (d) the plurality of expression signature genes includes at least 100 cell expression signature genes. In some instances, in (d) the plurality of expression signature genes includes at least 200 cell expression signature genes. In some instances, in (d) the plurality of expression signature genes includes genes having a bimodal expression signature between at least two cell types with no more than a 50% overlap between modes. In some instances, in (d) the deconvolution algorithm requires no more than 200 cell expression signature genes to identify and quantify the one or more cell types with at least 90% accuracy for at least 100 independent samples. In some instances, in (d) the one or more cell types includes at least one leukocyte cell type, stromal cell type, tumor cell type, or a combination thereof. In some instances, in (d) the one or more cell types comprise at least 10 leukocyte types. In some instances, in (d) the one or more cell types comprise at least 20 leukocyte types. In some instances, in (d) the one or more cell types comprise at least 1 tumor cell type. In some instances, (a) comprises obtaining RNA molecules from the sample and measuring the level of gene expression on the RNA molecules. In some instances, (a) comprises obtaining RNA molecules from the sample and performing reverse transcription polymerase chain reaction on the RNA molecules to generate complementary deoxyribonucleic acid (cDNA) molecules, and sequencing the cDNA molecules. In some instances, the cDNA molecules are tagged with unique molecular identifiers and amplified by polymerase chain reaction prior to sequencing. In some instances, (a) comprises performing next generation RNA sequencing on a cDNA library generated from the sample. In some instances, the at least one immune modulatory molecule is CTLA-4, PD-L1, LAG-3, KIR, TIM-3, CECAM1, VISTA, TIGIT, CD73, or a combination thereof. In some instances, the sample is a tumor biopsy. In some instances, the sample is at least one formalin-fixed paraffin-embedded (FFPE) curl. In some instances, the sample has an RNA integrity number (RIN) of no more than 6.0. In some instances, the sample has an RNA integrity number (RIN) of no more than 2.0. In some instances, the sample comprises RNA molecules at least 200 nucleotides in size that constitute no more than 90% of total RNA in the sample. In some instances, the sample comprises RNA molecules at least 200 nucleotides in size that constitute no more than 60% of total RNA in the sample. In some instances, the sample comprises RNA molecules at least 200 nucleotides in size that constitute no more than 30% of total RNA in the sample. In some instances, the sample is obtained from skin, blood, brain, bladder, bone, bone marrow, breast, colon, stomach, esophagus, ovary, uterus, gallbladder, fallopian tube, testicle, kidney, liver, pancreas, adrenal gland, cervix, endometrium, head or neck, lung, prostate, thymus, thyroid, lymph node, or urinary bladder. In some instances, the subject has cancer. In some instances, the immune-oncology profile is presented as a report with graphical elements representing the level of gene expression determined in (b), the mutational burden calculated in (c), and the one or more cell types quantified in (d). In some instances, the level of gene expression determined in (b) is displayed on the report in combination with a reference expression level. In some instances, the mutational burden calculated in (c) is displayed along a single axis having a range between low and high mutational burden. In some instances, the one or more cell types identified and quantified in (d) are displayed in a pie chart indicating a percentage of each cell type in the sample.

In another aspect, disclosed herein are systems for recommending a therapeutic intervention using ribonucleic acid (RNA) sequencing data, comprising: a database comprising the RNA sequencing data from a sample obtained from a subject; and one or more computer processors that are coupled to the database, wherein the one or more computer processors are individually or collectively programmed to: (a) evaluate at least a subset of the RNA sequencing data to determine level of gene expression for at least one immune modulatory gene; (b) analyze at least a subset of the RNA sequencing data to calculate a mutational burden based on a plurality of genes from Table 5; (c) apply a deconvolution algorithm to at least a subset of the RNA sequencing data to identify and quantify one or more cell types that are present in the sample based on a plurality of expression signature genes from Tables 1A-1E; (d) generate an immune-oncology profile based on the level of gene expression determined in (a), the mutational burden calculated in (b), and the one or more cell types quantified in (c); and (e) recommend a therapeutic intervention based on the immune-oncology profile.

In another aspect, disclosed herein are systems for predicting a clinical outcome using ribonucleic acid (RNA) sequencing data, comprising: a database comprising the RNA sequencing data from a sample obtained from a subject; and one or more computer processors that are coupled to the database, wherein the one or more computer processors are individually or collectively programmed to: (a) evaluate at least a subset of the RNA sequencing data to determine level of gene expression for at least one immune modulatory gene; (b) analyze at least a subset of the RNA sequencing data to calculate a mutational burden based on a plurality of genes from Table 5; (c) apply a deconvolution algorithm to at least a subset of the RNA sequencing data to identify and quantify one or more cell types that are present in the sample based on a plurality of expression signature genes from Tables 1A-1E; (d) generate an immune-oncology profile based on the level of gene expression determined in (a), the mutational burden calculated in (b), and the one or more cell types quantified in (c); and (e) make a prediction of a clinical outcome to a therapeutic intervention based on the immune-oncology profile, the prediction having a positive predictive value of at least 90% for at least 100 independent samples.

In another aspect, disclosed herein are methods of analyzing ribonucleic acid (RNA) sequencing data, the method comprising: (a) obtaining a library comprising a plurality of RNA molecules from a sample of a subject; (b) contacting the library with a bait set configured to enrich for RNA molecules corresponding to target genes, the target genes comprising a plurality of genes selected from Tables 1A-1E and Table 5; (c) performing RNA sequencing on the target genes to generate RNA sequencing data; and (d) analyzing the RNA sequencing data to generate an immune-oncology profile comprising: gene expression for at least one immune modulatory gene, mutational burden, and cell type quantification. In some instances, the immune-oncology profile comprises a predicted response to a therapeutic intervention. In some instances, the predicted response is a positive response or a negative response to the therapeutic intervention. In some instances, the positive response comprises tumor regression, slowing tumor progression, or halt of tumor progression. In some instances, the negative response comprises tumor progression, lack of response to the therapeutic intervention, or a combination thereof. In some instances, the therapeutic intervention comprises an immune-therapy. In some instances, the therapeutic intervention further comprises radiation, chemotherapy, surgery, or a combination thereof. In some instances, the methods further comprise providing a recommendation based on the immune-oncology profile. In some instances, the recommendation is to start, stop, change, or continue a therapeutic intervention. In some instances, the methods further comprise using the profile to provide a therapeutic intervention to the subject. In some instances, the therapeutic intervention is an active immunotherapy, a passive immunotherapy, or a combination thereof. In some instances, the therapeutic intervention is a cancer vaccine, cytokine therapy, immune cell therapy, antibody therapy, or a combination thereof. In some instances, the antibody therapy comprises introducing tumor-targeting monoclonal antibodies, immune cell activating antibodies, or a combination thereof. In some instances, the immune-oncology profile comprises a predicted level of resistance to one or more therapeutic agents based on one or more cancer gene expression signatures identified in (d). In some instances, in (d), a deconvolution algorithm applies a deconvolution matrix to the RNA sequencing data to quantify one or more cell types that are present in the sample. In some instances, the deconvolution matrix comprises a plurality of immune cell expression signature genes. In some instances, the deconvolution matrix comprises a plurality of tumor cell expression signature genes. In some instances, the deconvolution matrix comprises a plurality of cell types, each cell type comprising a plurality of expression signature genes, wherein expression counts each expression signature gene is normalized across the plurality of cell types. In some instances, the deconvolution algorithm identifies and quantifies the one or more cell types that are present in the sample using linear least-squares regression (LLSR), quadratic programming (QP), perturbation model for gene expression deconvolution (PERT), robust linear regression (RLR), microarray microdissection with analysis of differences (MMAD), digital sorting algorithm (DSA), or support vector regression. In some instances, the plurality of expression signature genes includes at least 200 cell expression signature genes. In some instances, the plurality of expression signature genes includes genes having a bimodal expression signature between at least two cell types with no more than a 50% overlap between modes. In some instances, the deconvolution algorithm requires no more than 200 cell expression signature genes to identify and quantify the one or more cell types with at least 90% accuracy for 100 independent samples. In some instances, the one or more cell types include at least one leukocyte cell type, stromal cell type, tumor cell type, or a combination thereof. In some instances, the one or more cell types comprise at least 10 leukocyte types. In some instances, the one or more cell types comprise at least 20 leukocyte types. In some instances, the one or more cell types comprise at least 1 tumor cell type. In some instances, in (d), the mutational burden is calculated across at least 500 genes. In some instances, in (d), the mutational burden is calculated across at least 1000 genes. In some instances, in (d), the mutational burden is calculated across at least 2000 genes. In some instances, in (d) the plurality of genes includes at least 500 genes. In some instances, in (d) the plurality of genes includes at least 1000 genes. In some instances, in (d) the plurality of expression signature genes includes at least 100 cell expression signature genes. In some instances, (c) comprises measuring level of gene expression for the target genes. In some instances, (a) comprises obtaining RNA molecules from the sample and performing reverse transcription polymerase chain reaction on the RNA molecules to generate complementary deoxyribonucleic acid (cDNA) molecules, and sequencing the cDNA molecules. In some instances, the at least one immune modulatory molecule is CTLA-4, PD-L1, LAG-3, KIR, TIM-3, CECAM1, VISTA, TIGIT, CD73, or a combination thereof. In some instances, the sample is a tumor biopsy. In some instances, the sample is at least one formalin-fixed paraffin-embedded (FFPE) curl. In some instances, the sample has an RNA integrity number (RIN) of no more than 6.0. In some instances, the sample has an RNA integrity number (RIN) of no more than 2.0. In some instances, the sample comprises RNA molecules at least 200 nucleotides in size that constitute no more than 90% of total RNA in the sample. In some instances, the sample comprises RNA molecules at least 200 nucleotides in size that constitute no more than 60% of total RNA in the sample. In some instances, the sample comprises RNA molecules at least 200 nucleotides in size that constitute no more than 30% of total RNA in the sample. In some instances, the sample is obtained from skin, blood, brain, bladder, bone, bone marrow, breast, colon, stomach, esophagus, ovary, uterus, gallbladder, fallopian tube, testicle, kidney, liver, pancreas, adrenal gland, cervix, endometrium, head or neck, lung, prostate, thymus, thyroid, lymph node, or urinary bladder. In some instances, the subject has cancer. In some instances, the methods further comprise presenting the immune-oncology profile as a report with graphical elements representing the level of gene expression determined in (b), the mutational burden calculated in (c), and the one or more cell types quantified in (d). In some instances, the level of gene expression determined in (b) is displayed on the report in combination with a reference expression level. In some instances, the mutational burden calculated in (c) is displayed along a single axis having a range between low and high mutational burden. In some instances, the one or more cell types identified and quantified in (d) are displayed in a pie chart indicating a percentage of each cell type in the sample.

In another aspect, disclosed herein are methods of analyzing a data set comprising information from a plurality of components from a single source, the method comprising: (a) obtaining the data set, the data set comprising sequence and quantity information for a plurality of data members across the plurality of components; (b) evaluating at least a subset of the data set to determine a numerical quantifier for at least one data member; (c) analyzing at least a subset of the data set to calculate a variation indicator based on the sequence information; (d) applying a deconvolution algorithm to at least a subset of the data set to identify and quantify one or more components that constitute the plurality of components based on a plurality of data member signatures; and (e) generating an output profile based on the numerical quantifier determined in (b), the variation indicator calculated in (c), and the one or more components identified and quantified in (d). In some instances, the output profile comprises a predicted response to a procedure. In some instances, the predicted response is a positive response or a negative response to the procedure. In some instances, the methods further comprise providing a recommendation based on the output profile. In some instances, the recommendation is to start, stop, change, or continue a procedure. In some instances, the methods further comprise using the profile to provide a procedure. In some instances, in (d), the deconvolution algorithm applies a deconvolution matrix to the subset of the data set to identify and quantify the one or more components that constitute the plurality of components. In some instances, the deconvolution matrix comprises a plurality of data member signatures for a plurality of components. In some instances, the deconvolution matrix comprises a plurality of components, each component comprising a plurality of data member signatures, wherein each data member signature is normalized across the plurality of components. In some instances, the deconvolution algorithm identifies and quantifies the plurality of components using linear least-squares regression (LLSR), quadratic programming (QP), perturbation model for gene expression deconvolution (PERT), robust linear regression (RLR), microarray microdissection with analysis of differences (MMAD), digital sorting algorithm (DSA), or support vector regression. In some instances, in (d), the variation indicator is calculated across at least 500 data members. In some instances, in (d), the variation indicator is calculated across at least 1000 data members. In some instances, in (d), the variation indicator is calculated across at least 2000 data members. In some instances, in (d) the plurality of data members includes at least 500 data members. In some instances, in (d) the plurality of data members includes at least 1000 data members. In some instances, in (d) the plurality of data member signatures includes at least 100 data member signatures. In some instances, the plurality of data member signatures includes at least 200 data member signatures. In some instances, the plurality of data member signatures includes data member signatures having a bimodal expression signature between at least two components with no more than a 50% overlap between modes. In some instances, the deconvolution algorithm requires no more than 200 data member signatures to identify and quantify the one or more components with at least 90% accuracy for 100 independent data sets. In some instances, the methods further comprise presenting the output profile as a report with graphical elements representing the numerical quantifier for at least one data member determined in (b), the variation indicator calculated in (c), and the one or more components identified and quantified in (d). In some instances, numerical quantifier for at least one data member determined in (b) is displayed on the report in combination with a reference numerical quantifier. In some instances, the variation indicator calculated in (c) is displayed along a single axis having a range between low and high variation. In some instances, the one or more components identified and quantified in (d) are displayed in a pie chart indicating a percentage of each component.

In another aspect, disclosed herein are methods of making a recommendation based on a data set comprising information from a plurality of components from a single source, the method comprising: (a) obtaining the data set, the data set comprising sequence and quantity information for a plurality of data members across the plurality of components; (b) evaluating at least a subset of the data set to determine a numerical quantifier for at least one data member; (c) analyzing at least a subset of the data set to calculate a variation indicator based on the sequence information; (d) applying a deconvolution algorithm to at least a subset of the data set to identify and quantify one or more components that constitute the plurality of components based on a plurality of data member signatures; (e) generating an output profile based on the numerical quantifier determined in (b), the variation indicator calculated in (c), and the one or more components identified and quantified in (d); and (f) recommending a procedure based on the output profile.

In another aspect, disclosed herein are methods of making a recommendation based on a data set comprising information from a plurality of components from a single source, the method comprising: (a) obtaining the data set, the data set comprising sequence and quantity information for a plurality of data members across the plurality of components; (b) evaluating at least a subset of the data set to determine a numerical quantifier for at least one data member; (c) analyzing at least a subset of the data set to calculate a variation indicator based on the sequence information; (d) applying a deconvolution algorithm to at least a subset of the data set to identify and quantify one or more components that constitute the plurality of components based on a plurality of data member signatures; (e) generating an output profile based on the numerical quantifier determined in (b), the variation indicator calculated in (c), and the one or more components identified and quantified in (d); and (f) making a prediction of an outcome to a procedure based on the output profile, the prediction having a positive predictive value of at least 90% for at least 100 independent data sets.

In another aspect, disclosed herein are systems for analyzing a data set comprising information from a plurality of components from a single source, comprising: a database comprising the data set; and one or more computer processors that are coupled to the database, wherein the one or more computer processors are individually or collectively programmed to: (a) obtain the data set, the data set comprising sequence and quantity information for a plurality of data members across the plurality of components; (b) evaluate at least a subset of the data set to determine a numerical quantifier for at least one data member; (c) analyze at least a subset of the data set to calculate a variation indicator based on the sequence information; (d) apply a deconvolution algorithm to at least a subset of the data set to identify and quantify one or more components that constitute the plurality of components based on a plurality of data member signatures; and (e) generate an output profile based on the numerical quantifier determined in (b), the variation indicator calculated in (c), and the one or more components identified and quantified in (d). In some instances, the output profile comprises a predicted response to a procedure. In some instances, the predicted response is a positive response or a negative response to the procedure. In some instances, the output profile is used to provide a recommendation. In some instances, the recommendation is to start, stop, change, or continue a procedure. In some instances, the output profile is used to provide a procedure. In some instances, in (d), the deconvolution algorithm applies a deconvolution matrix to the subset of the data set to identify and quantify the one or more components that constitute the plurality of components. In some instances, the deconvolution matrix comprises a plurality of data member signatures for a plurality of components. In some instances, the deconvolution matrix comprises a plurality of component signatures, each component signature comprising a plurality of data member signatures, wherein each data member signature is normalized across the plurality of component signatures. In some instances, the deconvolution algorithm identifies and quantifies the plurality of components using linear least-squares regression (LLSR), quadratic programming (QP), perturbation model for gene expression deconvolution (PERT), robust linear regression (RLR), microarray microdissection with analysis of differences (MMAD), digital sorting algorithm (DSA), or support vector regression. In some instances, in (d), the variation indicator is calculated across at least 500 data members. In some instances, in (d), the variation indicator is calculated across at least 1000 data members. In some instances, in (d), the variation indicator is calculated across at least 2000 data members. In some instances, in (d) the plurality of data members includes at least 500 data members. In some instances, in (d) the plurality of data members includes at least 1000 data members. In some instances, in (d) the plurality of data member signatures includes at least 100 data member signatures. In some instances, the plurality of data member signatures includes at least 200 data member signatures. In some instances, the plurality of data member signatures includes data member signatures having a bimodal expression signature between at least two component signatures with no more than a 50% overlap between modes. In some instances, the deconvolution algorithm requires no more than 200 data member signatures to identify and quantify the one or more components with at least 90% accuracy for 100 independent data sets. In some instances, the output profile is presented as a report with graphical elements representing the numerical quantifier for at least one data member determined in (b), the variation indicator calculated in (c), and the one or more components identified and quantified in (d). In some instances, the numerical quantifier for at least one data member determined in (b) is displayed on the report in combination with a reference numerical quantifier. In some instances, the variation indicator calculated in (c) is displayed along a single axis having a range between low and high variation. In some instances, the one or more components identified and quantified in (d) are displayed in a pie chart indicating a percentage of each component.

In another aspect, disclosed herein are systems for analyzing a data set comprising information from a plurality of components from a single source, comprising: a database comprising the data set; and one or more computer processors that are coupled to the database, wherein the one or more computer processors are individually or collectively programmed to: (a) obtain the data set, the data set comprising sequence and quantity information for a plurality of data members across the plurality of components; (b) evaluate at least a subset of the data set to determine a numerical quantifier for at least one data member; (c) analyze at least a subset of the data set to calculate a variation indicator based on the sequence information; (d) apply a deconvolution algorithm to at least a subset of the data set to identify and quantify one or more components that constitute the plurality of components based on a plurality of data member signatures; (e) generate an output profile based on the numerical quantifier determined in (b), the variation indicator calculated in (c), and the one or more components identified and quantified in (d); and (f) recommend a procedure based on the output profile.

In another aspect, disclosed herein are systems for analyzing a data set comprising information from a plurality of components from a single source, comprising: a database comprising the data set; and one or more computer processors that are coupled to the database, wherein the one or more computer processors are individually or collectively programmed to: (a) obtain the data set, the data set comprising sequence and quantity information for a plurality of data members across the plurality of components; (b) evaluate at least a subset of the data set to determine a numerical quantifier for at least one data member; (c) analyze at least a subset of the data set to calculate a variation indicator based on the sequence information; (d) apply a deconvolution algorithm to at least a subset of the data set to identify and quantify one or more components that constitute the plurality of components based on a plurality of data member signatures; (e) generate an output profile based on the numerical quantifier determined in (b), the variation indicator calculated in (c), and the one or more components identified and quantified in (d); and (f) make a prediction of an outcome to a procedure based on the output profile, the prediction having a positive predictive value of at least 90% for at least 100 independent data sets.

In another aspect, disclosed herein are methods for generating an immune-oncology profile using ribonucleic acid (RNA) sequencing data, comprising: (a) obtaining RNA sequencing data from a sample obtained from a subject; (b) evaluating at least a subset of the RNA sequencing data to determine level of gene expression for at least one immune modulatory gene; (c) analyzing at least a subset of the RNA sequencing data to calculate a mutational burden based on a plurality of genes, wherein the mutation burden is calculated with a correlation of at least about 80% with a mutational burden Gold Standard; (d) applying a deconvolution algorithm to at least a subset of the RNA sequencing data to identify and quantify one or more cell types that are present in the sample based on a plurality of expression signature genes, wherein the one or more cell types are identified and quantified with a correlation of at least about 80% with a deconvolution Gold Standard; and (e) generating an immune-oncology profile based on the level of gene expression determined in (b), the mutational burden calculated in (c), and the one or more cell types quantified in (d). In some instances, the mutational burden is calculated with a correlation of at least about 90% with the mutational burden Gold Standard. Sometimes, the one or more cell types are identified and quantified with a correlation of at least about 90% with the deconvolution Gold Standard.

In another aspect, disclosed herein are methods for generating an immune-oncology profile using ribonucleic acid (RNA) sequencing data, comprising: (a) obtaining RNA sequencing data from a sample obtained from a subject; (b) evaluating at least a subset of the RNA sequencing data to determine level of gene expression for at least one immune modulatory gene; (c) analyzing at least a subset of the RNA sequencing data to calculate a mutational burden based on a plurality of genes, wherein the mutation burden is calculated at an accuracy of at least about 80%; (d) applying a deconvolution algorithm to at least a subset of the RNA sequencing data to identify and quantify one or more cell types that are present in the sample based on a plurality of expression signature genes, wherein the one or more cell types are identified and quantified at an accuracy of at least about 80%; and (e) generating an immune-oncology profile based on the level of gene expression determined in (b), the mutational burden calculated in (c), and the one or more cell types quantified in (d). In some instances, the mutational burden is calculated at a specificity of at least about 90%. Sometimes, the one or more cell types are identified and quantified at a specificity of at least about 90%.

In another aspect, disclosed herein are methods for generating an immune-oncology profile using ribonucleic acid (RNA) sequencing data, comprising: (a) obtaining RNA sequencing data from a sample obtained from a subject; (b) evaluating at least a subset of the RNA sequencing data to determine level of gene expression for at least one immune modulatory gene; (c) analyzing at least a subset of the RNA sequencing data to calculate a mutational burden based on a plurality of genes, wherein the mutation burden is calculated at a specificity of at least about 80%; (d) applying a deconvolution algorithm to at least a subset of the RNA sequencing data to identify and quantify one or more cell types that are present in the sample based on a plurality of expression signature genes, wherein the one or more cell types are identified and quantified at a specificity of at least about 80%; and (e) generating an immune-oncology profile based on the level of gene expression determined in (b), the mutational burden calculated in (c), and the one or more cell types quantified in (d). In some cases, the mutational burden is calculated at a specificity of at least about 90%. Sometimes, the one or more cell types are identified and quantified at a specificity of at least about 90%.

In another aspect, disclosed herein are methods for generating an immune-oncology profile using ribonucleic acid (RNA) sequencing data, comprising: (a) obtaining RNA sequencing data from a sample obtained from a subject; (b) evaluating at least a subset of the RNA sequencing data to determine level of gene expression for at least one immune modulatory gene; (c) analyzing at least a subset of the RNA sequencing data to calculate a mutational burden based on a plurality of genes, wherein the mutation burden is calculated at a sensitivity of at least about 80%; (d) applying a deconvolution algorithm to at least a subset of the RNA sequencing data to identify and quantify one or more cell types that are present in the sample based on a plurality of expression signature genes, wherein the one or more cell types are identified and quantified at a sensitivity of at least about 80%; and (e) generating an immune-oncology profile based on the level of gene expression determined in (b), the mutational burden calculated in (c), and the one or more cell types quantified in (d). Sometimes, the mutational burden is calculated at a sensitivity of at least about 90%. In certain instances, the one or more cell types are identified and quantified at a sensitivity of at least about 90%.

In another aspect, disclosed herein are methods for identifying at least one cell type in a biological sample comprising a plurality of cell types, comprising: (a) obtaining the biological sample from a subject and enriching for ribonucleic acids (RNA) corresponding to a plurality of expression signature genes present in a deconvolution matrix, the deconvolution matrix tailored to identify cell types present in the biological sample based on sample type; (b) sequencing the RNA to obtain RNA sequencing data; (c) determining a level of gene expression for the RNA enriched from the biological sample; (d) applying the deconvolution matrix to evaluate at least a subset of the RNA sequencing data and the level of gene expression to identify a plurality of cell types and proportions of the plurality of cell types at an accuracy of at least 90%. In some instances, the plurality of cell types includes at least two cell types. Sometimes, the plurality of cell types includes at least three cell types. In various aspects, the biological sample is a non-cancer sample. In certain cases, the biological sample is a cancer sample. The biological sample is oftentimes a non-cancer sample. In some instances, the plurality of expression signature genes comprises at least one gene from at least two of Tables 1A, 1B, 1C, 1D, and 1E. Sometimes, the plurality of expression signature genes comprises at least one gene from at least three of Tables 1A, 1B, 1C, 1D, and 1E. In various aspects, the plurality of expression signature genes comprises at least one gene from at least four of Tables 1A, 1B, 1C, 1D, and 1E. In certain cases, the plurality of expression signature genes comprises at least one gene from each of Tables 1A, 1B, 1C, 1D, and 1E. In some instances, the plurality of expression signature genes comprises at least 10, 20, 30, 40, 50, 60, 70, 80, 90, or 100 genes from Table 2, 3, or 4. Oftentimes, the method further comprises predicting a disease diagnosis based on the plurality of cell types and proportions of the plurality of cell types. In certain instances, sequencing the RNA comprises performing reverse transcription on the RNA to generate complementary DNA (cDNA). Sometimes, the method further comprises sequencing the cDNA or a derivative thereof to obtain the RNA sequencing data.

In some aspects, disclosed herein are methods for identifying at least one cell type in a biological sample comprising a plurality of cell types, comprising: (a) obtaining the biological sample from a subject and enriching for ribonucleic acids (RNA) corresponding to a plurality of expression signature genes present in a deconvolution matrix, the deconvolution matrix tailored to identify cell types present in the biological sample based on sample type; (b) sequencing the RNA to obtain RNA sequencing data; (c) determining a level of gene expression for the RNA enriched from the biological sample; (d) applying the deconvolution matrix to evaluate at least a subset of the RNA sequencing data and the level of gene expression to identify a plurality of cell types and proportions of the plurality of cell types at a specificity of at least 90%. In some instances, the plurality of cell types includes at least two cell types. Sometimes, the plurality of cell types includes at least three cell types. In various aspects, the biological sample is a non-cancer sample. In certain cases, the biological sample is a cancer sample. The biological sample is oftentimes a non-cancer sample. In some instances, the plurality of expression signature genes comprises at least one gene from at least two of Tables 1A, 1B, 1C, 1D, and 1E. Sometimes, the plurality of expression signature genes comprises at least one gene from at least three of Tables 1A, 1B, 1C, 1D, and 1E. In various aspects, the plurality of expression signature genes comprises at least one gene from at least four of Tables 1A, 1B, 1C, 1D, and 1E. In certain cases, the plurality of expression signature genes comprises at least one gene from each of Tables 1A, 1B, 1C, 1D, and 1E. In some instances, the plurality of expression signature genes comprises at least 10, 20, 30, 40, 50, 60, 70, 80, 90, or 100 genes from Table 2, 3, or 4. Oftentimes, the method further comprises predicting a disease diagnosis based on the plurality of cell types and proportions of the plurality of cell types. In certain instances, sequencing the RNA comprises performing reverse transcription on the RNA to generate complementary DNA (cDNA). Sometimes, the method further comprises sequencing the cDNA or a derivative thereof to obtain the RNA sequencing data.

In another aspect, disclosed herein are methods for identifying at least one cell type in a biological sample comprising a plurality of cell types, comprising: (a) obtaining the biological sample from a subject and enriching for ribonucleic acids (RNA) corresponding to a plurality of expression signature genes present in a deconvolution matrix, the deconvolution matrix tailored to identify cell types present in the biological sample based on sample type; (b) sequencing the RNA to obtain RNA sequencing data; (c) determining a level of gene expression for the RNA enriched from the biological sample; (d) applying the deconvolution matrix to evaluate at least a subset of the RNA sequencing data and the level of gene expression to identify a plurality of cell types and proportions of the plurality of cell types at a sensitivity of at least 90%. In some instances, the plurality of cell types includes at least two cell types. Sometimes, the plurality of cell types includes at least three cell types. In various aspects, the biological sample is a non-cancer sample. In certain cases, the biological sample is a cancer sample. The biological sample is oftentimes a non-cancer sample. In some instances, the plurality of expression signature genes comprises at least one gene from at least two of Tables 1A, 1B, 1C, 1D, and 1E. Sometimes, the plurality of expression signature genes comprises at least one gene from at least three of Tables 1A, 1B, 1C, 1D, and 1E. In various aspects, the plurality of expression signature genes comprises at least one gene from at least four of Tables 1A, 1B, 1C, 1D, and 1E. In certain cases, the plurality of expression signature genes comprises at least one gene from each of Tables 1A, 1B, 1C, 1D, and 1E. In some instances, the plurality of expression signature genes comprises at least 10, 20, 30, 40, 50, 60, 70, 80, 90, or 100 genes from Table 2, 3, or 4. Oftentimes, the method further comprises predicting a disease diagnosis based on the plurality of cell types and proportions of the plurality of cell types. In certain instances, sequencing the RNA comprises performing reverse transcription on the RNA to generate complementary DNA (cDNA). Sometimes, the method further comprises sequencing the cDNA or a derivative thereof to obtain the RNA sequencing data.

The present disclosure also provides computer-implemented methods for analyzing a biological sample obtained from a subject having a disease or condition, comprising: (a) obtaining gene expression data comprising the expression of at least one immune modulatory gene from the biological sample; (b) identifying and quantifying a percentage of at least one cell type that is present in the biological sample based on a plurality of expression signature genes; and (c) using a classifier to analyze the expression of the at least one immune modulatory gene and the percentage of the at least one cell type in order to classify the sample. In some instances, the sample is classified into one of at least two groups. In some instances, the at least two groups comprise a group having a positive response to a therapeutic intervention to the disease or condition and a group having a negative response to the therapeutic intervention. In some instances, the positive response comprises tumor regression, slowing tumor progression, or halt of tumor progression. In some instances, the negative response comprises tumor progression, lack of response to the therapeutic intervention, or a combination thereof. In some instances, the therapeutic intervention comprises immunotherapy. In some instances, the immunotherapy comprises a cancer vaccine, cytokine therapy, immune cell therapy, antibody therapy, or any combination thereof. In some instances, the therapeutic intervention comprises radiation, chemotherapy, surgery, or a combination thereof. In some instances, the method further comprises providing instructions to start, stop, change, or continue the therapeutic intervention. In some instances, the disease or condition is cancer. In some instances, the at least one cell type comprises at least one immune cell type. In some instances, the at least one immune cell type is selected from the group consisting of CD4+ memory T-cells, CD4+ naive T-cells, CD4+ T-cells, central memory T (Tcm) cells, effector memory T (Tem) cells, CD4+ Tcm, CD4+ Tem, CD8+ T-cells, CD8+ naive T-cells, CD8+ Tcm, CD8+ Tem, regulatory T cells (Tregs), T helper (Th) 1 cells, Th2 cells, gamma delta T (Tgd) cells, natural killer (NK) cells, natural killer T (NKT) cells, B-cells, naive B-cells, memory B-cells, class-switched memory B-cells, pro B-cells, and plasma cells. In some instances, the at least one immune cell type is selected from the group consisting of M1 macrophages, M2 macrophages, CD19+ B cells, CD14+ monocytes, CD56+ NK cells, CD8+ T cells, Treg cells, and CD4+ T cells. In some instances, the at least one immune modulatory gene is selected from the group consisting of CTLA4, OX40, PD-1, IDO1, CD47, PD-L1, TIM-3, BTLA, ICOS, and ARG1. In some instances, the at least one cell type comprises at least 2, 3, 4, 5, 6, 7, or 8 cell types. In some instances, the at least immune modulatory gene comprises at least 2, 3, 4, 5, 6, 7, 8, 9, or 10 genes. In some instances, the classifier is generated using a machine learning algorithm. In some instances, the machine learning algorithm is a random forest algorithm. In some instances, the classifier is trained using data from no more than 50 samples. In some instances, the biological sample comprises cancer or pre-cancer tissue. In some instances, the prediction of an outcome for the subject is a positive response or a negative response to a therapeutic intervention. In some instances, the prediction of an outcome for the subject is a prognosis of the disease or condition. In some instances, the percentage of the at least one cell type is generated using a deconvolution algorithm that applies a deconvolution matrix to RNA sequencing data for the biological sample. In some instances, the deconvolution algorithm applies a deconvolution matrix to the gene expression data to identify and quantify the percentage of the at least one cell type. In some instances, the deconvolution matrix comprises a plurality of immune cell expression signature genes. In some instances, the deconvolution matrix comprises a plurality of tumor cell expression signature genes. In some instances, the deconvolution matrix comprises a plurality of cell types, each cell type comprising a plurality of expression signature genes, wherein expression counts for each expression signature gene is normalized across the plurality of cell types. In some instances, the deconvolution algorithm identifies and quantifies the at least one cell type that is present in the biological sample using linear least-squares regression (LLSR), quadratic programming (QP), perturbation model for gene expression deconvolution (PERT), robust linear regression (RLR), microarray microdissection with analysis of differences (MMAD), digital sorting algorithm (DSA), or support vector regression. In some instances, the deconvolution algorithm performs an RNA normalization step to compensate for variation in RNA quantity amongst the at least one cell type in order to improve accuracy of the quantified percentage. In some instances, the deconvolution algorithm is a machine learning algorithm trained using comparison data comprising an actual percentage of the at least one cell type. In some instances, the actual percentage is generated using flow cytometry. In some instances, the method further comprises performing next generation RNA sequencing on the biological sample to obtain the RNA expression data and the plurality of expression signature genes. In some instances, the method further comprises obtaining mutational burden data for the biological sample and inputting the mutational burden data into the classifier for analysis in order to enhance classification of the biological sample. In some instances, the classifier is trained on data from no more than 15, 20, 25, 30, 35, 40, 45, or 50 samples and provides an accuracy of at least 70%, 75%, 80%, 85%, 90%, or 95%. In some instances, the accuracy is calculated using a leave-one-out cross-validation method. In some instances, the gene expression data is RNA sequencing data. In some instances, the gene expression data is obtained using next generation sequencing.

The present disclosure also discloses systems comprising for analyzing a biological sample obtained from a subject having a disease or condition, comprising: a database comprising the data set; and at least one computer processor that is coupled to the database, wherein the at least one computer processor is programmed to perform steps comprising: (a) obtaining gene expression data for at least one immune modulatory gene from the biological sample; (b) identifying and quantifying a percentage of at least one cell type that is present in the biological sample based on a plurality of expression signature genes; and (c) using a classifier to analyze the expression of the at least one immune modulatory gene and the percentage of the at least one cell type in order to classify the sample. In some instances, the sample is classified into one of at least two groups. In some instances, the at least two groups comprise a group having a positive response to a therapeutic intervention to the disease or condition and a group having a negative response to the therapeutic intervention. In some instances, the positive response comprises tumor regression, slowing tumor progression, or halt of tumor progression. In some instances, the negative response comprises tumor progression, lack of response to the therapeutic intervention, or a combination thereof. In some instances, the therapeutic intervention comprises immunotherapy. In some instances, the immunotherapy comprises a cancer vaccine, cytokine therapy, immune cell therapy, antibody therapy, or any combination thereof. In some instances, the therapeutic intervention comprises radiation, chemotherapy, surgery, or a combination thereof. In some instances, the at least one processor is further programmed to provide instructions to start, stop, change, or continue the therapeutic intervention. In some instances, the disease or condition is cancer. In some instances, the at least one cell type comprises at least one immune cell type. In some instances, the at least one immune cell type is selected from the group consisting of CD4+ memory T-cells, CD4+ naive T-cells, CD4+ T-cells, central memory T (Tcm) cells, effector memory T (Tem) cells, CD4+ Tcm, CD4+ Tem, CD8+ T-cells, CD8+ naive T-cells, CD8+ Tcm, CD8+ Tem, regulatory T cells (Tregs), T helper (Th) 1 cells, Th2 cells, gamma delta T (Tgd) cells, natural killer (NK) cells, natural killer T (NKT) cells, B-cells, naive B-cells, memory B-cells, class-switched memory B-cells, pro B-cells, and plasma cells. In some instances, the at least one immune cell type is selected from the group consisting of M1 macrophages, M2 macrophages, CD19+ B cells, CD14+ monocytes, CD56+ NK cells, CD8+ T cells, Treg cells, and CD4+ T cells. In some instances, the at least one immune modulatory gene is selected from the group consisting of CTLA4, OX40, PD-1, IDO1, CD47, PD-L1, TIM-3, BTLA, ICOS, and ARG1. In some instances, the at least one cell type comprises at least 2, 3, 4, 5, 6, 7, or 8 cell types. In some instances, the at least immune modulatory gene comprises at least 2, 3, 4, 5, 6, 7, 8, 9, or 10 genes. In some instances, the classifier is generated using a machine learning algorithm. In some instances, the machine learning algorithm is a random forest algorithm. In some instances, the classifier is trained using data from no more than 50 samples. In some instances, the biological sample comprises cancer or pre-cancer tissue. In some instances, the prediction of an outcome for the subject is a positive response or a negative response to a therapeutic intervention. In some instances, the prediction of an outcome for the subject is a prognosis of the disease or condition. In some instances, the percentage of the at least one cell type is generated using a deconvolution algorithm that applies a deconvolution matrix to RNA sequencing data for the biological sample. In some instances, the deconvolution algorithm applies a deconvolution matrix to the gene expression data to identify and quantify the percentage of the at least one cell type. In some instances, the deconvolution matrix comprises a plurality of immune cell expression signature genes. In some instances, the deconvolution matrix comprises a plurality of tumor cell expression signature genes. In some instances, the deconvolution matrix comprises a plurality of cell types, each cell type comprising a plurality of expression signature genes, wherein expression counts for each expression signature gene is normalized across the plurality of cell types. In some instances, the deconvolution algorithm identifies and quantifies the at least one cell type that is present in the biological sample using linear least-squares regression (LLSR), quadratic programming (QP), perturbation model for gene expression deconvolution (PERT), robust linear regression (RLR), microarray microdissection with analysis of differences (MMAD), digital sorting algorithm (DSA), or support vector regression. In some instances, the deconvolution algorithm performs an RNA normalization step to compensate for variation in RNA quantity amongst the at least one cell type in order to improve accuracy of the quantified percentage. In some instances, the deconvolution algorithm is a machine learning algorithm trained using comparison data comprising an actual percentage of the at least one cell type. In some instances, the actual percentage is generated using flow cytometry. In some instances, the RNA expression data and the plurality of expression signature genes are obtained from the biological sample using next generation RNA sequencing. In some instances, the at least one processor is further programmed to obtain mutational burden data for the biological sample and inputting the mutational burden data into the classifier for analysis in order to enhance classification of the biological sample. In some instances, the classifier is trained on data from no more than 15, 20, 25, 30, 35, 40, 45, or 50 samples and provides an accuracy of at least 70%, 75%, 80%, 85%, 90%, or 95%. In some instances, the accuracy is calculated using a leave-one-out cross-validation method. In some instances, the gene expression data is RNA sequencing data. In some instances, the gene expression data is obtained using next generation sequencing.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
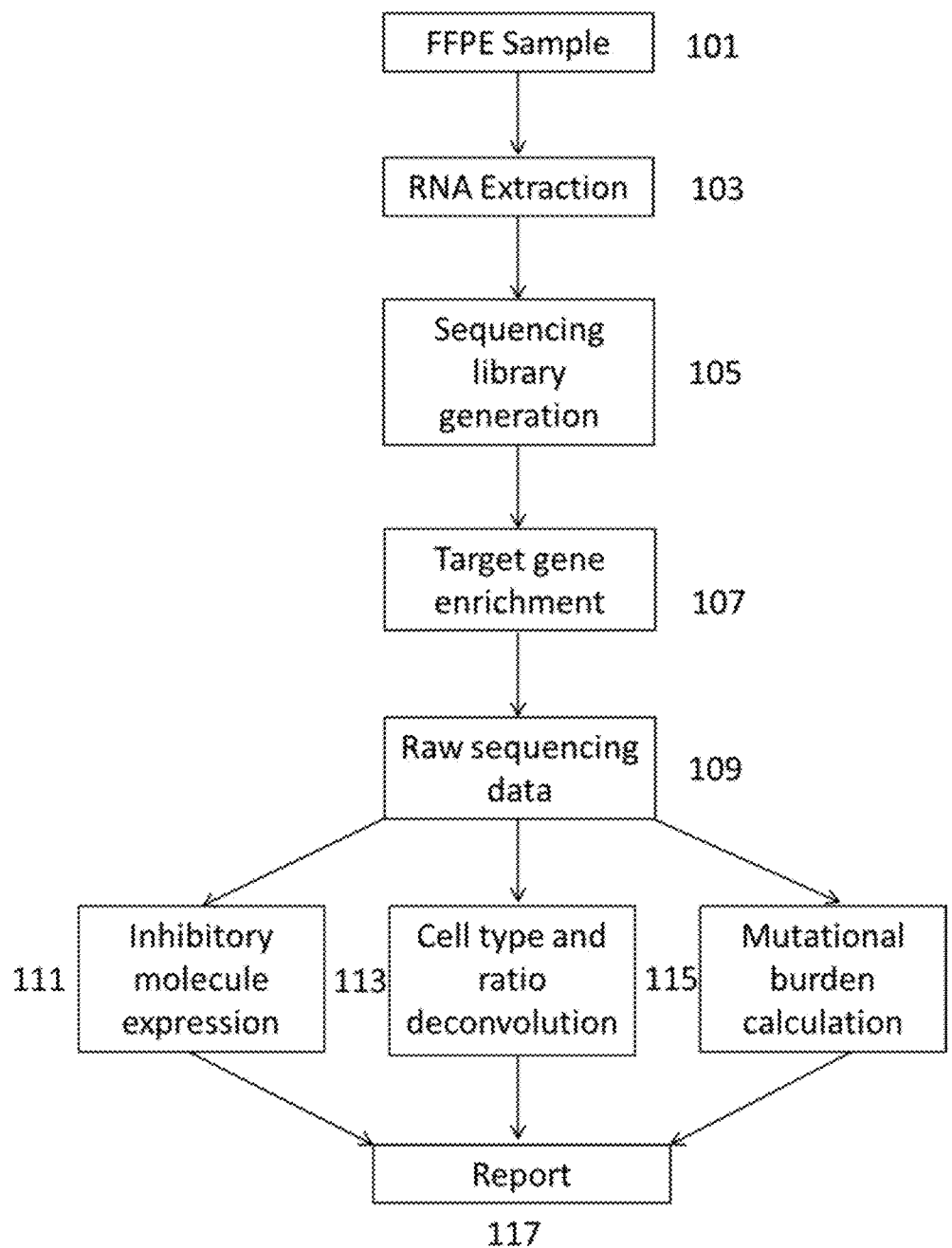
FIG. 1 depicts an example workflow for characterization of a tumor microenvironment.

The present disclosure employs, unless otherwise indicated, conventional molecular biology techniques, which are within the skill of the art. Unless defined otherwise, all technical and scientific terms used herein have the same meaning as is commonly understood by one of ordinary skill in the art.

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

The term "ribonucleic acid" or "RNA," as used herein refers to a molecule comprising at least one ribonucleotide residue. RNA may include transcripts. By "ribonucleotide" is meant a nucleotide with a hydroxyl group at the 2' position of a beta-D-ribo-furanose moiety. The term RNA includes, but not limited to, mRNA, ribosomal RNA, tRNA, non-protein-coding RNA (npcRNA), non-messenger RNA, functional RNA (fRNA), long non-coding RNA (lncRNA), pre-mRNAs, and primary miRNAs (pri-miRNAs). The term RNA includes, for example, double-stranded (ds) RNAs; single-stranded RNAs; and isolated RNAs such as partially purified RNA, essentially pure RNA, synthetic RNA, recombinant RNA, as well as altered RNA that differ from naturally-occurring RNA by the addition, deletion, substitution and/or alteration of one or more nucleotides. Such alterations can include addition of non-nucleotide material, such as to the end(s) of the siRNA or internally, for example at one or more nucleotides of the RNA. Nucleotides in the RNA molecules described herein can also comprise non-standard nucleotides, such as non-naturally occurring nucleotides or chemically synthesized nucleotides or deoxynucleotides. These altered RNAs can be referred to as analogs or analogs of naturally-occurring RNA.

Unless specifically stated or obvious from context, as used herein, the term "about" in reference to a number or range of numbers is understood to mean the stated number and numbers+/−10% thereof, or 10% below the lower listed limit and 10% above the higher listed limit for the values listed for a range.

The term "sample," as used herein, generally refers to a biological sample of a subject. The biological sample may be a tissue or fluid of the subject, such as blood (e.g., whole blood), plasma, serum, urine, saliva, mucosal excretions, sputum, stool and tears. The biological sample may be derived from a tissue or fluid of the subject. The biological sample may be a tumor sample or heterogeneous tissue sample. The biological sample may have or be suspected of having disease tissue. The tissue may be processed to obtain the biological sample. The biological sample may be a cellular sample. The biological sample may be a cell-free (or cell free) sample, such as cell-free DNA or RNA. The biological sample may comprise cancer cells, non-cancer cells, immune cells, non-immune cells, or any combination thereof. The biological sample may be a tissue sample. The biological sample may be a liquid sample. The liquid sample can be a cancer or non-cancer sample. Non-limiting examples of liquid biological samples include synovial fluid, whole blood, blood plasma, lymph, bone marrow, cerebrospinal fluid, serum, seminal fluid, urine, and amniotic fluid.

The term "variant," as used herein, generally refers to a genetic variant, such as an alteration, variant or polymorphism in a nucleic acid sample or genome of a subject. Such alteration, variant or polymorphism can be with respect to a reference genome, which may be a reference genome of the subject or other individual. Single nucleotide polymorphisms (SNPs) are a form of polymorphisms. In some examples, one or more polymorphisms comprise one or more single nucleotide variations (SNVs), insertions, deletions, repeats, small insertions, small deletions, small repeats, structural variant junctions, variable length tandem repeats, and/or flanking sequences. Copy number variants (CNVs), transversions and other rearrangements are also forms of genetic variation. A genomic alternation may be a base change, insertion, deletion, repeat, copy number variation, or transversion.

The term "subject," as used herein, generally refers to an animal, such as a mammalian species (e.g., human) or avian (e.g., bird) species, or other organism, such as a plant. More specifically, the subject can be a vertebrate, a mammal, a mouse, a primate, a simian or a human. Animals include, but are not limited to, farm animals, sport animals, and pets. The subject can be a healthy individual, an individual that has or is suspected of having a disease or a pre-disposition to the disease, or an individual that is in need of therapy or suspected of needing therapy. The subject can be a patient. The subject may have or be suspected of having a disease.

Generation of Immune-Oncology Profile

Provided herein are systems and methods for generating an immune-oncology profile using sequencing data. The immune-oncology profile often comprises at least one of immune modulatory molecule expression, cell type and ratio, and mutational burden for a given sample. In some cases, sequencing data is used to determine at least one of immune modulatory molecule expression, cell type and ratio, and mutational burden. Systems and methods for determining cell type and ratio may comprise deconvolution methods. An immune-oncology profile comprising immune modulatory molecule expression, cell type and ratio, and mutational burden may be used for therapeutic applications. For example, following determination of immune modulatory molecule expression, cell type and ratio, and mutational burden may provide information for diagnosis or treatment.

Figure 7:
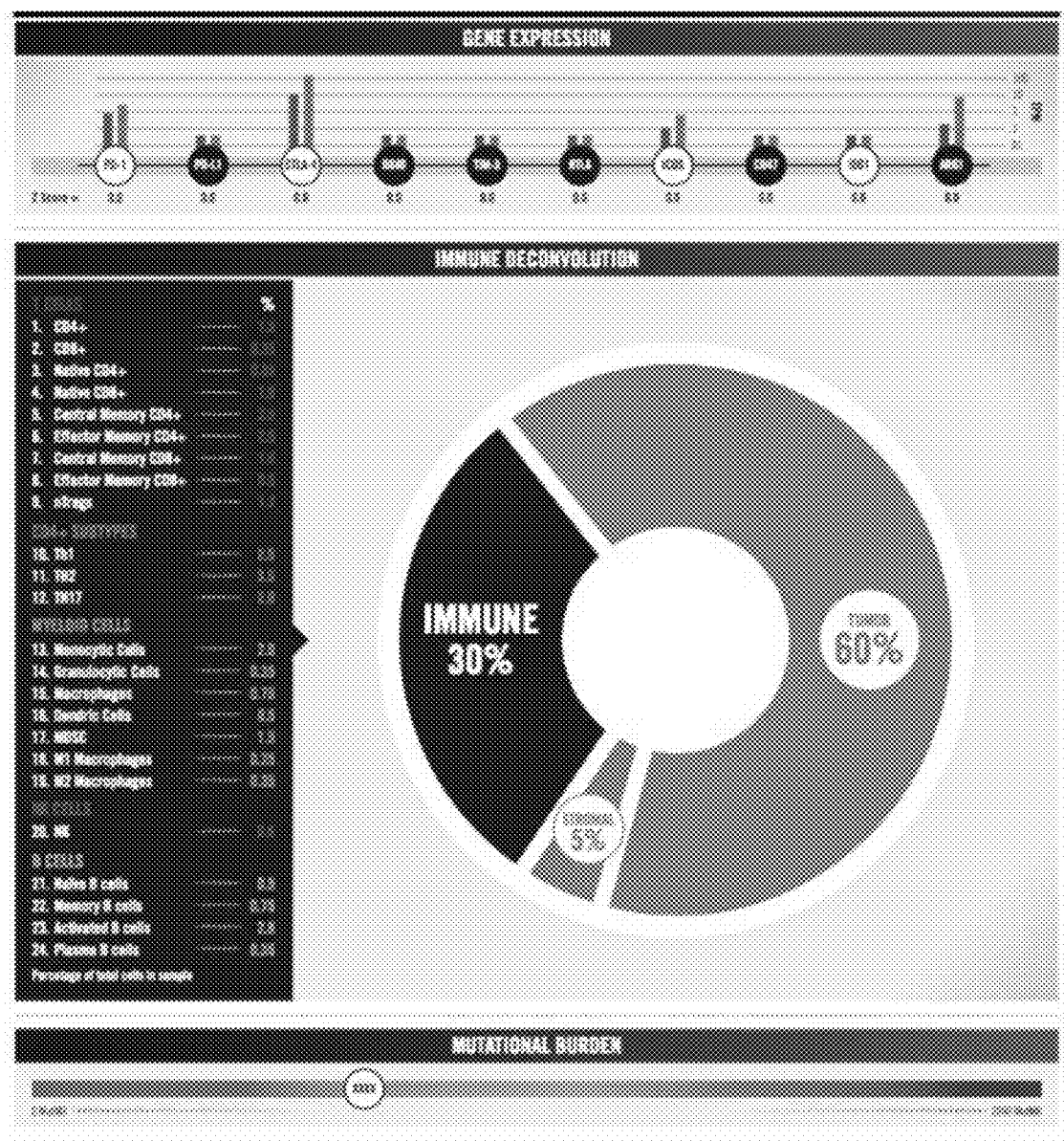
FIG. 7 depicts a report showing immune modulatory molecule expression, mutational burden, and cell deconvolution results.

A first example workflow process is depicted in FIG. 1. In a first step a formalin-fixed paraffin-embedded (FFPE) sample 101 is provided. RNA extraction 103 is performed followed by sequencing library generation 105. Target gene enrichment 107 is then performed followed by sequencing. Raw sequencing data 109 is generated, which is then used to determine immune modulatory molecule expression 111, cell type and ratio deconvolution 113, and perform mutational burden calculation 115. The immune modulatory molecule expression 111, cell type and ratio deconvolution 113, and mutational burden calculation 115 is then used to generate a report 117 of an immune-oncology profile. An example of a report is illustrated in FIG. 7, showing immune modulatory molecule expression, mutational burden, and cell type and ratio deconvolution results. Expression of immune modulatory or immune escape genes are shown at the top of the report in FIG. 7, which include PD-1, PD-L1, CTLA-4, OX-40, TIM-3, BTLA, ICOS, CD47, IDO1, and ARG1. The "immune deconvolution" section of the report includes a pie chart showing the percentages of general cell types identified in the sample, including 30% immune, 60% tumor, and 5% stromal. More specific breakdowns of the immune cell types and their percentages are shown at the left. The cell types are further divided into categories including T cells (CD4+, CD8+, naïve CD4+, naïve CD8+, Central Memory CD4+, Effector Memory CD4+, Central Memory CD8+, Effector Memory CD8+, and Tregs), CD4+ subtypes (Th1, Th2, Th17), Myeloid cells (monocytic cells, granulocytic cells, macrophages, dendritic cells, MDSC, M1 macrophages, M2 macrophages), NK cells, and B cells (naïve B cells, memory B cells, activated B cells, and plasma B cells). At the bottom of the report is a mutational burden readout. In this case, the mutational burden is provided as a graphic showing a scale between lower mutational burden to the left (left endpoint=0 MutMB) and increasing mutational burden to the right (right endpoint=2000 MutMB), with the circle indicating the sample's mutational burden position on this scale.

Provided herein are systems and methods for generating an immune-oncology profile from a sample of a subject. In some instances, the subject is has or is suspected of having a disease or disorder. In some instances, the immune-oncology profile is used for diagnosing the subject with a disease or disorder. Alternatively or in combination, the immune-oncology profile is used for determining or predicting a response to a therapeutic intervention in the subject.

Generation of an immune-oncology profile as described herein comprises first obtaining a sample from a subject. In some instances, the sample is any fluid or other material derived from the body of a normal or disease subject including, but not limited to, blood, serum, plasma, lymph, urine, saliva, tears, cerebrospinal fluid, milk, amniotic fluid, bile, ascites fluid, organ or tissue extract, and culture fluid in which any cells or tissue preparation from a subject has been incubated. In some instances, the sample is obtained from skin, blood, brain, bladder, bone, bone marrow, breast, colon, stomach, esophagus, ovary, uterus, gallbladder, fallopian tube, testicle, kidney, liver, pancreas, adrenal gland, cervix, endometrium, head or neck, lung, prostate, thymus, thyroid, lymph node, or urinary bladder. In some instances, the sample is a cancer sample. The cancer sample is typically a solid tumor sample or a liquid tumor sample. For example, the cancer sample is obtained from excised tissue. In some instances, the samples, is fresh, frozen, or fixed. In some instances, a fixed sample comprises paraffin-embedded or fixation by formalin, formaldehyde, or gluteraldehyde. In some instances, the sample is formalin-fixed paraffin-embedded.

In some instances, the sample is stored after it has been collected, but before additional steps are to be performed. In some instances, the sample is stored at less than 8° C. In some instances, the sample is stored at less than 4° C. In some instances, the sample is stored at less than 0° C. In some instances, the sample is stored at less than −20° C. In some instances, the sample is stored at less than −70° C. In some instances, the sample is stored a solution comprising glycerol, glycol, dimethyl sulfoxide, growth media, nutrient broth or any combination thereof. The sample may be stored for any suitable period of time. In some instances the sample is stored for any period of time and remains suitable for downstream applications. For example, the sample is stored for any period of time before nucleic acid (e.g., ribonucleic acid (RNA) or deoxyribonucleic acid (DNA)) extraction. In some instances, the sample is stored for at least or about 1 day, 2 day, 3 days, 4 days, 5 days, 6 days, 7 days, 1 week, 2 weeks, 3 weeks, 4 weeks, 1 month, 2 months, 3 months, 4 months, 5 months, 6 months, 7 months, 8 months, 9 months, 10 months, 11 months, 12 months, or more than 12 months. In some instances, the sample is stored for at least 1 year, 2 years, 3, years, 4 years, 5 years, 6 years, 7 years, 8 years, 9 years, 10 years, 11 years, 12 years, or more than 12 years.

Methods and systems as described herein comprise generating an immune-oncology profile from a sample of a subject, wherein the sample comprises a nucleic acid molecule. In some instances, the nucleic acid molecule is RNA, DNA, fragments, or combinations thereof. In some instances, after a sample is obtained, the sample is processed further before analysis. In some instances, the sample is processed to extract the nucleic acid molecule from the sample. In some instances, no extraction or processing procedures are performed on the sample. In some instances, the nucleic acid is extracted using any technique that does not interfere with subsequent analysis. Extraction techniques include, for example, alcohol precipitation using ethanol, methanol or isopropyl alcohol. In some instances, extraction techniques use phenol, chloroform, or any combination thereof. In some instances, extraction techniques use a column or resin based nucleic acid purification scheme such as those commonly sold commercially. In some instances, following extractions, the nucleic acid molecule is purified. In some instances, the nucleic acid molecule is further processed. For example, following extraction and purification, RNA is further reverse transcribed to cDNA. In some instances, processing of the nucleic acid comprises amplification. Following extraction or processing, in some instances, the nucleic acid is stored in water, Tris buffer, or Tris-EDTA buffer before subsequent analysis. In some instances, the sample is stored at less than 8° C. In some instances, the sample is stored at less than 4° C. In some instances, the sample is stored at less than 0° C. In some instances, the sample is stored at less than −20° C. In some instances, the sample is stored at less than −70° C. In some instances, the sample is stored for at least or about 1 day, 2 day, 3 days, 4 days, 5 days, 6 days, 7 days, 1 week, 2 weeks, 3 weeks, 4 weeks, 1 month, 2 months, 3 months, 4 months, 5 months, 6 months, 7 months, 8 months, 9 months, 10 months, 11 months, 12 months, or more than 12 months.

A nucleic acid molecule obtained from a sample comprises may be characterized by factors such as integrity of the nucleic acid molecule or size of the nucleic acid molecule. In some instances, the nucleic acid molecule is DNA. In some instances, the nucleic acid molecule is RNA. In some instances, the RNA or DNA comprises a specific integrity. For example, the RNA integrity number (RIN) of the RNA is no more than about 2. In some instances, the RNA molecules in a sample have a RIN of about 2 to about 10. In some instances, the RNA molecules in a sample have a RIN of at least about 2. In some instances, the RNA molecules in a sample have a RIN of at most about 10. In some instances, the RNA molecules in a sample have a RIN of about 2 to about 3, about 2 to about 4, about 2 to about 5, about 2 to about 6, about 2 to about 7, about 2 to about 8, about 2 to about 9, about 2 to about 10, about 3 to about 4, about 3 to about 5, about 3 to about 6, about 3 to about 7, about 3 to about 8, about 3 to about 9, about 3 to about 10, about 4 to about 5, about 4 to about 6, about 4 to about 7, about 4 to about 8, about 4 to about 9, about 4 to about 10, about 5 to about 6, about 5 to about 7, about 5 to about 8, about 5 to about 9, about 5 to about 10, about 6 to about 7, about 6 to about 8, about 6 to about 9, about 6 to about 10, about 7 to about 8, about 7 to about 9, about 7 to about 10, about 8 to about 9, about 8 to about 10, or about 9 to about 10. The RNA molecule in a sample may be characterized by size. In some instances, at least 10%, 20%, 30%, 40%, 50%, 60%, 70%, 80%, or 90%, or more of the RNA molecules in a sample are at least 150, 175, 200, 225, 250, 275, 300, 325, 350, 375, 400, or more than 400 nucleotides in size. In some instances, the RNA molecules in the sample are at least 200 nucleotides in size. In some instances, the RNA molecules of at least 200 nucleotides in size comprise a percentage of the sample (DV200). For example, the percentage is at least or about 40%, 45%, 50%, 55%, 60%, 65%, 70%, 75%, 80%, 85%, 90%, 95%, or more than 95%. In some instances, the RNA molecules in a sample have a DV200 value of about 10% to about 90%. In some instances, the RNA molecules in a sample have a DV200 value of at least about 10%. In some instances, the RNA molecules in a sample have a DV200 value of at most about 90%. In some instances, the RNA molecules in a sample have a DV200 value of about 10% to about 20%, about 10% to about 30%, about 10% to about 40%, about 10% to about 50%, about 10% to about 60%, about 10% to about 70%, about 10% to about 80%, about 10% to about 90%, about 20% to about 30%, about 20% to about 40%, about 20% to about 50%, about 20% to about 60%, about 20% to about 70%, about 20% to about 80%, about 20% to about 90%, about 30% to about 40%, about 30% to about 50%, about 30% to about 60%, about 30% to about 70%, about 30% to about 80%, about 30% to about 90%, about 40% to about 50%, about 40% to about 60%, about 40% to about 70%, about 40% to about 80%, about 40% to about 90%, about 50% to about 60%, about 50% to about 70%, about 50% to about 80%, about 50% to about 90%, about 60% to about 70%, about 60% to about 80%, about 60% to about 90%, about 70% to about 80%, about 70% to about 90%, or about 80% to about 90%.

In some instances, after the samples have been obtained and nucleic acid molecule isolated, the nucleic acid molecule is prepared for sequencing. In some instances, a sequencing library is prepared. Numerous library generation methods have been described. In some instances, methods for library generation comprise addition of a sequencing adapter. Sequencing adapters may be added to the nucleic acid molecule by ligation. In some instances, library generation comprises an end-repair reaction.

Sometimes, library generation for sequencing comprises an enrichment step. For example, coding regions of the mRNA are enriched. In some instances, the enrichment step is for a subset of genes. In some instances, the enrichment step comprises using a bait set. The bait set may be used to enrich for genes used for specific downstream applications. A bait set generally refers to a set of baits targeted toward a selected set of genomic regions of interest. For example, a bait set may be selected for genomic regions relating to at least one of immune modulatory molecule expression, cell type and ratio, or mutational burden. In some instances, one bait set is used for determining immune modulatory molecule expression, a second bait set is used for determining cell type and ratio, and a third bait set is used for determining mutational burden. In some instances, the same bait set is used for determining immune modulatory molecule expression, cell type and ratio, mutational burden, or combinations thereof. In some instances, a bait set comprises at least one unique molecular identifier (UMI). The term "unique molecular identifier (UMI)" or "UMI" as used herein refers to nucleic acid having a sequence which can be used to identify and/or distinguish one or more first molecules to which the UMI is conjugated from one or more second molecules. In some instances, the UMI is conjugated to one or more target molecules of interest or amplification products thereof. UMIs may be single or double stranded.

The systems and methods disclosed herein provide for the sequencing for a number of genes. In some instances, the number of genes is at least about 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10000, or more than 10000 genes. In some instances, the number of genes to be sequenced is in a range of about 500 to about 1000 genes. In some instances, the number of genes to be sequenced is in a range of about at least 200. In some instances, the number of genes to be sequenced is in a range of about at most 10,000. In some instances, the number of genes to be sequenced is in a range of about 200 to 500, 200 to 1,000, 200 to 2,000, 200 to 4,000, 200 to 6,000, 200 to 8,000, 200 to 10,000, 500 to 1,000, 500 to 2,000, 500 to 4,000, 500 to 6,000, 500 to 8,000, 500 to 10,000, 1,000 to 2,000, 1,000 to 4,000, 1,000 to 6,000, 1,000 to 8,000, 1,000 to 10,000, 2,000 to 4,000, 2,000 to 6,000, 2,000 to 8,000, 2,000 to 10,000, 4,000 to 6,000, 4,000 to 8,000, 4,000 to 10,000, 6,000 to 8,000, 6,000 to 10,000, or 8,000 to 10,000. Examples of genes to be sequenced are seen in Tables 1A-1E or Table 5.

Sequencing may be performed with any appropriate sequencing technology. Examples of sequencing methods include, but are not limited to single molecule real-time sequencing, Polony sequencing, sequencing by ligation, reversible terminator sequencing, proton detection sequencing, ion semiconductor sequencing, nanopore sequencing, electronic sequencing, pyrosequencing, Maxam-Gilbert sequencing, chain termination (e.g., Sanger) sequencing, +S sequencing, or sequencing by synthesis.

Sequencing methods may include, but are not limited to, one or more of: high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS) (Helicos), massively-parallel sequencing, Clonal Single Molecule Array (Solexa), shotgun sequencing, Maxim-Gilbert sequencing, and primer walking. Sequencing may generate sequencing reads ("reads"), which may be processed (e.g., alignment) to yield longer sequences, such as consensus sequences. Such sequences may be compared to references (e.g., a reference genome or control) to identify variants, for example.

An average read length from sequencing may vary. In some instances, the average read length is at least about 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, or more than 80000 base pairs. In some instances, the average read length is in a range of about 100 to 80,000. In some instances, the average read length is in a range of about at least 100. In some instances, the average read length is in a range of about at most 80,000. In some instances, the average read length is in a range of about 100 to 200, 100 to 300, 100 to 500, 100 to 1,000, 100 to 2,000, 100 to 4,000, 100 to 8,000, 100 to 10,000, 100 to 20,000, 100 to 40,000, 100 to 80,000, 200 to 300, 200 to 500, 200 to 1,000, 200 to 2,000, 200 to 4,000, 200 to 8,000, 200 to 10,000, 200 to 20,000, 200 to 40,000, 200 to 80,000, 300 to 500, 300 to 1,000, 300 to 2,000, 300 to 4,000, 300 to 8,000, 300 to 10,000, 300 to 20,000, 300 to 40,000, 300 to 80,000, 500 to 1,000, 500 to 2,000, 500 to 4,000, 500 to 8,000, 500 to 10,000, 500 to 20,000, 500 to 40,000, 500 to 80,000, 1,000 to 2,000, 1,000 to 4,000, 1,000 to 8,000, 1,000 to 10,000, 1,000 to 20,000, 1,000 to 40,000, 1,000 to 80,000, 2,000 to 4,000, 2,000 to 8,000, 2,000 to 10,000, 2,000 to 20,000, 2,000 to 40,000, 2,000 to 80,000, 4,000 to 8,000, 4,000 to 10,000, 4,000 to 20,000, 4,000 to 40,000, 4,000 to 80,000, 8,000 to 10,000, 8,000 to 20,000, 8,000 to 40,000, 8,000 to 80,000, 10,000 to 20,000, 10,000 to 40,000, 10,000 to 80,000, 20,000 to 40,000, 20,000 to 80,000, or 40,000 to 80,000.

In some instances, a number of nucleotides that are sequenced are at least or about 5, 10, 15, 20, 25, 30, 35, 40, 45, 50, 100, 150, 200, 300, 400, 500, 2000, 2500, 3000, or more than 3000 nucleotides. In some instances, the number of nucleotides that are sequenced are about 5 to about 3,000 nucleotides. In some instances, the number of that are sequenced are at least 5 nucleotides. In some instances, the number of nucleotides that are sequenced are at most 3,000 nucleotides. In some instances, the number of nucleotides that are sequenced are 5 to 50, 5 to 100, 5 to 200, 5 to 400, 5 to 600, 5 to 800, 5 to 1,000, 5 to 1,500, 5 to 2,000, 5 to 2,500, 5 to 3,000, 50 to 100, 50 to 200, 50 to 400, 50 to 600, 50 to 800, 50 to 1,000, 50 to 1,500, 50 to 2,000, 50 to 2,500, 50 to 3,000, 100 to 200, 100 to 400, 100 to 600, 100 to 800, 100 to 1,000, 100 to 1,500, 100 to 2,000, 100 to 2,500, 100 to 3,000, 200 to 400, 200 to 600, 200 to 800, 200 to 1,000, 200 to 1,500, 200 to 2,000, 200 to 2,500, 200 to 3,000, 400 to 600, 400 to 800, 400 to 1,000, 400 to 1,500, 400 to 2,000, 400 to 2,500, 400 to 3,000, 600 to 800, 600 to 1,000, 600 to 1,500, 600 to 2,000, 600 to 2,500, 600 to 3,000, 800 to 1,000, 800 to 1,500, 800 to 2,000, 800 to 2,500, 800 to 3,000, 1,000 to 1,500, 1,000 to 2,000, 1,000 to 2,500, 1,000 to 3,000, 1,500 to 2,000, 1,500 to 2,500, 1,500 to 3,000, 2,000 to 2,500, 2,000 to 3,000, or 2,500 to 3,000 nucleotides.

Sequencing methods may include a barcoding or "tagging" step. In some instances barcoding (or "tagging") can allow for generation of a population of samples of nucleic acids, wherein each nucleic acid can be identified from which sample the nucleic acid originated. In some instances, the barcode comprises oligonucleotides that are ligated to the nucleic acids. In some instances, the barcode is ligated using an enzyme, including but not limited to, *E. coli* ligase, T4 ligase, mammalian ligases (e.g., DNA ligase I, DNA ligase II, DNA ligase III, DNA ligase IV), thermostable ligases, and fast ligases.

Barcoding or tagging may occur using various types of barcodes or tags. Examples of barcodes or tags include, but are not limited to, a radioactive barcode or tag, a fluorescent barcode or tag, an enzyme, a chemiluminescent barcode or tag, and a colorimetric barcode or tag. In some instances, the barcode or tag is a fluorescent barcode or tag. In some instances, the fluorescent barcode or tag comprises a fluorophore. In some instances, the fluorophore is an aromatic or heteroaromatic compound. In some instances, the fluorophore is a pyrene, anthracene, naphthalene, acridine, stilbene, benzoxaazole, indole, benzindole, oxazole, thiazole, benzothiazole, canine, carbocyanine, salicylate, anthranilate, xanthenes dye, coumarin. Examples of xanthene dyes include, e.g., fluorescein and rhodamine dyes. Fluorescein and rhodamine dyes include, but are not limited to 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N; N'-tetramethyl-6-carboxyrhodamine (TAMRA), 6-carboxy-X-rhodamine (ROX). In some instances, the fluorescent barcode or tag also includes the naphthylamine dyes that have an amino group in the alpha or beta position. For example, naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl) aminonaphthalene-1-sulfonic acid (EDANS). Examples of coumarins include, e.g., 3-phenyl-7-isocyanatocoumarin; acridines, such as 9-isothiocyanatoacridine and acridine orange; N-(p-(2-benzoxazolyl)phenyl) maleimide; cyanines, such as, e.g., indodicarbocyanine 3 (Cy3), indodicarbocyanine 5 (Cy5), indodicarbocyanine 5.5 (Cy5.5), 3-(-carboxypentyl)-3'-ethyl-5,5'-dimethyloxacarbocyanine (CyA); 1H, 5H, 11H, 15H-Xantheno[2,3, 4-ij: 5,6, 7-i'j']diquinolizin-18-ium, 9-[2 (or 4)-[[[6-[2,5-dioxo-1-pyrrolidinyfloxy]-6-oxohexyl]amino]sulfonyl]-4 (or 2)-sulphonyl]-2,3, 6,7, 12,13, 16,17-octahydro-inner salt (TR or Texas Red); or BODIPY™ dyes.

In some instances, a different barcode or tag is supplied a sample comprising nucleic acids. Examples of barcode lengths include barcode sequences comprising, without limitation, about 1, 2, 3, 4, 5, 6, 7, 8, 9, 10, 15, 20, 25 or more bases in length. Examples of barcode lengths include barcode sequences comprising, without limitation, from 1-5, 1-10, 5-20, or 1-25 bases in length. Barcode systems may be in base 1, 2, 3, 4, 5, 6, 7, 8, 9, or 10 or a similar coding scheme. In some instances, a number of barcodes is at least or about 1, 2, 3, 4, 5, 6, 7, 8, 9, 10, 11, 12, 13, 14, 15, 16, 17, 18, 19, 20, 25, 50, 100, 200, 300, 400, 500, 600, 700, 800, 900, 1000, 2000, 4000, 6000, 8000, 10000, 12000, 14000, 16000, 18000, 20000, 25000, 30000, 40000, 50000, 100000, 500000, 1000000, or more than 1000000 barcodes. In some instances, a number of barcodes is in a range of 1-1000000 barcodes. In some instances, the number of barcodes is in a range of about 1-10 1-50 1-100 1-500 1-1000 1-5,000 1-10000 1-50000 1-100000 1-500000 1-1000000 10-50 10-100 10-500 10-1000 10-5,000 10-10000 10-50000 10-100000 10-500000 10-1000000 50-100 50-500 50-1000 50-5,000 50-10000 50-50000 50-100000 50-500000 50-1000000 100-500 100-1000 100-5,000 100-10000 100-50000 100-100000 100-500000 100-1000000 500-1000 500-5,000 500-10000 500-50000 500-100000 500-500000 500-1000000 1000-5,000 1000-10000 1000-50000 1000-100000 1000-500000 1000-1000000 5,000-10000 5,000-50000 5,000-100000 5,000-500000 5,000-1000000 10000-50000 10000-100000 10000-500000 10000-1000000 50000-100000 50000-500000 50000-1000000 100000-500000 100000-1000000 or 500000-1000000 barcodes.

Figure 2:
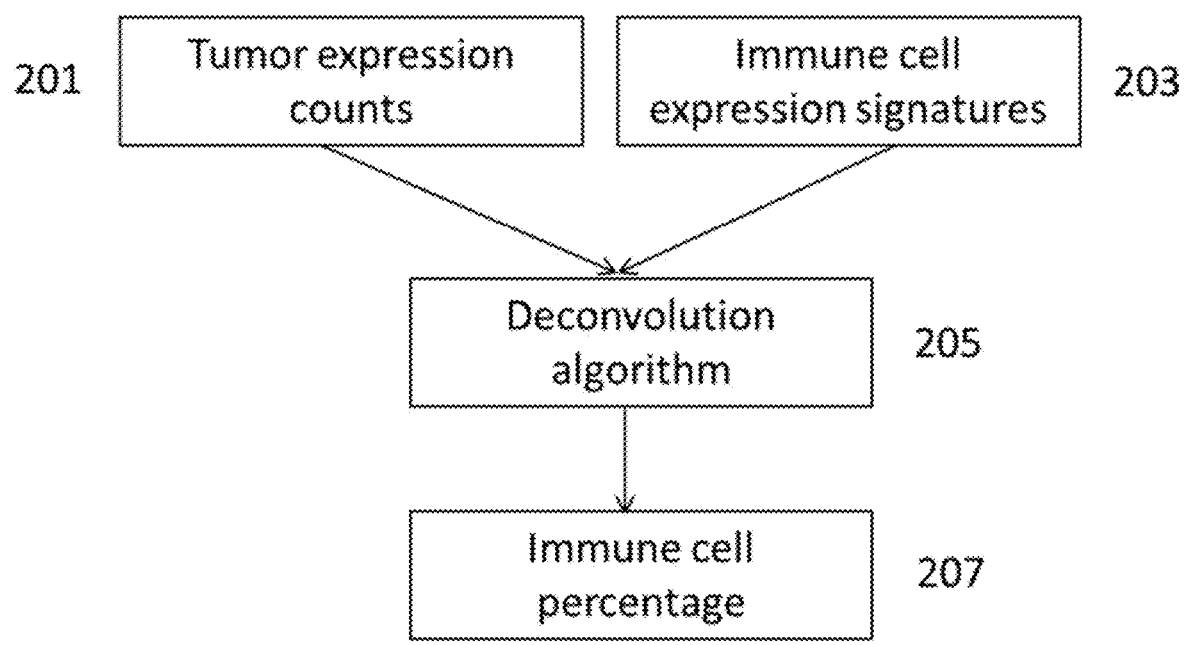
FIG. 2 depicts an example workflow for cell type and ratio deconvolution.

Following sequencing of a sample, sequencing data as described herein can be used for at least one of determining immune modulatory molecule expression, performing cell type and ratio deconvolution, and calculating mutational burden. An example of a workflow is seen in FIG. 2. Referring to FIG. 2, sequencing data is used to determine tumor expression counts 201 and immune cell expression signatures 203. The tumor expression counts 201 and immune cell expression signatures 203 are then subjected to a deconvolution algorithm 205 to calculate immune cell percentage 207.

Sequencing data as provided herein are used to determine gene expression. In some instances, the sequencing data is obtained from sequencing RNA from a sample. In some instances, the gene expression is of an immune modulatory molecule such as an immune checkpoint molecule or immune inhibitory molecule. Examples of immune modulatory molecules include, but are not limited to, one or more of 2B4 (CD244), A2aR, B7H3 (CD276), B7H4 (VTCN1), B7H6, B7RP1, BTLA (CD272), butyrophilins, CD103, CD122, CD137 (4-1BB), CD137L, CD160, CD2, CD200R, CD226, CD26, CD27, CD28, CD30, CD39, CD40, CD48, CD70, CD73, CD80 (B7.1), CD86 (B7.2), CEACAM1, CGEN-15049, CTLA-4, DR3, GAL9, GITR, GITRL, HVEM, ICOS, ICOSL (B7H2), IDOL, IDO2, ILT-2 (LILRB1), ILT-4 (LILRB2), KIR, KLRG1, LAG3, LAIR1 (CD305), LIGHT (TNFSF14), MARCO, NKG2A, NKG2D, OX-40, OX-40L, PD-1, PDL-1 (B7-H1, CD 274), PDL-2 (B7-DC, CD 273), PS, SIRPalpha (CD47), SLAM, TGFR, TIGIT, TIM1, TIM3 (HAVCR2), TIM4, or VISTA.

In some instances, the gene expression of a sample is compared to a reference sample. Sometimes, the systems and methods disclosed herein generate an immune-oncology profile comprising a visual representation of immune modulatory molecule gene expression. In some cases, the visual representation presents the gene expression of one or more immune modulatory molecules relative to a reference expression level. In some instances, the reference expression level is obtained from a reference sample. Sometimes, the reference sample comprises the same cell or tissue type as the sample being evaluated for gene expression. Sometimes, the gene expression of a sample is compared to an averaged or plurality of reference samples. As an example, a cancer sample being evaluated for gene expression is compared to average gene expression for reference samples of the same cancer type as the cancer sample in a reference database (e.g., TCGA database).

Provided herein are systems and methods for generating an immune-oncology profile comprising determining cell type and ratio in a sample using sequencing data. The sample often comprises a heterogeneous composition of different cell types and/or subtypes. Sometimes, the sample is a tumor sample. The cell types and/or subtypes that make up the sample includes one or more of cancer cells, non-cancer cells, and/or immune cells. Examples of non-immune cells include salivary gland cells, mammary gland cells, lacrimal gland cells, ceruminous gland cells, eccrine sweat gland cells, apocrine sweat gland cells, sebaceous gland cells, Bowman's gland cells, Brunner's gland cells, prostate gland cells, seminal vesicle cells, bulbourethral gland cells, keratinizing epithelial cells, hair shaft cells, epithelial cells, exocrine secretory epithelial cells, uterus endometrium cells, isolated goblet cells of respiratory and digestive tracts, stomach lining mucous cells, hormone secreting cells, pituitary cells, gut and respiratory tract cells, thyroid gland cells, adrenal gland cells, chromaffin cells, Leydig cells, theca interna cells, macula densa cells of kidney, peripolar cells of kidney, mesangial cells of kidney, hepatocytes, white fat cells, brown fat cells, liver lipocytes, kidney cells, kidney glomerulus parietal cells, kidney glomerulus podocytes, kidney proximal tubule brush border cells, loop of Henle thin segment cells, kidney distal tubule cells, endothelial fenestrated cells, vascular endothelial continuous cells, synovial cells, serosal cells, squamous cells, columnar cells of endolymphatic sac with microvilli, columnar cells of endolymphatic sac without microvilli, vestibular membrane cells, stria vascularis basal cells, stria vascularis marginal cells, choroid plexus cells, respiratory tract ciliated cells, oviduct ciliated cells, uterine endometrial ciliated cells, rete testis ciliated cells, ductulus efferens ciliated cells, ciliated ependymal cells of central nervous system, organ of Corti interdental epithelial cells, loose connective tissue fibroblasts, corneal fibroblasts, tendon fibroblasts, bone marrow reticular tissue fibroblasts, other nonepithelial fibroblasts, pericytes, skeletal muscle cells, red skeletal muscle cells, white skeletal muscle cells, intermediate skeletal muscle cells, nuclear bag cells of muscle spindle, nuclear chain cells of muscle spindle, satellite cells, cardiac muscle cells, ordinary cardiac muscle cells, nodal cardiac muscle cells, purkinje fiber cells, smooth muscle cells, myoepithelial cells of iris, myoepithelial cells of exocrine glands, erythrocytes, megakaryocytes, monocytes, epidermal Langerhans cells, osteoclasts, sensory neurons, olfactory receptor neurons, pain-sensitive primary sensory neurons, photoreceptor cells of retina in eye, photoreceptor rod cells, proprioceptive primary sensory neurons (various types), touch-sensitive primary sensory neurons, taste bud cells, autonomic neuron cells, Schwann cells, satellite cells, glial cells, astrocytes, oligodendrocytes, melanocytes, germ cells, nurse cells, interstitial cells, and pancreatic duct cells. Various cell types may be determined for the sample using methods as described herein including, but not limited to, lymphoid cells, stromal cells, stem cells, and myeloid cells. Examples of lymphoid cells include, but are not limited to, CD4+ memory T-cells, CD4+ naive T-cells, CD4+ T-cells, central memory T (Tcm) cells, effector memory T (Tem) cells, CD4+ Tcm, CD4+ Tem, CD8+ T-cells, CD8+ naive T-cells, CD8+ Tcm, CD8+ Tem, regulatory T cells (Tregs), T helper (Th) 1 cells, Th2 cells, gamma delta T (Tgd) cells, natural killer (NK) cells, natural killer T (NKT) cells, B-cells, naive B-cells, memory B-cells, class-switched memory B-cells, pro B-cells, and plasma cells. In some instances, the cells are stromal cells, for example, mesenchymal stem cells, adipocytes, preadipocytes, stromal cells, fibroblasts, pericytes, endothelial cells, microvascular endothelial cells, lymphatic endothelial cells, smooth muscle cells, chondrocytes, osteoblasts, skeletal muscle cells, myocytes. Examples of stem cells include, but are not limited to, hematopoietic stem cells, common lymphoid progenitor cells, common myeloid progenitor cells, granulocyte-macrophage progenitor cells, megakaryocyte-erythroid progenitor cells, multipotent progenitor cells, megakaryocytes, erythrocytes, and platelets. Examples of myeloid cells include, but are not limited to, monocytes, macrophages, macrophages M1, macrophages M2, dendritic cells, conventional dendritic cells, plasmacytoid dendritic cells, immature dendritic cells, neutrophils, eosinophils, mast cells, and basophils. Other cell types may be determined using methods as described herein, for example, epithelial cells, sebocytes, keratinocytes, mesangial cells, hepatocytes, melanocytes, keratocytes, astrocytes, and neurons.

In some instances, the sequencing data is used to determine immune cell expression. Examples of immune cells to be detected by methods described herein include, but are not limited to, CD4+ memory T-cells, CD4+ naive T-cells, CD4+ T-cells, central memory T (Tcm) cells, effector memory T (Tem) cells, CD4+ Tcm, CD4+ Tem, CD8+ T-cells, CD8+ naive T-cells, CD8+ Tcm, CD8+ Tem, regulatory T cells (Tregs), T helper (Th) 1 cells, Th2 cells, gamma delta T (Tgd) cells, natural killer (NK) cells, natural killer T (NKT) cells, B-cells, naive B-cells, memory B-cells, class-switched memory B-cells, pro B-cells, and plasma cells. In some instances, the sequencing data is used to determine expression of non-immune cells including, but not limited to, stromal cells, stem cells, or tumor cells.

Figure 3:
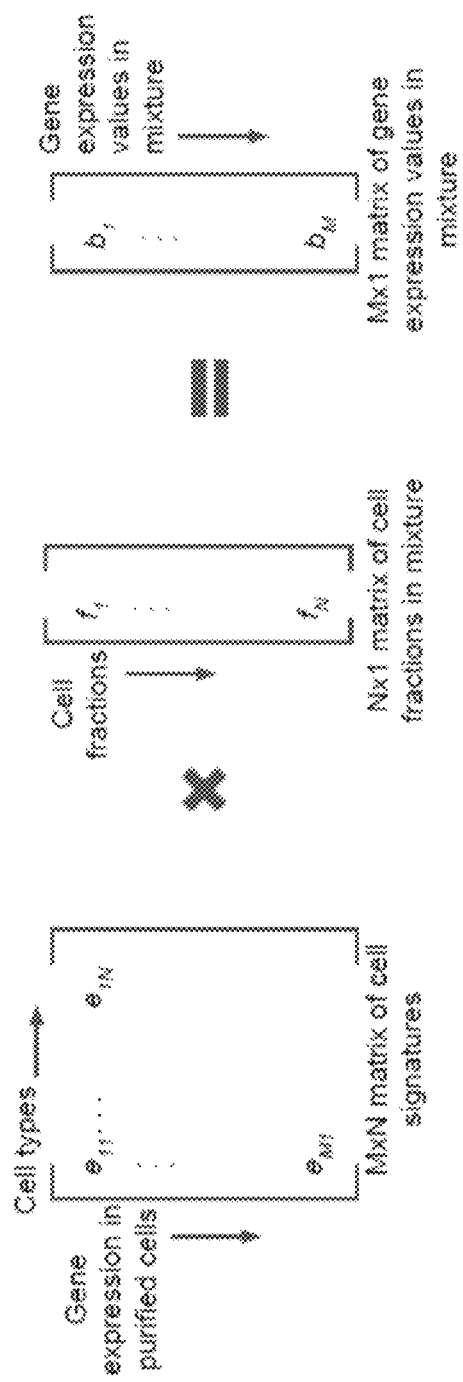
FIG. 3 depicts a schematic for normalization.

Methods and systems for determining cell type and ratio may comprise determining gene expression. In some instances, determining cell type and ratio may further comprise methods relating to deconvolution. In some instances, a deconvolution matrix is used. The deconvolution matrix typically comprises gene expression for one or more cell types. In some instances, the matrix is used for a complex data set of RNA sequencing gene expression data to allow for identification of cell types in the data and the relative proportions of each cell type. See FIG. 3. In some instances, individual cell types/subtypes and the relative proportion of these individual cell types/subtypes are determined from sequencing data using a deconvolution matrix. In some cases, the relative proportion of at least 2 cell types/subtypes, at least 3 cell types/subtypes, at least 4 cell types/subtypes, at least 5 cell types/subtypes, at least 6 cell types/subtypes, at least 7 cell types/subtypes, at least 8 cell types/subtypes, at least 9 cell types/subtypes, at least 10 cell types/subtypes, at least 11 cell types/subtypes, at least 12 cell types/subtypes, at least 13 cell types/subtypes, at least 14 cell types/subtypes, at least 15 cell types/subtypes, at least 16 cell types/subtypes, at least 17 cell types/subtypes, at least 18 cell types/subtypes, at least 19 cell types/subtypes, at least 20 cell types/subtypes, at least 21 cell types/subtypes, at least 22 cell types/subtypes, at least 23 cell types/subtypes, or at least 24 cell types are determined from sequencing data using a deconvolution matrix. A matrix equation illustrates the mathematical relationship between a matrix comprising expression signatures of individual cell types, the percentage of each cell type, and the bulk expression counts. In some instances, the matrix equation is $Ax=b$, where A is the cell expression fingerprints (i.e., deconvolution matrix), x is the cell percentages, and b is the bulk expression counts. In some instances, the matrix equation is solved by methods such as matrix algebra, regression analysis, and/or machine learning. Alternately or in combination, deconvolution methods comprise linear least-squares regression (LLSR), quadratic programming (QP), perturbation model for gene expression deconvolution (PERT), robust linear regression (RLR), microarray microdissection with analysis of differences (MMAD), digital sorting algorithm (DSA), or support vector regression (SVR). In some instances, deconvolution comprises a normalization step. Referring to FIG. 3, normalization may occur across a row or down a column. For example, normalization occurs across a row, wherein the row includes distinct cell types or down a column, wherein the column includes gene expression of cells for a specific cell type. In some instances, normalization occurs across a row. In some instances, cell fractions are considered in determining gene expression (FIG. 3). In some instances, a deconvolution matrix is generated for each type of sample analyzed. For example, certain cell types have a different gene expression signature depending on the local tissue environment. As a result, a one-size-fits-all deconvolution matrix is sometimes less accurate than a deconvolution matrix "tailored" to a specific sample type. In some instances, the deconvolution algorithm maintains a database comprising a plurality of deconvolution matrices. In some instances, the deconvolution algorithm selects a deconvolution matrix for analyzing the gene expression data of a sample based on the sample type. The use of a tailored deconvolution matrix enables the use of a narrower set of genes for deconvolution of the sample. The narrower set of genes can increase speed of analysis and the number of samples that are processed at one time. In some instances, a smaller capture or bait set is used to enrich for the narrower set of genes for downstream analysis (e.g., RNA-Seq).

Methods and systems for determining cell type and ratio comprising methods relating to deconvolution may further comprise normalizing RNA content. In some instances, the RNA content is normalized or corrected based on cell type. For example, RNA content is normalized based on the amount of RNA in an individual cell type. In some instances, normalizing RNA content comprises determining a number of cells used to generate the RNA. In some instances, the number of cells is determined by flow cytometry, manual cell counting, automated cell counting, microscopy, or spectrophotometry. In some instances, the number of cells is at least or about 30,000, 40,000, 50,000, 60,000, 70,000, 80,000, 90,000, 100,000, 200,000, 300,000, 400,000, 500,000, 600,000, 700,000, 800,000, 900,000, 1 million, 2 million, 3 million, 4 million, or more than 4 million cells.

Following determination of RNA content for an individual cell type, a correction value may be determined. In some instances, the cell is an immune cell. Examples of immune cells include, but are not limited to, a CD4+ T cell, a CD8+ T cell, a monocyte, a B-cell, a natural killer cell (NK), a M1 macrophage, or a M2 macrophage. In some instances, the immune cell is a CD4+ T cell. In some instances, a correction value for each individual cell type is determined. For example, the cell correction value for CD4+ T cell is about 1.00. Sometimes, the cell correction value for CD4+ T cell is from 0.9 to 1.1. In some instances, the cell correction value for CD8+ T cell is about 1.03. Sometimes, the cell correction value for CD8+ T cell is from 0.93 to 1.13. In some instances, the cell correction value for a monocyte is about 1.35. Sometimes, the cell correction value for a monocyte is from 1.25 to 1.45. In some instances, the cell correction value for a B-cell is about 0.53. Sometimes, the cell correction value for a B-cell is from 0.43 to 0.63. In some instances, the cell correction value for a natural killer cell (NK) is about 0.47. Sometimes, the cell correction value for a NK cell is from 0.37 to 0.57. In some instances, the cell correction value for a M1 macrophage is about 7.59. Sometimes, the cell correction value for a M1 macrophage is from 6.59 to 8.59. In some instances, the cell correction value for a M2 macrophage is about 12.26. Sometimes, the cell correction value for a M2 macrophage is from 11.26 to 13.26.

The correction value may be used to identify cell percentages of individual cell types. In some instances, the correction value is used in combination with deconvolution methods to determine cell percentages of individual cell types. In some instances, the correction value is applied prior to deconvolution methods. For example, the correction value is applied prior to support vector regression of RNA sequence data. In some instances, the correction value is applied following support vector regression and the cell types have been deconvoluted.

Methods and systems for determining cell type and ratio comprising methods relating to deconvolution and normalizing RNA content may result in an accurate determination of immune cell type percentages in a sample. In some instances, the accuracy is at least or about 20%, 25%, 30%, 35%, 40%, 45%, 50%, 60%, 70%, 80%, 90%, 95%, or more than 95% improved using methods and systems as described herein as compared to methods and systems where RNA content is not normalized.

An immune-oncology profile may comprise the cell types and ratios present in a sample using deconvolution of expression data for a plurality of genes. The genes typically exhibit differential expression in at least two cell types that are evaluated using deconvolution. In some cases, the genes exhibit differential expression between cancer and non-cancer cells, between different types of cancer cells, between immune and non-immune cells, between different types of immune cells, between different types of non-cancer cells, or any combination thereof. Examples of genes for inclusion in a deconvolution matrix include those listed in Tables 1A-1E. In some instances, a deconvolution matrix comprises at least about 10, 20, 30, 40, 50, 100, 150, 200, 250, 300, 350, 400, 450, 500, 650, 700, 750, 800, 850, 900, 950, 1000, 1500, 2000, 2500, 3000, or more than 3000 genes. In some instances, a deconvolution matrix comprises no more than about 10, 20, 30, 40, 50, 100, 150, 200, 250, 300, 350, 400, 450, 500, 650, 700, 750, 800, 850, 900, 950, 1000, 1500, 2000, 2500, or about 3000 genes. In some instances, a deconvolution matrix comprises a number of genes in a range of about 50 to 100, 50 to 200, 50 to 300, 50 to 400, 50 to 500, 50 to 600, 50 to 700, 50 to 800, 50 to 900, 50 to 1,000, 50 to 1,500, 100 to 200, 100 to 300, 100 to 400, 100 to 500, 100 to 600, 100 to 700, 100 to 800, 100 to 900, 100 to 1,000, 100 to 1,500, 200 to 300, 200 to 400, 200 to 500, 200 to 600, 200 to 700, 200 to 800, 200 to 900, 200 to 1,000, 200 to 1,500, 300 to 400, 300 to 500, 300 to 600, 300 to 700, 300 to 800, 300 to 900, 300 to 1,000, 300 to 1,500, 400 to 500, 400 to 600, 400 to 700, 400 to 800, 400 to 900, 400 to 1,000, 400 to 1,500, 500 to 600, 500 to 700, 500 to 800, 500 to 900, 500 to 1,000, 500 to 1,500, 600 to 700, 600 to 800, 600 to 900, 600 to 1,000, 600 to 1,500, 700 to 800, 700 to 900, 700 to 1,000, 700 to 1,500, 800 to 900, 800 to 1,000, 800 to 1,500, 900 to 1,000, 900 to 1,500, or 1,000 to 1,500 genes. In some instances, a deconvolution matrix comprises at least about 10, 20, 30, 40, 50, 60, 70, 80, 90, 100, 110, or about 120 genes from Tables 1A-1E. In some instances, a deconvolution matrix comprises no more than about 10, 20, 30, 40, 50, 60, 70, 80, 90, 100, 110, or about 120 genes from Tables 1A-1E.

TABLE 1A

| Deconvolution Genes for CD4+ T-cells | | | |
|---|---|---|---|
| ALS2CL | ANKRD55 | ZNF483 | TRAV13-1 |
| ST6GALNAC1 | SEMA3A | TRBV5-4 | DNAH8 |
| IL2RA | TRBV11-2 | TRAV8-2 | KRT72 |
| EPPK1 | FAM153B | TRAV12-2 | TRAV8-6 |
| TRBV6-5 | TRAV10 | IGKV5-2 | IGLV6-57 |
| TRAV12-1 | CTLA4 | TSHZ2 | FOXP3 |
| IGHV4-28 | TRAV2 | SORCS3 | TRAV5 |
| MDS2 | NTN4 | IGLV10-54 | DACT1 |
| TRBV5-5 | THEM5 | HPCAL4 | CD4 |

TABLE 1B

| Deconvolution Genes for CD8+ T-cells | | | |
|---|---|---|---|
| FLT4 | TRBV4-2 | TRBV6-4 | SPRY2 |
| S100B | TNIP3 | CD248 | ROBO1 |
| CD8B | TRBV2 | CYP4F22 | PZP |
| LAG3 | KLRC4-KLRK1 | CRTAM | SHANK1 |
| ANAPC1P1 | NRCAM | JAKMIP1 | KLRC2 |
| KLRC3 | CD8A | TRAV4 | FBLN2 |

TABLE 1C

| Deconvolution Genes for Monocytes | | | |
|---|---|---|---|
| DES | HLX | FPR3 | FCGR1B |
| LOXHD1 | EPHB2 | LPL | LIPN |
| AQP9 | MILR1 | RETN | GPNMB |
| CYP2S1 | PDK4 | LILRA6 | SEPT10 |
| PLA2G4A | FOLR2 | FOLR3 | C1QB |
| SLC6A12 | SLC22A16 | DOCK1 | NRG1 |
| RXFP2 | RIN2 | ARHGEF10L | |
| LPAR1 | CES1 | FPR2 | |

TABLE 1D

| Deconvolution Genes for NK cells | | | |
|---|---|---|---|
| IGFBP7 | LDB2 | GUCY1A3 | KLRF1 |
| DTHD1 | AKR1C3 | FASLG | KLRC1 |
| XCL1 | DAB2 | FAT4 | CD160 |
| BNC2 | CXCR1 | SIGLEC17P | SH2D1B |
| DGKK | ZMAT4 | LGALS9B | NMUR1 |
| LGALS9C | MLC1 | LIM2 | |
| NCR1 | CCNJL | PCDH1 | |

TABLE 1E

| Deconvolution Genes for B-cells | | | |
|---|---|---|---|
| UGT8 | IGKV1OR2-108 | IGHE | SCN3A |
| IGLV2-8 | IGKV1D-16 | MYO5B | ENAM |
| RP11-148O21.2 | IGLC7 | IGHV1-2 | IGKJ5 |

TABLE 1E-continued

| Deconvolution Genes for B-cells | | | |
|---|---|---|---|
| SOX5 | TNFRSF13B | IGKV2D-29 | IGKV1-17 |
| IGLV2-18 | IGHV2-70 | CHL1 | |
| IGKV3D-20 | IGLV8-61 | IGKV6-21 | |

There are potentially around 19,700 possible gene identifiers that can be used from the transcriptome for generating a basis or deconvolution matrix. In some instances, genes are selected for deconvolution if the genes are differentially expressed in pairwise cell type differential expression analysis. In some instances, genes are selected for deconvolution if the genes are expressed at a consistent level within a cell type across samples. The present disclosure has identified a small subset of the transcriptome as being useful for carrying out deconvolution of immune cell types. Table 2 shows a list of 293 total genes and corresponding Ensembl gene identifiers in a 15 differentially expressed gene list. The genes in Table 2 are generated by performing pairwise comparisons for each cell type and tallying up the top 15 differentially expressed genes in each comparison. Tables 3 and 4 show genes generated using this same approach with Table 3 showing a 10 differentially expressed gene list (232 total genes) and Table 4 showing a 5 differentially expressed gene list (134 total genes). Table 2 has the longest list since it includes the top 15 differentially expressed genes. Table 3 has a gene list that is a subset of Table 2. Likewise, Table 4 has a gene list that is a subset of Table 3. In some instances, a deconvolution matrix comprises at least about 10, 20, 30, 40, 50, 60, 70, 80, 90, 100, 150, 200, or about 250 genes from Table 2. In some instances, a deconvolution matrix comprises no more than about 10, 20, 30, 40, 50, 60, 70, 80, 90, 100, 150, 200, or about 250 genes from Table 2. In some instances, a deconvolution matrix comprises at least about 10, 20, 30, 40, 50, 60, 70, 80, 90, 100, 150, or about 200 genes from Table 3. In some instances, a deconvolution matrix comprises no more than about 10, 20, 30, 40, 50, 60, 70, 80, 90, 100, 150, or about 200 genes from Table 3. In some instances, a deconvolution matrix comprises at least about 10, 20, 30, 40, 50, 60, 70, 80, 90, 100, 110, 120, or about 130 genes from Table 4. In some instances, a deconvolution matrix comprises no more than about 10, 20, 30, 40, 50, 60, 70, 80, 90, 100, 110, 120, or about 130 genes from Table 4.

TABLE 2

| Top 15 Differentially Expressed Genes | | | |
|---|---|---|---|
| gene_id | gene_name | gene_id | gene_name |
| ENSG00000128203.6 | ASPHD2 | ENSG00000105369.8 | CD79A |
| ENSG00000171777.14 | RASGRP4 | ENSG00000146373.15 | RNF217 |
| ENSG00000186469.7 | GNG2 | ENSG00000152969.15 | JAKMIP1 |
| ENSG00000186806.5 | VSIG10L | ENSG00000146776.13 | ATXN7L1 |
| ENSG00000198894.6 | CIPC | ENSG00000068831.17 | RASGRP2 |
| ENSG00000156475.17 | PPP2R2B | ENSG00000186891.12 | TNFRSF18 |
| ENSG00000178199.12 | ZC3H12D | ENSG00000155307.16 | SAMSN1 |
| ENSG00000206190.10 | ATP10A | ENSG00000183023.17 | SLC8A1 |
| ENSG00000117090.13 | SLAMF1 | ENSG00000240891.5 | PLCXD2 |
| ENSG00000263528.6 | IKBKE | ENSG00000175857.7 | GAPT |
| ENSG00000198851.8 | CD3E | ENSG00000103313.10 | MEFV |
| ENSG00000100351.15 | GRAP2 | ENSG00000100365.13 | NCF4 |
| ENSG00000146285.12 | SCML4 | ENSG00000164483.15 | SAMD3 |
| ENSG00000197208.5 | SLC22A4 | ENSG00000125810.9 | CD93 |
| ENSG00000126217.19 | MCF2L | ENSG00000178562.16 | CD28 |
| ENSG00000186827.9 | TNFRSF4 | ENSG00000151948.10 | GLT1D1 |
| ENSG00000111913.14 | FAM65B | ENSG00000153563.14 | CD8A |
| ENSG00000182183.13 | FAM159A | ENSG00000134460.14 | IL2RA |
| ENSG00000175489.9 | LRRC25 | ENSG00000132185.15 | FCRLA |
| ENSG00000170962.11 | PDGFD | ENSG00000152582.11 | SPEF2 |
| ENSG00000104974.9 | LILRA1 | ENSG00000101842.12 | VSIG1 |

TABLE 2-continued

Top 15 Differentially Expressed Genes

| gene_id | gene_name | gene_id | gene_name |
|---|---|---|---|
| ENSG00000185883.9 | ATP6V0C | ENSG00000168229.3 | PTGDR |
| ENSG00000151490.12 | PTPRO | ENSG00000203747.8 | FCGR3A |
| ENSG00000157445.13 | CACNA2D3 | ENSG00000011600.10 | TYROBP |
| ENSG00000184060.9 | ADAP2 | ENSG00000085514.14 | PILRA |
| ENSG00000172243.16 | CLEC7A | ENSG00000104972.13 | LILRB1 |
| ENSG00000158869.9 | FCER1G | ENSG00000065413.15 | ANKRD44 |
| ENSG00000100427.14 | MLC1 | ENSG00000196220.14 | SRGAP3 |
| ENSG00000150045.10 | KLRF1 | ENSG00000162415.6 | ZSWIM5 |
| ENSG00000018280.15 | SLC11A1 | ENSG00000167984.15 | NLRC3 |
| ENSG00000122223.11 | CD244 | ENSG00000178573.6 | MAF |
| ENSG00000176928.5 | GCNT4 | ENSG00000173258.11 | ZNF483 |
| ENSG00000162599.14 | NFIA | ENSG00000187554.10 | TLR5 |
| ENSG00000131042.12 | LILRB2 | ENSG00000069020.17 | MAST4 |
| ENSG00000164398.11 | ACSL6 | ENSG00000181036.12 | FCRL6 |
| ENSG00000160683.4 | CXCR5 | ENSG00000172456.15 | FGGY |
| ENSG00000102445.17 | KIAA0226L | ENSG00000010671.14 | BTK |
| ENSG00000160883.9 | HK3 | ENSG00000114013.14 | CD86 |
| ENSG00000198816.5 | ZNF358 | ENSG00000144218.17 | AFF3 |
| ENSG00000179041.3 | RRS1 | ENSG00000104043.13 | ATP8B4 |
| ENSG00000053524.10 | MCF2L2 | ENSG00000129450.7 | SIGLEC9 |
| ENSG00000102245.6 | CD40LG | ENSG00000082074.14 | FYB |
| ENSG00000124203.5 | ZNF831 | ENSG00000153064.10 | BANK1 |
| ENSG00000137441.7 | FGFBP2 | ENSG00000164867.9 | NOS3 |
| ENSG00000109944.9 | C11orf63 | ENSG00000143226.12 | FCGR2A |
| ENSG00000183813.6 | CCR4 | ENSG00000011590.12 | ZBTB32 |
| ENSG00000198879.10 | SFMBT2 | ENSG00000160185.12 | UBASH3A |
| ENSG00000173208.3 | ABCD2 | ENSG00000163393.11 | SLC22A15 |
| ENSG00000144843.10 | ADPRH | ENSG00000133574.8 | GIMAP4 |
| ENSG00000183621.14 | ZNF438 | ENSG00000196218.10 | RYR1 |
| ENSG00000174946.6 | GPR171 | ENSG00000128218.7 | VPREB3 |
| ENSG00000066056.12 | TIE1 | ENSG00000181847.10 | TIGIT |
| ENSG00000176438.11 | SYNE3 | ENSG00000155849.14 | ELMO1 |
| ENSG00000153283.11 | CD96 | ENSG00000182621.15 | PLCB1 |
| ENSG00000167286.8 | CD3D | ENSG00000148655.13 | C10orf11 |
| ENSG00000179934.6 | CCR8 | ENSG00000128815.16 | WDFY4 |
| ENSG00000127507.16 | EMR2 | ENSG00000188404.7 | SELL |
| ENSG00000167850.3 | CD300C | ENSG00000100368.12 | CSF2RB |
| ENSG00000197629.5 | MPEG1 | ENSG00000141293.14 | SKAP1 |
| ENSG00000100385.12 | IL2RB | ENSG00000213047.10 | DENND1B |
| ENSG00000133561.14 | GIMAP6 | ENSG00000196418.11 | ZNF124 |
| ENSG00000179921.13 | GPBAR1 | ENSG00000113319.10 | RASGRF2 |
| ENSG00000263264.1 | CTB-133G6.1 | ENSG00000140968.9 | IRF8 |
| ENSG00000152213.3 | ARL11 | ENSG00000066294.13 | CD84 |
| ENSG00000077420.14 | APBB1IP | ENSG00000188848.14 | BEND4 |
| ENSG00000145416.12 | 1-Mar | ENSG00000183918.13 | SH2D1A |
| ENSG00000095585.15 | BLNK | ENSG00000236609.3 | ZNF853 |
| ENSG00000158714.9 | SLAMF8 | ENSG00000165521.14 | EML5 |
| ENSG00000188822.7 | CNR2 | ENSG00000013725.13 | CD6 |
| ENSG00000030419.15 | IKZF2 | ENSG00000110002.14 | VWA5A |
| ENSG00000151366.11 | NDUFC2 | ENSG00000134539.15 | KLRD1 |
| ENSG00000121964.13 | GTDC1 | ENSG00000170006.10 | TMEM154 |
| ENSG00000126264.8 | HCST | ENSG00000042980.11 | ADAM28 |
| ENSG00000010030.12 | ETV7 | ENSG00000142303.12 | ADAMTS10 |
| ENSG00000186265.8 | BTLA | ENSG00000162881.6 | OXER1 |
| ENSG00000187796.12 | CARD9 | ENSG00000150681.8 | RGS18 |
| ENSG00000182866.15 | LCK | ENSG00000103569.8 | AQP9 |
| ENSG00000100450.11 | GZMH | ENSG00000186074.17 | CD300LF |
| ENSG00000158473.6 | CD1D | ENSG00000172116.20 | CD8B |
| ENSG00000149970.13 | CNKSR2 | ENSG00000100055.19 | CYTH4 |
| ENSG00000104490.16 | NCALD | ENSG00000170909.12 | OSCAR |
| ENSG00000107954.9 | NEURL1 | ENSG00000035720.6 | STAP1 |
| ENSG00000155846.15 | PPARGC1B | ENSG00000139193.3 | CD27 |
| ENSG00000034400.13 | CASP10 | ENSG00000066336.10 | SPI1 |
| ENSG00000115956.9 | PLEK | ENSG00000110448.9 | CD5 |
| ENSG00000175556.15 | LONRF3 | ENSG00000184221.11 | OLIG1 |
| ENSG00000187116.12 | LILRA5 | ENSG00000005471.14 | ABCB4 |
| ENSG00000165591.6 | FAAH2 | ENSG00000105227.13 | PRX |
| ENSG00000140090.16 | SLC24A4 | ENSG00000145990.9 | GFOD1 |
| ENSG00000010319.5 | SEMA3G | ENSG00000159339.12 | PADI4 |
| ENSG00000136573.11 | BLK | ENSG00000105374.8 | NKG7 |
| ENSG00000155629.13 | PIK3AP1 | ENSG00000235568.5 | NFAM1 |
| ENSG00000177455.10 | CD19 | ENSG00000110777.10 | POU2AF1 |
| ENSG00000152495.9 | CAMK4 | ENSG00000154655.13 | L3MBTL4 |
| ENSG00000117091.8 | CD48 | ENSG00000158481.11 | CD1C |
| ENSG00000170819.4 | BFSP2 | ENSG00000140678.15 | ITGAX |
| ENSG00000198821.9 | CD247 | ENSG00000146094.12 | DOK3 |

TABLE 2-continued

Top 15 Differentially Expressed Genes

| gene_id | gene_name | gene_id | gene_name |
| --- | --- | --- | --- |
| ENSG00000173762.6 | CD7 | ENSG00000117009.10 | KMO |
| ENSG00000120278.13 | PLEKHG1 | ENSG00000164124.9 | TMEM144 |
| ENSG00000119866.19 | BCL11A | ENSG00000247077.5 | PGAM5 |
| ENSG00000120594.15 | PLXDC2 | ENSG00000132704.14 | FCRL2 |
| ENSG00000145649.7 | GZMA | ENSG00000107242.16 | PIP5K1B |
| ENSG00000158517.12 | NCF1 | ENSG00000142235.7 | LMTK3 |
| ENSG00000180061.8 | TMEM150B | ENSG00000186854.9 | TRABD2A |
| ENSG00000127152.16 | BCL11B | ENSG00000196159.10 | FAT4 |
| ENSG00000116824.4 | CD2 | ENSG00000106034.16 | CPED1 |
| ENSG00000170458.12 | CD14 | ENSG00000154451.13 | GBP5 |
| ENSG00000090376.7 | IRAK3 | ENSG00000167995.14 | BEST1 |
| ENSG00000000938.11 | FGR | ENSG00000151623.13 | NR3C2 |
| ENSG00000143184.4 | XCL1 | ENSG00000112182.13 | BACH2 |
| ENSG00000180739.13 | S1PR5 | ENSG00000124772.10 | CPNE5 |
| ENSG00000012124.13 | CD22 | ENSG00000221926.10 | TRIM16 |
| ENSG00000177272.8 | KCNA3 | ENSG00000130810.18 | PPAN |
| ENSG00000172673.9 | THEMIS | ENSG00000049768.13 | FOXP3 |
| ENSG00000273749.3 | CYFIP1 | ENSG00000198223.13 | CSF2RA |
| ENSG00000278540.3 | ACACA | ENSG00000271383.5 | NBPF19 |
| ENSG00000136404.14 | TM6SF1 | ENSG00000079263.17 | SP140 |
| ENSG00000086730.15 | LAT2 | ENSG00000073861.2 | TBX21 |
| ENSG00000255587.6 | RAB44 | ENSG00000105383.13 | CD33 |
| ENSG00000163519.12 | TRAT1 | ENSG00000111052.6 | LIN7A |
| ENSG00000198734.9 | F5 | ENSG00000196092.11 | PAX5 |
| ENSG00000117322.15 | CR2 | ENSG00000171051.7 | FPR1 |
| ENSG00000065675.13 | PRKCQ | ENSG00000162654.8 | GBP4 |
| ENSG00000198574.5 | SH2D1B | ENSG00000159958.4 | TNFRSF13C |
| ENSG00000187912.10 | CLEC17A | ENSG00000010610.8 | CD4 |
| ENSG00000267534.2 | S1PR2 | ENSG00000126759.11 | CFP |
| ENSG00000119535.16 | CSF3R | ENSG00000104921.13 | FCER2 |
| ENSG00000166523.6 | CLEC4E | ENSG00000160856.19 | FCRL3 |
| ENSG00000164330.15 | EBF1 | ENSG00000080493.12 | SLC4A4 |
| ENSG00000163563.7 | MNDA | ENSG00000186462.8 | NAP1L2 |
| ENSG00000179088.13 | C12orf42 | ENSG00000261371.4 | PECAM1 |
| ENSG00000145687.14 | SSBP2 | ENSG00000085265.9 | FCN1 |
| ENSG00000205544.3 | TMEM256 | ENSG00000205730.6 | ITPRIPL2 |
| ENSG00000172543.6 | CTSW | ENSG00000266412.4 | NCOA4 |
| ENSG00000124406.15 | ATP8A1 | ENSG00000087903.11 | RFX2 |
| ENSG00000136867.9 | SLC31A2 | ENSG00000161405.15 | IKZF3 |
| ENSG00000113263.11 | ITK | ENSG00000144152.11 | FBLN7 |
| ENSG00000172578.10 | KLHL6 | ENSG00000165071.13 | TMEM71 |
| ENSG00000119457.7 | SLC46A2 | ENSG00000265808.3 | SEC22B |
| ENSG00000153485.5 | TMEM251 | ENSG00000162804.12 | SNED1 |
| ENSG00000203710.9 | CR1 | ENSG00000105967.14 | TFEC |
| ENSG00000175294.5 | CATSPER1 | ENSG00000197540.6 | GZMM |
| ENSG00000111452.11 | GPR133 | ENSG00000090612.19 | ZNF268 |
| ENSG00000160654.8 | CD3G | ENSG00000171596.6 | NMUR1 |
| ENSG00000189430.11 | NCR1 | | |
| ENSG00000197705.8 | KLHL14 | | |
| ENSG00000089012.13 | SIRPG | | |
| ENSG00000181409.10 | AATK | | |
| ENSG00000112394.15 | SLC16A10 | | |

Provided herein are systems and methods for determining an immune-oncology profile comprising determining cell type and ratio using deconvolution methods, wherein following deconvolution, percentages of immune cells may be determined. In some instances, immune cells may be further grouped based on shared lineage and percentages of immune cells based on lineage is determined. For example, immune cells are divided into T cells, CD4+ subtypes, myeloid cells, and natural killer cells. In some instances, percentages of non-immune cells are determined. In some instances, percentages of immune cells and percentages of non-immune cells are determined. Sometimes, an immune-oncology profile comprises determining a percentage of immune cells and non-immune cells such as tumor cells and/or stromal cells.

Following deconvolution, a number of cell types of various immune and non-immune cell types may be determined. In some instances, deconvolution identifies at least or about 2, 3, 4, 5, 6, 7, 8, 9, 10, 11, 12, 13, 14, 15, 16, 17, 18, 19, 20, or more than 20 immune cell types. In some instances, deconvolution identifies a range of about 5 to about 20 immune cell types. In some instances, deconvolution identifies at least or about 5 to 10, 5 to 15, 5 to 20, 10 to 15, 10 to 20, or 15 to 20 immune cell types. Deconvolution may be used to identify non-immune cell types. In some instances, deconvolution identifies at least or about 2, 3, 4, 5, 6, 7, 8, 9, 10, 11, 12, 13, 14, 15, 16, 17, 18, 19, 20, or more than 20 non-immune cell types. In some instances, deconvolution identifies a range of about 5 to about 20 non-immune cell types. In some instances, deconvolution identifies at least or about 5 to 10, 5 to 15, 5 to 20, 10 to 15, 10 to 20, or 15 to 20 non-immune cell types. In some cases, deconvolution results are evaluated by comparing to the Gold Standard. Sometimes, the Gold Standard is generated by sorting the samples evaluated by deconvolution. For example, a sample is split into two portions with one portion evaluated by nucleic acid sequencing and deconvolution and the other portion evaluated by sorting (e.g., flow cytometry or FACS) to obtain the Gold Standard. The results of the deconvolution are then compared to the Gold Standard to evaluate for accuracy, specificity, sensitivity, correlation to the Gold Standard, or any combination thereof.

Provided herein are systems and methods for generating an immune-oncology profile comprising mutational burden determined using sequencing data. In some instances, mutational burden is calculated for somatic mutations. In some instances, mutational burden is calculated by excluding germline variations. Germline variations may be excluded based on frequency. In some instances, exclusion is based on a frequency of at least 0.01%, 0.05%, 0.1%, 0.5%, 1%, 2%, 5%, 10%, 15%, 20%, 25% or more than 25%. In some instances, the germline variations are determined using germline variation databases.

Mutational burden may be determined using a plurality of genes. Examples of genes used to determine mutational burden are seen in Table 5. In some instances, a number of genes for determining mutational burden is at least or about 250 to 5,000 genes. In some instances, a number of genes for determining mutational burden is at least or about 250 genes. In some instances, a number of genes for determining mutational burden is at most 5,000 genes. In some instances, a number of genes for determining mutational burden is at least or about 250 to 500, 250 to 750, 250 to 1,000, 250 to 1,500, 250 to 2,000, 250 to 2,500, 250 to 3,000, 250 to 3,500, 250 to 4,000, 250 to 4,500, 250 to 5,000, 500 to 750, 500 to 1,000, 500 to 1,500, 500 to 2,000, 500 to 2,500, 500 to 3,000, 500 to 3,500, 500 to 4,000, 500 to 4,500, 500 to 5,000, 750 to 1,000, 750 to 1,500, 750 to 2,000, 750 to 2,500, 750 to 3,000, 750 to 3,500, 750 to 4,000, 750 to 4,500, 750 to 5,000, 1,000 to 1,500, 1,000 to 2,000, 1,000 to 2,500, 1,000 to 3,000, 1,000 to 3,500, 1,000 to 4,000, 1,000 to 4,500, 1,000 to 5,000, 1,500 to 2,000, 1,500 to 2,500, 1,500 to 3,000, 1,500 to 3,500, 1,500 to 4,000, 1,500 to 4,500, 1,500 to 5,000, 2,000 to 2,500, 2,000 to 3,000, 2,000 to 3,500, 2,000 to 4,000, 2,000 to 4,500, 2,000 to 5,000, 2,500 to 3,000, 2,500 to 3,500, 2,500 to 4,000, 2,500 to 4,500, 2,500 to 5,000, 3,000 to 3,500, 3,000 to 4,000, 3,000 to 4,500, 3,000 to 5,000, 3,500 to 4,000, 3,500 to 4,500, 3,500 to 5,000, 4,000 to 4,500, 4,000 to 5,000, or 4,500 to 5,000 genes.

Mutational burden as determined herein may be determined as a range between low and high mutational burden. In some instances, mutational burden is determined as low, medium, or high mutational burden. Sometimes, mutational burden is determined as the number of nonsynonymous somatic mutations per megabase in the exome. In some cases, mutational burden is compared to the Gold Standard mutational burden calculated using paired normal analysis of DNA. Specifically, the Gold Standard mutational burden measures somatic mutations using DNA sequence data obtained from the sample by comparing allele frequencies in normal and tumor sample alignments, annotating the identified mutations, and aggregating the mutations.

TABLE 5

Mutational Burden Genes

| | | | | | | |
|---|---|---|---|---|---|---|
| TC2N | TRAF6 | PRMT2 | STIM2 | DDX59 | EYA3 | DPF2 |
| LIPA | TRAF5 | PRMT3 | STIM1 | DDX58 | AGAP3 | UBQLN4 |
| TBL3 | GDPD5 | PRMT6 | N4BP1 | DDX54 | AGAP6 | UBR1 |
| LIMA1 | GEM | SMARCA2 | N4BP2 | ATP6V0A2 | AEBP1 | ARID1B |
| LIN54 | GKAP1 | SMAP1 | N4BP2L2 | DDX51 | ADSS | ARRDC1 |
| LIMK1 | TPRKB | SMAD7 | NDUFA3 | DDX50 | ADPRH | ARRB2 |
| TCF4 | TPR | PRKRIP1 | NHLRC2 | DDX5 | FADS1 | UBR2 |
| TCF3 | TPP2 | SMARCC2 | NHLRC3 | ZNF438 | TUBG1 | DNAJB14 |
| LIN7B | TPP1 | PRKAG2 | NID1 | ATP5SL | ADNP | DPH1 |
| TCF25 | TPMT | SMARCC1 | NID2 | DENND2D | ADNP2 | DPH2 |
| TCF20 | GLA | PRKAR1A | NGDN | DENND1A | TUBGCP2 | DPP7 |
| TCF12 | GLCE | PRKAR1B | NIN | ATP5G2 | ADSL | ARID2 |
| TCERG1 | GIT2 | PRKAR2A | NIPAL2 | UPF3B | FAAH | DPP3 |
| TBL1X | GIPC1 | PRKCA | STAB1 | UQCC2 | ZNF707 | ARID4A |
| TBKBP1 | GIGYF2 | PRKCD | STAG1 | UQCRB | F8 | ARID4B |
| LMO7 | GIMAP4 | PRKCE | NDUFA4 | BMI1 | F3 | ARID5B |
| LMTK2 | GIMAP6 | SMARCB1 | NFKBIE | USP35 | ADRM1 | ARRDC3 |
| TBK1 | GIMAP7 | PRKCI | NFIX | USP38 | EVI2B | EFNB1 |
| LNX2 | GOLGA5 | PRKCZ | NFKBIA | ZNF384 | AGFG1 | ANO10 |
| LONP1 | TP53 | SMAD4 | NFYC | USP40 | AGRN | EFTUD2 |
| TBC1D8 | TOX4 | SMAD3 | NFRKB | BET1 | AGTPBP1 | DHX34 |
| LOXL1 | TNKS | SLMAP | NFX1 | BFAR | ZNF691 | ZNF574 |
| TBC1D5 | TNK2 | PRR14 | NFYA | USP47 | EXOC2 | DHX32 |
| LMNB1 | TNIP1 | PRR14L | NIPBL | ZNF37A | EXOC1 | DHX36 |
| TBCK | GRK5 | SLTM | NIPSNAP1 | USP34 | ZNF689 | DHX37 |
| TBCEL | TNFRSF21 | SLPI | NLRX1 | BDH1 | AHCTF1 | ANP32B |
| TBCE | TNFRSF1B | PROSER1 | NMD3 | BHLHE40 | EXD3 | DHX57 |
| LLGL2 | TNKS1BP1 | PRR4 | NISCH | USP24 | EXD2 | ATG16L2 |
| LLPH | GRB10 | PRRC2B | NME6 | CYP51A1 | TUT1 | DHX30 |
| TBCD | GPS2 | PRR12 | NME7 | ZNF397 | AHCYL1 | EHMT1 |
| LMAN2L | TNPO2 | PRPSAP2 | NLRP1 | BCL2L11 | AHCYL2 | EHHADH |
| LMBRD1 | GPRC5C | SMAD2 | NLRC5 | BCL2L12 | AHDC1 | ZNF576 |
| LMBRD2 | TNKS2 | PRPF18 | NLN | BCL2L13 | AHI1 | ANKS1A |
| LMF1 | GRAMD1A | PRPF3 | ST7L | BCL2L2 | AHNAK | EHD1 |
| LIMD1 | GRN | PRPF38B | NKAP | BCL6 | AHR | EHBP1L1 |
| TCF7 | GSTO1 | PRPF4 | NKTR | BCL7B | EVL | EHBP1 |
| TECPR1 | GTDC1 | PRPF40A | ST6GALNAC4 | USP25 | EVI5L | EGR2 |
| LCMT2 | GTF2E2 | PRPF8 | ST3GAL4 | USP28 | EVI5 | EGR1 |
| TECR | GRWD1 | SMAD1 | NFIA | BCL9 | AGPS | ZNF568 |
| LCOR | GSAP | PPP4C | NFE2L1 | BCL9L | EXT2 | EFCAB2 |
| LCORL | TNFRSF10B | PPP4R1 | NDUFB8 | BCLAF1 | AGFG2 | DIEXF |
| LCP1 | GSPT1 | SMG6 | NDUFB9 | USP3 | EXT1 | ANXA6 |

TABLE 5-continued

Mutational Burden Genes

| | | | | | | |
|---|---|---|---|---|---|---|
| LDB1 | GSPT2 | PPP6C | NDUFC2 | BCOR | AGGF1 | ATF7IP2 |
| LDHA | GSR | PPP6R1 | NDUFS2 | USP30 | AGK | AOAH |
| LDLR | TNRC18 | PPP6R3 | NDUFS7 | BCR | AGL | UBE2E2 |
| LDLRAD4 | TNRC6A | PPRC1 | NDUFV1 | USP31 | AGO1 | DIP2A |
| TDRKH | TNRC6B | PPWD1 | NECAP1 | USP32 | AGO2 | DIP2B |
| LCLAT1 | GOSR1 | SMG7 | NDUFA8 | USP48 | AGO3 | ATF6 |
| TELO2 | GOSR2 | PPP1R7 | NDUFA9 | CYP20A1 | EXOSC7 | ATF5 |
| LATS1 | TOPBP1 | PPP2R5A | STAM | BLMH | EXOSC2 | ATF4 |
| TET2 | TOP3B | PPP2R5B | NEO1 | CYB561A3 | EXOSC10 | DIDO1 |
| LBR | TOP2B | PPP2R5C | NEU3 | CYB561 | AGO4 | DHX8 |
| TESK2 | GPALPP1 | PPP2R5E | NEURL4 | EXOG | EXOC7 | DIAPH1 |
| TESK1 | GPAM | PQLC1 | STAMBP | USPL1 | EPS8L2 | ANTXR2 |
| TESC | GPATCH2 | PQLC3 | NEDD1 | CXorf40A | ZNF615 | ANXA1 |
| TERF1 | GPATCH2L | PRKAA1 | NF1 | BLZF1 | EML4 | ZNF571 |
| TEP1 | GOPC | PREPL | NFATC1 | BIVM | EML3 | ANXA2 |
| TDRD7 | TOR2A | PRDX5 | NFATC2IP | USP5 | UBA7 | ANXA3 |
| TCP11L2 | TOR1AIP1 | PRDX6 | NFATC3 | ZNF362 | ANKAR | DICER1 |
| TCP11L1 | TOPORS | PREB | NENF | USP53 | ANKDD1A | EFCAB7 |
| TCOF1 | GOLGB1 | SMG1 | NEDD9 | USP54 | ZNF609 | ATG2A |
| LHPP | GOLIM4 | SMARCD1 | NEK1 | ZNF358 | ZNF608 | EIF4A2 |
| TCHP | GOLM1 | PRIMPOL | NEK3 | USP6NL | ANKHD1 | EIF3G |
| LIG3 | GON4L | PRADC1 | NEK4 | USP7 | ANKIB1 | ATG9A |
| LGALSL | GPATCH8 | SMCHD1 | NEK6 | CYLD | ZNF606 | ANKRD36 |
| LGALS9 | TNRC6C | SMC4 | NEK7 | BIN1 | UBA3 | DHRS3 |
| LEPR | GPR155 | PRC1 | SPATA7 | USP9X | ANAPC1 | ANKRD39 |
| LETMD1 | TOM1L2 | PRCC | PLEKHA5 | CYHR1 | ENOSF1 | DHRS12 |
| TDP2 | GPBP1 | PRDM10 | PLEKHB2 | CYFIP2 | UAP1 | EIF4G3 |
| LFNG | TNS3 | PRDM11 | PLEKHG1 | CYCS | ENO1 | EIF4G2 |
| TDP1 | TNS1 | PRDM15 | PLEKHG2 | CYBRD1 | ANAPC7 | DHCR7 |
| TDG | GPR137 | PRDM2 | PLEC | CYBB | ENKD1 | EIF4G1 |
| LGALS3BP | TOP1MT | PRDM4 | SNIP1 | BIRC3 | ENGASE | UNK |
| TCTN3 | GPD2 | PRRC2C | PLEKHJ1 | BIRC6 | ENG | ATHL1 |
| TCTN2 | TOP1 | QKI | PLEKHM2 | CYB5R4 | ANAPC2 | ZNF592 |
| TBC1D4 | GPR107 | PTPRE | PLEKHM3 | B3GNTL1 | ANKLE2 | ATG7 |
| LTA4H | GPR108 | PTPN18 | PLEK | DBN1 | ANKRD13C | ATG4B |
| LTBP1 | FLYWCH1 | PTPN2 | PLCD1 | DBF4B | ELK4 | EIF2AK3 |
| LTBP3 | FMNL1 | PTPN23 | PLAGL2 | DBF4 | ELK3 | ANKRD50 |
| LTBR | FMO5 | PTPN6 | PLAUR | DAZAP1 | ANKRD16 | EIF2AK2 |
| LTN1 | FMR1 | PTPRA | PLBD1 | USP12 | ANKRD17 | ATG4A |
| LTV1 | FN1 | PTPRC | PLCB2 | USP13 | UBAP1 | ANKRD42 |
| LUM | FLNA | PTPRF | PLCB3 | USP14 | ZNF597 | ATG2B |
| LUZP1 | FNBP4 | PTPRJ | SNRK | USP15 | ELF1 | DHTKD1 |
| TAMM41 | FNDC3A | PTPRM | PLCG1 | BACE2 | UBAP2 | DHX15 |
| LSG1 | FNDC3B | PTPRS | PLCL2 | BACH1 | UBAP2L | EIF2AK4 |
| TAOK2 | FLNB | PTRHD1 | SNRNP200 | B4GALT2 | ANKRD26 | ANKRD44 |
| TAOK1 | FKBP7 | SLFN13 | PLD2 | DCAF4 | ANKRD27 | ZNF585A |
| TANGO6 | FKBP15 | PTEN | PML | DCAF17 | ELAVL1 | EIF3E |
| TANGO2 | FKBP1C | PTGES2 | PLXNB1 | DCAF16 | EIF5B | EIF3D |
| LRSAM1 | FKBP2 | PTK7 | PLXNB2 | DCAF13 | ANKRD28 | ANKRD46 |
| LRWD1 | FKBP4 | PTOV1 | PLXND1 | BAG3 | ANKRD12 | EIF3C |
| LSM6 | FKBP5 | PXMP2 | SNAPC4 | BBS2 | ELL2 | ATG4D |
| LSM4 | FKBP8 | PXN | PMPCA | DAB2 | ANKRA2 | EIF2S3L |
| LYSMD4 | FLCN | SLC4A7 | PMPCB | BBS9 | ANKMY1 | DHRS4 |
| LYST | FLI1 | PYGB | PMS1 | DAAM2 | EMC10 | EIF2D |
| TAF2 | FNIP1 | PYGL | PMS2 | CYYR1 | EMB | EIF2B3 |
| TAF1C | FNIP2 | PYGO2 | PLXNA3 | CYTIP | ELP6 | DNAJC24 |
| LZTR1 | FNTA | PYROXD1 | PLXDC2 | CYTH4 | ELP4 | E4F1 |
| LZTS2 | TRMT10A | QARS | PLXDC1 | CYTH3 | ANKMY2 | ATAD3B |
| MACF1 | FOXN2 | PXK | PLK3 | BCAS3 | ELOVL5 | DLAT |
| LYAR | FOXO4 | PXDN | SND1 | CYTH1 | ELL3 | APEX2 |
| TAF3 | FOXP1 | PWWP2B | PLOD1 | USP21 | ANKRD10 | DLG5 |
| LYPLAL1 | TRIP6 | PUM1 | PLOD2 | BCCIP | ELOF1 | EDC3 |
| LRRK2 | TRIP4 | PUM2 | SNAPIN | BCKDHA | ELMSAN1 | AP3B1 |
| LRRK1 | FOXJ2 | PURB | PLRG1 | BCKDHB | ELMO2 | EDF1 |
| LRPAP1 | TRNAU1AP | PUS7 | PLAC9 | USP20 | ELMO1 | EDEM3 |
| LRP1 | TRMU | PUS7L | PIK3R4 | BAG4 | ZNF619 | ULK3 |
| LRP12 | FOSB | PWP1 | PIK3R5 | BBS1 | ATL3 | EDEM2 |
| TBC1D22B | FOSL2 | PWP2 | PIKFYVE | BAG5 | ENOX2 | APIP |
| TBC1D22A | TRMT6 | PTDSS1 | PIM2 | DAPK1 | ALDH5A1 | UBE2I |
| LRP5 | TRMT5 | SLC7A6 | PISD | BANP | ALDH9A1 | ATAD2B |
| LRPPRC | TRMT2B | PSMA2 | PIN4 | BAP1 | TYW1 | ECHDC2 |
| LRRC14 | FDPS | PSMA4 | PINX1 | USP19 | ALG11 | APAF1 |
| TBC1D15 | FCGR3A | PSMB5 | PIP5K1A | ZNF408 | ALG12 | APBA3 |
| LRMP | FCHO2 | PSMB7 | PIK3R1 | ZNF407 | ALG13 | ECH1 |
| TBC1D23 | FCHSD2 | SLC8B1 | PIK3CB | BASP1 | ALG14 | ATAD2 |
| TBC1D24 | TSHZ1 | SLC9A1 | PIGO | DAGLB | ALG3 | APBB1IP |
| LRIG2 | FES | PRSS23 | PIGQ | BAZ1A | ALG6 | APBB2 |
| LPCAT2 | FDXR | SLFN11 | PIGT | BAZ1B | TYW5 | DLG1 |
| | | | | BAZ2A | | |

TABLE 5-continued

Mutational Burden Genes

| | | | | | | |
|---|---|---|---|---|---|---|
| LPCAT4 | FECH | SLCO3A1 | PIGX | DAG1 | EPG5 | APC |
| LPIN1 | FCGR2A | SLCO2B1 | SNW1 | BAZ2B | EPDR1 | ATAD1 |
| LPIN2 | FCER1G | SLC9B2 | PIH1D1 | CEP95 | EPC2 | ECI1 |
| LPP | FBXO6 | SLC9A8 | PIK3C2A | CEP85L | ALG8 | AP4B1 |
| LPXN | FBXO8 | PRUNE2 | PIK3C2B | CEP78 | EPC1 | DLD |
| LRBA | FBXW11 | SLC9A3R1 | PIK3C3 | CEP70 | ALDH4A1 | ZNF565 |
| LRCH1 | FBXW9 | PSD4 | PIK3CA | CEP57L1 | EPHB4 | DLG4 |
| LRCH3 | TRPM7 | PSEN2 | PKM | CEP57 | AKT3 | ECD |
| LRCH4 | FGFRL1 | PSTPIP1 | PKN1 | CEP41 | EPS15L1 | ECE1 |
| TBC1D2B | FGGY | PSMF1 | PKNOX1 | CEP350 | EPRS | DLG3 |
| LRIF1 | TRPT1 | PSMG1 | PKP4 | WWP2 | TYK2 | UMPS |
| LRRC28 | FGR | PSMG4 | PLA2G4A | CEP250 | ZNF668 | APMAP |
| TARSL2 | FHL2 | PSPC1 | PLA2G6 | CEP192 | EPOR | AP1B1 |
| TARS2 | FHOD1 | PSPH | PITPNB | CEP170 | EPN2 | EEF1G |
| TARDBP | FICD | PTBP1 | PITPNC1 | CEP135 | EPHB6 | EEF1A1 |
| TARBP1 | FIG4 | PTBP2 | PITPNM1 | CBWD3 | ALCAM | EEF2K |
| TAPT1 | FIP1L1 | PTCD1 | SNTB1 | CEP89 | ALDH16A1 | DIS3L2 |
| LRRC8A | FGFR1 | PTCD3 | SNRPN | CBFA2T2 | EPN1 | AP1M1 |
| LRRC8B | TRRAP | PTCH1 | PKD1 | CBL | EPM2A | DZIP3 |
| LRRCC1 | FEZ2 | PSME4 | PKDCC | CBLB | ALDH1A1 | EEF1D |
| LRRFIP1 | FGD2 | PSME2 | PNISR | CBLL1 | ALKBH1 | EEF2 |
| LRRFIP2 | FGD3 | PSMC6 | PPAN | WWC3 | U2SURP | UNC45A |
| LRRC61 | FGD6 | PSMD12 | PPARA | CES4A | ZNF638 | DIRC2 |
| LRRC32 | TSC22D1 | PSMD3 | PPARG | ZBTB5 | ENTPD6 | ZNF559 |
| LRRC37B | TSC2 | PSMD5 | PPFIA1 | CES2 | ALS2 | UNC13D |
| TBC1D10B | TSC1 | RIC8A | PPFIBP1 | CES1 | ENTPD1 | ULK1 |
| TBC1D10A | FPGT | SAV1 | PPFIBP2 | CERS6 | ZNF627 | AP2M1 |
| TBC1D1 | GALM | SART1 | PPIA | WWOX | AMBRA1 | ULK2 |
| TAX1BP1 | GALNS | SATB1 | POU6F1 | WWP1 | ZNF626 | DIS3 |
| TATDN2 | GALNT10 | SHOC2 | SMPD4 | WRNIP1 | AMFR | ASUN |
| LARS2 | GALNT2 | SBF1 | POP4 | XAF1 | ZNF623 | EED |
| TIMELESS | GALT | SBF2 | POR | ZBTB43 | ENPP4 | AP2A2 |
| KHNYN | GANAB | SHKBP1 | SMOX | CCDC146 | AMN1 | EEA1 |
| KHSRP | GANC | SBNO1 | POU2F1 | XIAP | AMPD2 | DLGAP4 |
| KIAA0100 | TRIP12 | SAFB | PPP1CC | CECR5 | AMPD3 | AP1AR |
| KIAA0141 | TRIM22 | SAFB2 | PPP1R12A | CCDC149 | ENTPD7 | CCDC68 |
| KIAA0196 | TRIM16 | SHPRH | PPP1R13B | CECR1 | ALKBH3 | ASS1 |
| KDM6B | TRIM14 | SAMD9L | PPP1R15A | ZBTB40 | EP400NL | ZNF813 |
| KDM5C | TRIM11 | SAMHD1 | PPP1CB | ZBTB4 | ALKBH4 | ZSCAN12 |
| KIF3A | GAK | SAMM50 | PPIL2 | ZBTB39 | ALKBH5 | PRICKLE3 |
| KCTD9 | TRAPPC9 | SAP130 | PPIP5K1 | ZBTB38 | EPB41L3 | ZNF471 |
| KDM1A | TRAPPC3 | SBNO2 | PPIP5K2 | CEP104 | EPB41L2 | NOSTRIN |
| KDM2A | GAPVD1 | SH3RF1 | PPM1B | CBX5 | ZNF655 | A4GALT |
| KDM5B | GCC1 | SCMH1 | PPM1L | CBX6 | ALMS1 | ZRANB3 |
| KDM2B | GBP2 | SCML1 | PPM1M | CENPQ | EPB41 | PPP1R26 |
| KDM3B | TRAPPC12 | SH3TC1 | POMT2 | CBX7 | EPAS1 | ABHD6 |
| KDM4A | TRAPPC10 | SCN1B | POMT1 | CBY1 | ALOX5 | CBS |
| KDM4B | GCAT | SH3RF3 | POMP | CC2D1A | EP400 | CD248 |
| KDM4C | GCC2 | SCAF1 | POGZ | CC2D1B | EP300 | NFASC |
| KDM5A | TRAP1 | SH3KBP1 | POLA1 | ZBTB48 | ALOX5AP | SEMA5A |
| KIAA0232 | TRANK1 | SCO1 | POLD1 | CCAR1 | EOGT | CD300A |
| KIAA0355 | GBF1 | SCP2 | POLK | CCAR2 | ALPK1 | ABI3BP |
| TIE1 | GBE1 | SCPEP1 | POLE | CENPC | ZNF641 | NES |
| KIAA1715 | GART | SHB | POLH | CCDC109B | FADS2 | CD2 |
| KIDINS220 | GAS2L1 | SCAF4 | POC5 | CCDC115 | FADS3 | NOTCH3 |
| KIF13A | GAS6 | SCAF8 | SMYD3 | XAB2 | AC138035.2 | STAG3 |
| KIF13B | GATAD2A | SCAP | POC1B | WSB1 | AC009403.2 | SLC7A5 |
| KIAA0368 | GATAD2B | SCAPER | SNAP29 | WRN | ZRANB2 | ACSM3 |
| KIF1B | GATM | SCARB2 | SMYD5 | CAPS | AC013461.1 | ZAP70 |
| KIF1C | GBA | SCD | PNPLA6 | CHKA | ZNFX1 | PTPRU |
| KIF22 | TRIM24 | SCFD2 | PNPLA8 | CHID1 | ZNF91 | ABLIM3 |
| TICAM1 | FTSJ3 | SAAL1 | POLI | WHSC1L1 | FAM73B | CCDC80 |
| TIAM2 | TRIM5 | S1PR3 | POLL | ZC3HAV1 | FAM73A | SEMA3C |
| TIAM1 | TRIM44 | RSBN1L | POLR2M | CAPZA2 | ZNF880 | SEMA4A |
| KIAA1586 | FTO | RSF1 | POLR3A | ZC3H7B | ZNF862 | AC005943.2 |
| KIAA1551 | FUBP1 | SIK3 | POLR3B | CARD16 | ZSCAN21 | PPP1R13L |
| KIAA1468 | FUK | SIK1 | POLR3C | CHFR | ABLIM1 | SGCE |
| KIAA0391 | FURIN | RSPRY1 | POLR3D | ZC3H7A | FANCC | ABI3 |
| KIAA0430 | TRIM52 | RRP9 | POLR3E | ZC3H6 | ABI2 | NFIB |
| KIAA0556 | TRIM56 | RRP8 | POLM | CHD9 | ABL1 | NCKAP1L |
| KIAA0586 | FRA10AC1 | RRP36 | POLRMT | CHD8 | FANCA | SEMA6D |
| KIAA0753 | TRIP11 | RRBP1 | POM121 | CHD7 | FAN1 | SFRP1 |
| KIAA0922 | FRG1 | RREB1 | SMURF1 | CHD6 | TSPAN7 | SASH1 |
| KIAA1109 | TRIOBP | RRM2B | SMU1 | CARD6 | ABL2 | PPP1R16B |
| KIAA1191 | FRMD4B | RRP1B | SMTN | CHD4 | FAM98C | SASH3 |
| KIAA1324L | TRIO | S1PR1 | SMYD2 | CHD3 | FAM98B | PTPRG |
| KIAA1328 | FRY | RXRA | POLR1B | CHD1L | FAM98A | NCEH1 |
| KAT6B | FRYL | RYBP | POLR2A | CHM | ZSCAN25 | SH3BP4 |

TABLE 5-continued

Mutational Burden Genes

| | | | | | | |
|---|---|---|---|---|---|---|
| KANSL2 | TRIM68 | SIGIRR | POLR2B | CAPRIN2 | ABR | PTPRB |
| KANSL3 | FUS | S100A10 | POLR2E | CAND1 | ZSCAN30 | AXL |
| KAT2B | TRIM34 | SIAH2 | POLR2F | CHMP4B | FAM84B | PTN |
| KAT6A | GAA | S100A8 | POLR2G | CAPG | ABRACL | SLC9A3R2 |
| KAT7 | TRIM41 | RTEL1 | PCF11 | ZCCHC11 | ABT1 | ACE |
| KBTBD6 | G3BP1 | RTF1 | SOS1 | CAPN15 | ABTB1 | SH3PXD2B |
| KAT8 | G2E3 | RTN3 | SORT1 | CAPN3 | TSR1 | NMNAT3 |
| KATNB1 | FUT8 | RTTN | SORL1 | CAPN5 | ZNF844 | PRDM1 |
| KATNBL1 | FYB | RUFY1 | SORBS3 | CAPN7 | ACER3 | PTAFR |
| KBTBD3 | FYCO1 | RUFY2 | SORBS1 | ZC3HC1 | ACADVL | CCDC122 |
| KANSL1 | FYN | RUNDC1 | SON | CHML | FAM47E | PSTPIP2 |
| KANK2 | FZD1 | RUSC1 | PCGF5 | CARD8 | TTBK2 | ZNF441 |
| JMJD6 | GTF2IRD2B | RUSC2 | PCIF1 | CASP10 | ZNF841 | CCDC121 |
| TM9SF4 | TMEM173 | RUVBL1 | SOS2 | ZC3H13 | TTC13 | NEDD4 |
| JUNB | TMEM168 | RUVBL2 | SOCS2 | WLS | ACAP1 | B3GALNT1 |
| JUND | TMEM167B | SCRIB | PBRM1 | CFLAR | ACAP2 | ZBTB45 |
| JUP | IGHMBP2 | SGPL1 | PBXIP1 | CFL2 | ACAP3 | ATP8B4 |
| KANK1 | IGF2R | SGTA | PC | CFL1 | FAM46A | SERAC1 |
| KBTBD7 | TMEM165 | SGSM2 | PCBP2 | CASP4 | ACAT1 | ZNF429 |
| TIMM50 | TMEM161A | SGSH | PCBP1 | WNK1 | ACAT2 | NINL |
| TIMP1 | TMEM175 | SERPINB6 | SP1 | CASP6 | ACBD3 | CCND1 |
| KCTD10 | TMEM176A | SERPINB8 | PCCA | CASP9 | ACBD4 | SLC9A9 |
| KCMF1 | ILVBL | SGPP1 | PCCB | ZC3H11A | ACBD5 | SERINC2 |
| KCTD13 | IFRD2 | SERPING1 | PCDH1 | ZC3H10 | FAM35A | ATXN7L2 |
| KCTD18 | IFT122 | SERPINH1 | SP2 | CAST | TTC17 | PTGER4 |
| KCNAB2 | IFT140 | SERPINI1 | SP140L | CAT | ACCS | SERPINA3 |
| TLR4 | IFT172 | SERTAD1 | SP110 | CATSPER2 | ACD | PRKD1 |
| TLR1 | TMEM176B | SESN1 | SP100 | ZBTB7B | FAM49A | ZNF431 |
| TLN1 | IFT88 | SEPT2 | PDCD6IP | WRAP73 | ACAD11 | ASAP3 |
| TLK2 | IGF1R | SEPT5 | SOCS5 | WIZ | AC138969.4 | PTGFRN |
| TLK1 | IKBKAP | SEPT7 | PDE2A | ZC3H14 | TSSC1 | AVIL |
| TLE4 | IKZF1 | SEPT9 | PDE4DIP | CARF | TSSC4 | PTGR2 |
| TLE3 | TMEM131 | SH2D3C | PDE5A | CARHSP1 | ACAA1 | PTGS1 |
| TJP2 | IL2RG | SERINC3 | PDE7A | WIPF2 | ACAA2 | ABCC9 |
| KRT8 | IL32 | SERPINA1 | PDE8A | CHAMP1 | TST | PPP4R1L |
| TFPI | IL4R | SF3B4 | PDGFC | CHAF1A | TSTA3 | SMARCA1 |
| TFEB | ILF3 | SFI1 | PCNT | ZC3H4 | ACACB | SHC2 |
| TFDP1 | IL1R1 | SFMBT1 | PCOLCE2 | CARS | ACAD10 | ABCA6 |
| TFCP2 | IL10RA | SFPQ | PCSK7 | CARS2 | FAM65B | PROCR |
| TFAP4 | IL13RA1 | SFSWAP | PCYT1A | ZC3H3 | ACAD8 | CC2D2A |
| TIA1 | IL15RA | SFT2D2 | SOCS6 | ZC3H18 | ACAD9 | SLIT2 |
| KPNA3 | IL16 | SET | PDCD11 | ZC3H15 | ACADM | SCUBE2 |
| KPNA4 | IL17RA | SGK3 | PAXIP1 | CASC4 | TSTD1 | PROS1 |
| TGIF2 | IL17RC | SGK1 | PAXBP1 | CASK | FAM53C | SGK494 |
| KPTN | TMEM144 | SFXN2 | PAFAH1B2 | SPATA13 | ZBTB34 | SCARA3 |
| KRCC1 | IFNGR2 | SFXN5 | PAN2 | CHMP7 | ACADSB | AASS |
| TGIF1 | IFNGR1 | SF3B3 | PAK2 | CDC34 | TSTD2 | SLIT3 |
| KRIT1 | IARS | SF3B2 | SPAG9 | CDC27 | ABI1 | PPP1R3D |
| TGFBRAP1 | HUWE1 | SF3B1 | PALB2 | YBX1 | ABHD8 | PPP1R3C |
| KRT10 | HYOU1 | SF3A3 | PAM | CCNK | ABHD5 | SEPT10 |
| TGFBR3 | IARS2 | SETD1A | P4HA1 | CDC25B | ABHD4 | ACOX2 |
| KSR1 | IBA57 | SETD1B | P4HA2 | CCP110 | AARS | SLC8A1 |
| KTN1 | ICA1 | SETD2 | PABPC1L | CDAN1 | AARS2 | ZNF827 |
| LARP1 | TMEM184B | SETD3 | PACS1 | CDC40 | AARSD1 | ABCA7 |
| LARP7 | HTT | SETD5 | PACSIN2 | CDCA7L | FBXL20 | SHF |
| LAMC1 | HTRA2 | SETD6 | PAN3 | YTHDF2 | AASDH | ATP8B1 |
| TEX10 | HSPG2 | SETD7 | PARP12 | YTHDC2 | AASDHPPT | CCR1 |
| LAMB2 | HTATSF1 | SETDB1 | PARP14 | CDC5L | ABAT | ZNF845 |
| LAMB1 | TMEM206 | SETDB2 | PARP3 | CCNB1 | ABCA1 | PSD3 |
| L2HGDH | TMEM2 | SETX | PARP4 | CDC42EP4 | ABCA2 | ZNF852 |
| L3MBTL2 | TMEM192 | SGMS1 | PARP6 | CDC42EP3 | ABCA5 | ZNF443 |
| LACTB | IFNAR2 | SF3A1 | PARP8 | CCND2 | FBXL19 | SETBP1 |
| LAIR1 | IFIH1 | SF3A2 | PARVB | CDC42BPB | ABCB1 | SLC7A2 |
| TEX2 | IFI27L1 | SH3BGRL2 | PARVG | CDC42BPA | ABCB10 | ZBTB46 |
| LAMA5 | IFI30 | SDPR | SPAG16 | CD99L2 | FBXL14 | SCD5 |
| KPNA1 | IFIT2 | SH3BP5L | PASK | CD55 | FBXL12 | STARD8 |
| KNTC1 | IFITM3 | SEC11A | PATL1 | CCZ1B | FBRS | STARD13 |
| KLHDC3 | IFNAR1 | SEC14L1 | PAWR | CD47 | ZW10 | CCDC3 |
| KLF6 | IDS | SEC24B | PARP10 | CD44 | ABCB6 | CCDC102B |
| KLF7 | HSPBAP1 | SH3BP5 | PANK4 | CD14 | ABCB7 | NDN |
| KLF9 | TMCO3 | SH3BP2 | PAPD5 | CD40 | ABCB8 | SH3D19 |
| KLHL18 | ISOC1 | SEC16A | PAPLN | CD4 | FBXL6 | ABCA8 |
| THOC5 | TMCC3 | SEC23A | PAPOLG | CD163 | FBXO25 | SPAG1 |
| THOC2 | ISY1 | SEC23B | PAPSS2 | YIPF3 | A2M | BTNL9 |
| KIF9 | ITFG1 | SEC23IP | PARL | CD36 | FBXO38 | PARVA |
| KIFAP3 | ITFG2 | SCYL1 | PHC1 | YIF1A | ZZEF1 | ALDH7A1 |
| KIFC2 | ITGA5 | SDAD1 | PHC2 | CD302 | AAAS | PARD3B |
| THUMPD3 | ITGA7 | SDCBP | PHF10 | CD2AP | FBXO28 | PARD3 |

TABLE 5-continued

Mutational Burden Genes

| | | | | | | |
|---|---|---|---|---|---|---|
| KLC1 | ITGAE | SDCCAG8 | PHF12 | YES1 | AACS | RBM47 |
| KLC2 | ITGAL | SEC24C | PHB | CD93 | ZYX | C3 |
| KLC4 | ITGAM | SEMA3F | PHF2 | CD9 | TSPAN14 | C3AR1 |
| THRAP3 | TMCO4 | SEMA6A | PHF20 | YLPM1 | ZXDB | ROBO1 |
| KLHL2 | IRF2BPL | SEMA6C | PHF20L1 | CD86 | FBXO22 | C3orf33 |
| KNSTRN | IRF3 | SENP1 | PHF23 | CD83 | FBXO18 | PIK3AP1 |
| TGS1 | IRF8 | SEC24D | SNX14 | CD82 | AAED1 | PID1 |
| THAP4 | TMED4 | SENP5 | PGM1 | YBX3 | FBXO11 | PCDHGC3 |
| THADA | TMED1 | SENP7 | PGD | CD74 | AAGAB | ZNF283 |
| KMT2A | ISG15 | SEPP1 | PGGT1B | CCSER2 | AAK1 | SORBS2 |
| KMT2C | ITGAX | SEC31A | SNX17 | CCT2 | AAMDC | SLC38A5 |
| KMT2D | ITGB1 | SEC31B | PGRMC2 | CCT3 | AAMP | C10orf128 |
| KMT2E | JAG1 | SEC61G | PHACTR2 | CCT4 | ZXDC | ZNF14 |
| TGOLN2 | IWS1 | SECISBP2 | PHF3 | CD63 | AAR2 | SOX13 |
| THBD | JAK2 | SEL1L3 | PI4K2A | YIPF6 | ABCC1 | SOX7 |
| KLHL21 | TMA16 | RIC8B | PI4KA | ZBTB14 | TSPAN3 | RBP1 |
| KLHL22 | JARID2 | RNF8 | PIAS4 | CDKN2AIPNL | FBN1 | ZNF135 |
| THEM4 | IVD | RNGTT | PICALM | CDKN2AIP | FASN | PBLD |
| KLHL5 | ITSN2 | RNH1 | PICK1 | CCDC28A | FARSB | SLC39A14 |
| KLHL7 | ITSN1 | RNMT | PIGC | XPR1 | ABHD13 | PALMD |
| THBS1 | ITGB2 | RNPC3 | PIGG | XRCC1 | FARSA | NPAS2 |
| MAD1L1 | ITGB4 | ROBO3 | PHYKPL | ZBTB11 | ABHD14A | SLC25A23 |
| MRPL1 | ITIH4 | ROCK2 | PHYHD1 | CDKAL1 | FARS2 | ZNF555 |
| STYXL1 | ITM2A | SLC25A39 | PHYH | CDK8 | ZSCAN31 | RASAL2 |
| MRPL10 | ITPKB | RNF214 | PHGDH | ZBTB10 | ABHD14B | P2RX7 |
| SUCLG2 | ITPR1 | RNF217 | SNX13 | ZBTB1 | ABHD11 | ZNF554 |
| MPP5 | ITPR2 | RNF34 | PHIP | CDK5RAP3 | ABHD15 | RARRES2 |
| MPP6 | ITPRIP | RNF38 | PHKA2 | CDK5RAP2 | ABHD16A | SPDYE3 |
| MPP7 | IRF2 | RNF4 | PHKB | CDK5RAP1 | ABHD17A | RARG |
| SUCO | INPP5A | RNF40 | PHLDB2 | CCDC22 | ABHD17B | OTUD3 |
| MPST | INO80 | RP11-231C14.4 | PHLPP1 | CCDC57 | ABHD17C | PLCB1 |
| MPZL1 | INO80C | RP11-166B2.1 | PHLPP2 | ZBTB25 | ABHD18 | SLC22A17 |
| MR1 | INO80D | SLC24A1 | PHOSPHO2 | ZBTB24 | ABHD2 | SLC1A3 |
| MRAS | INPP5B | SLC22A23 | PHRF1 | XPNPEP1 | ABHD3 | PALLD |
| MRC2 | INPP5D | SLC22A18 | PGBD2 | ZBTB21 | ABHD12 | PALD1 |
| MRE11A | INPPL1 | SLC25A36 | PGAP3 | XPO1 | ABHD10 | APCDD1 |
| MRPL54 | TMEM109 | SLC1A5 | PDXDC1 | XPO5 | ABCC10 | ZNF322 |
| MRPL33 | IMP4 | SLC25A13 | PDZD8 | XPO6 | ABCD4 | SPARCL1 |
| MRPL35 | IMPA2 | SLC25A14 | PEAK1 | XPO7 | FBLN5 | SLC25A33 |
| MRPL38 | IMPACT | SLC25A32 | PEAR1 | ZBTB17 | ZSWIM8 | PKN3 |
| MRPL39 | INCENP | SLC25A26 | PEBP1 | CDR2 | ZSWIM6 | RBFOX2 |
| MPHOSPH6 | INF2 | SLC25A16 | PECR | ZBTB16 | ABCC3 | RAVER2 |
| MLLT3 | ING3 | RNF213 | PELP1 | CCDC71 | ABCC5 | RCAN2 |
| MLLT4 | ING4 | RLF | PDS5B | CCDC88B | ABCD1 | AOC3 |
| SUN1 | IPO8 | RLIM | PDS5A | CCDC88C | ABCD3 | PGM5 |
| MLXIP | IPO9 | SLC29A3 | PDIA4 | CCDC9 | ZSCAN9 | ZNF248 |
| MMAA | IQCB1 | RMDN3 | PDIK1L | CCDC91 | ABCE1 | RHBDF1 |
| MLLT1 | IQCE | RMI1 | PDK4 | CCDC92 | ABCF1 | ZNF205 |
| MMD | IQCG | SLC29A1 | PDLIM5 | CCDC93 | ABCF2 | PHACTR1 |
| SUMO3 | IQCK | SLC27A4 | PDPR | CCDC94 | ABCF3 | C1orf112 |
| SUMF2 | IQGAP1 | SLC2A11 | PEMT | CCDC97 | ABCG1 | PDGFRB |
| SUMF1 | IQGAP2 | RICTOR | PER1 | XRN1 | FASTKD3 | ANK3 |
| SUPT20H | IQSEC1 | RIF1 | SNX3 | CDK4 | FASTKD2 | PDGFRA |
| MKL1 | IRAK1 | RIMKLB | PFKFB2 | CCDC69 | ZSWIM4 | ZNF582 |
| MKL2 | IREB2 | SLC2A3 | PFKFB3 | CDK2AP2 | FASTKD1 | PDE9A |
| MKLN1 | IPO7 | RIN2 | PFKP | CCDC61 | ZSWIM1 | RGS5 |
| MKS1 | IPO5 | RIN3 | PER2 | CDK19 | TTC21B | RFX3 |
| SUOX | IPO4 | RIOK1 | SNX29 | CDK18 | TUBA1B | ZNF570 |
| SUN2 | IPO13 | RNF2 | SNX25 | CDK14 | ADAR | RGL1 |
| MLF1 | INSR | SLC26A2 | PFAS | ZBED5 | ADARB1 | RGL3 |
| MLH1 | INTS1 | SLC26A11 | SNX30 | CDK13 | ADAT1 | PEX11A |
| MMS19 | INTS10 | RNASEL | PEX7 | CDK12 | ADCK1 | ZNF223 |
| SUGP2 | INTS12 | RNF185 | PES1 | CCDC66 | FAM13A | ZNF232 |
| MORC2 | INTS3 | RNF14 | PET117 | CDK11A | TUBA1C | ZNF235 |
| MORF4L1 | INTS4 | RNASET2 | PEX1 | CDIPT | FAM135A | PER3 |
| MOV10 | INTS7 | RNF103 | PEX11B | CAMTA2 | ADCK3 | ZNF599 |
| SUFU | IP6K1 | SLC27A3 | PEX19 | CAMTA1 | FAM134A | ZNF600 |
| MON2 | IP6K2 | RNF111 | PEX5 | CNTROB | FAM133B | PELI3 |
| MOK | IPO11 | RNF13 | PEX6 | WASF2 | ADCY3 | PDZRN3 |
| MNAT1 | HSPBP1 | RNF130 | FBXO42 | C3orf58 | ZNF765 | ANK2 |
| MNDA | HEATR5B | RNF135 | HIF1AN | ZMIZ2 | ZNF777 | SLC30A4 |
| MOB1B | HDHD3 | RNF138 | BTBD7 | ZMIZ1 | ADAM15 | ZNF273 |
| MOCS2 | HDLBP | SLC18B1 | CTC1 | WASH4P | TTLL4 | AMOTL2 |
| SULF2 | HEATR5A | RPL8 | BTD | ZMAT1 | TTLL5 | ZNF169 |
| MOGS | HEATR6 | RPN1 | ZNF302 | ZKSCAN8 | ZNF778 | SLC38A1 |
| MTMR12 | HECA | RPN2 | VAV2 | C4orf3 | TTYH3 | ANPEP |

TABLE 5-continued

Mutational Burden Genes

| | | | | | | |
|---|---|---|---|---|---|---|
| MTMR14 | HECTD1 | RPL7A | CTBP2 | C4orf33 | ADAM28 | RNASE4 |
| MTMR4 | HECTD3 | RPP38 | BTN3A1 | WBP11 | FAM160B1 | PHLDB1 |
| MTMR6 | HECTD4 | RPRD1B | VCAM1 | CNST | ADAM9 | RCSD1 |
| MTO1 | HEG1 | RPRD2 | ZNF304 | ZKSCAN5 | FAM160A2 | ALS2CL |
| MTMR10 | HDAC9 | SIN3B | ZNF317 | CNTRL | ADCY4 | SNX10 |
| MTOR | HIPK1 | SIN3A | BROX | ZMYM4 | ACIN1 | ALPL |
| MTPAP | HCFC1 | RPL7L1 | BRPF1 | WARS2 | FAM129B | RNF144A |
| MTRR | HCFC2 | SLC18A2 | BRPF3 | WAS | ZNF721 | ANGPTL2 |
| MTMR11 | HCK | SIPA1 | BRWD1 | COIL | FAM107B | PDE4B |
| MTMR1 | HCLS1 | RPL5 | BRWD3 | ZMYM3 | ADH5 | PDE4A |
| MTF2 | HDAC8 | RPS10 | ZNF319 | COG4 | FAM105A | PDE1B |
| MTFP1 | HDAC4 | RPS6KA1 | BTAF1 | COG3 | ADHFE1 | SLC35F2 |
| MTFR1 | HDAC6 | RPS6KA2 | ZNF318 | ZMYM2 | FAM102A | RERG |
| MTM1 | HDAC7 | RPS6KA3 | CTAGE5 | COASY | TUBB6 | REPS2 |
| MTHFD2L | HELZ | RPS6KA4 | ZNF28 | ZMPSTE24 | ADIPOR1 | ANO8 |
| MTHFR | TMEM67 | RPS6KB1 | CSTF1 | ZKSCAN1 | FAHD2A | ANKS6 |
| MTIF2 | TMEM69 | RPS6KC1 | VIM | WDFY1 | ADIPOR2 | SLC35G1 |
| MTSS1L | HIBADH | SIMC1 | C11orf49 | ZFYVE26 | ZNF746 | ZNF618 |
| MVK | HID1 | RPTOR | ZNF275 | C6orf120 | ADD3 | REEP6 |
| MVP | HIGD1A | RPS3 | CSRP1 | WDFY3 | FAM129A | SLC2A10 |
| MX1 | HELZ2 | RPS27L | CSRNP2 | ZFYVE16 | ADCY7 | SLC41A2 |
| MYADM | HIGD2A | RPS15 | ZNF280D | CMTR2 | FAM126A | C7 |
| MTX1 | HINFP | RPS15A | VCP | CMTR1 | ADD1 | RPS6KL1 |
| STRA13 | HINT2 | SLAIN1 | BUD13 | C6orf203 | FAM120B | NTN4 |
| MYBBP1A | HIP1 | SLA | BZW2 | ZFYVE1 | FAM120AOS | CAMSAP2 |
| MYCBP2 | HEMK1 | SIRT3 | C10orf10 | C6orf226 | FAM118B | BCAT1 |
| STOML2 | HERC1 | SKI | ZNF292 | ZFX | FAM118A | ZNF521 |
| MUTYH | HERC2 | RP2 | ZNF286A | CMTM3 | FAM117A | ZNF763 |
| MTX3 | HERC3 | SIRT7 | VGLL4 | WDPCP | FAM111A | ZC4H2 |
| STUB1 | HERC5 | SLC16A3 | C10orf54 | C5orf42 | ZNF821 | BCAR1 |
| STT3A | HERC6 | SLC12A9 | ZNF282 | CNOT6L | TTC3 | PORCN |
| STRN4 | HERPUD2 | SLC12A7 | BRIX1 | CNOT6 | ZNF816 | ADAMTSL4 |
| STRN3 | TMEM99 | SLC12A6 | CUTC | CNOT4 | ACSF2 | ADAMTSL3 |
| STRIP1 | GUF1 | SLC12A4 | CUL9 | CNOT3 | ACSF3 | ADAMTS9 |
| STRBP | GUSB | SLC12A2 | CUL7 | ZHX3 | FAM216A | RSAD2 |
| STRADB | GXYLT1 | SLC10A7 | CUL5 | ZHX2 | ACSL1 | ADAMTS2 |
| MUS81 | TMX2 | SLC10A3 | CUL4B | CNOT10 | FAM214B | NRSN2 |
| MUT | TMX1 | SIRT1 | CUL4A | CNOT1 | FAM214A | BCL6B |
| MS4A6A | GYS1 | RPL22 | CUL3 | CNN2 | ACSL3 | PODXL |
| STXBP5 | GZF1 | SIPA1L1 | CUL1 | ZMYND11 | FAM210B | NUDT13 |
| STXBP4 | TMX4 | RPL10A | CUEDC2 | COPS7A | FAM210A | ZDHHC11 |
| STXBP3 | GTF3C1 | RPA1 | UTP6 | COPS4 | ACSL4 | ZDHHC1 |
| STXBP2 | GTF3C3 | RPA3 | UTRN | COPRS | ACSL5 | CALCRL |
| STX8 | GTF3C4 | RPAP1 | BPGM | COPG2 | FAM208B | ARHGEF19 |
| STX4 | GTPBP1 | RPAP2 | UVRAG | COPA | FAM208A | ARHGEF25 |
| MSH2 | GTPBP10 | RPE | BPHL | COQ2 | FAM206A | ZNF74 |
| MSH3 | GTPBP2 | RPF1 | ZNF33B | COMMD8 | ZNF808 | RAB11FIP5 |
| MRPS9 | GTPBP3 | RPGR | ZNF33A | ZNF175 | ZNF823 | BCO2 |
| MRPS23 | TNFAIP3 | SIPA1L2 | CUX1 | C1orf35 | ACP6 | ZNF77 |
| MRPS27 | TNFAIP2 | RPH3AL | ZNF335 | COTL1 | FAM222B | NRP2 |
| MRPS31 | TNFAIP1 | RPIA | BMP2K | C1orf50 | ACKR3 | ADAMTS10 |
| MRPS5 | H2AFY | PPP1R3B | ZNF350 | CORO1C | ACLY | NPR2 |
| MSH6 | HAUS1 | NRIP1 | UTP14C | CORO1A | ACO1 | NPNT |
| MTDH | HAUS3 | NRP1 | ZNF35 | ZNF17 | ACO2 | ZC3H12A |
| MT-ND6 | HAUS4 | NSDHL | UTP18 | ZNF160 | ACOT1 | ZNF786 |
| MTA1 | HAUS6 | NSFL1C | BMS1 | COQ5 | FAM227B | ZBTB8A |
| MTA2 | HBB | NSMAF | CXCL12 | C1QA | ACOT13 | NPHP4 |
| MT-ND3 | TMPO | NRDE2 | BNIP2 | C1QB | ACOT2 | ARMCX2 |
| MSL1 | HARS2 | NR1D2 | BNIP3L | COL18A1 | ACOT7 | SAMD4A |
| MSL3 | HARS | NR1H3 | BOD1L1 | C21orf59 | ACP5 | SAMD9 |
| MSRB1 | H2AFZ | SRRM2 | ZNF343 | ZNF124 | ACOT8 | ACTG2 |
| MST1 | H6PD | SRRM1 | UTP2O | ZNF121 | ACOT9 | ZNF783 |
| MSTO1 | HACE1 | NR2C1 | CWF19L2 | ZNF117 | TTC27 | SMOC2 |
| MT-ATP6 | HACL1 | NR3C1 | CWF19L1 | C2CD3 | ACOX1 | SMO |
| MT-ATP8 | HADHB | NR4A1 | CWC27 | ZNF106 | FAM220A | CARD10 |
| MT-CO3 | HIP1R | NR4A2 | CWC22 | ZNF101 | FAM21C | RTP4 |
| MT-CYB | HIPK2 | SRR | ZNF337 | VWA9 | FAM21A | ZNF780A |
| MAST4 | TMEM254 | NRAS | CTNNBL1 | C2orf47 | ACOX3 | ZNF780B |
| MARK2 | HP1BP3 | NRBP1 | CTNNB1 | ZNF10 | ACP1 | ACVRL1 |
| MARK3 | TMEM256-PLSCR3 | NSMCE4A | BRD4 | C2orf49 | ACP2 | ZNF41 |
| MARK4 | HPRT1 | NUDC | VAC14 | COL1A2 | ACSS1 | NR3C2 |
| MARS | HPS3 | SRGN | CTNNA1 | COL1A1 | FAM200B | PPIC |
| MAST3 | HPS4 | NUB1 | CTIF | C21orf33 | ZNF785 | CADPS2 |
| MASTL | HRAS | NUBP2 | BRE | COMMD7 | TTF1 | PODN |
| MAT2A | HIPK3 | NUBPL | BRF1 | COMMD3 | TTF2 | PLEKHH2 |
| MATN2 | HNRNPUL2 | NUCB2 | BRF2 | COLGALT1 | TTI1 | C8orf58 |
| MAVS | HOOK3 | NSRP1 | CTDSPL | ZNF142 | FAM179B | RAI14 |

TABLE 5-continued

| Mutational Burden Genes | | | | | | | |
|---|---|---|---|---|---|---|---|
| MAPKAPK2 | TMEM39B | SRI | CTDP1 | C1R | FAM175B | ARAP2 | |
| MAPK7 | TMEM248 | NTPCR | VAMP2 | C1RL | ACVR1B | SPIN3 | |
| MAPK8IP3 | HS1BP3 | NSUN2 | CTNND1 | C1S | FAM173B | SNED1 | |
| MAPKAPK3 | HSP90B1 | NSUN4 | ZNF333 | VWA5A | ACSS2 | SPIRE1 | |
| MARCH7 | TMEM222 | SRP54 | ZNF331 | VWA8 | ZNF789 | BMPR2 | |
| MAPKBP1 | TMEM219 | SRP19 | ZNF329 | COL6A2 | ACTA2 | PLLP | |
| MARCH2 | HSP90AB1 | NR1D1 | BRAF | ZNF134 | ACTB | PLS3 | |
| MARCH6 | HSPA13 | SRRT | CTSF | ZNF133 | ACTG1 | SPRED1 | |
| MBD1 | HSPA5 | NONO | BRAP | CHN2 | TTC37 | ZFHX3 | |
| MCM2 | HSDL2 | NOP56 | CTSC | ZDHHC20 | ACTL6A | OLFML3 | |
| MCCC2 | TMEM241 | NOMO1 | CTSB | ZDHHC17 | FAM199X | RAI2 | |
| SYNCRIP | HSD17B4 | NOS3 | CTSA | ZDHHC16 | ZNF791 | NUP210 | |
| SYMPK | HNRNPK | NOTCH1 | BRAT1 | ZDHHC13 | TTC39B | C8orf44 | |
| SYK | HIVEP2 | NOTCH2 | BRCA1 | WDR77 | TTC39C | OSCP1 | |
| MCM6 | HK1 | NOMO2 | UXS1 | CKAP5 | FAM193B | AIM1 | |
| MCM8 | HLTF | SSRP1 | BRD1 | CACTIN | FAM193A | APOL4 | |
| MCM9 | HLA-DRB1 | NNT | CTR9 | CACUL1 | FAM189B | RAPGEF5 | |
| MCMBP | HIVEP1 | NOA1 | CSRNP1 | CAD | FAM188A | OSBPL7 | |
| MCAM | HIRA | NOB1 | CSPP1 | WDR81 | TTC7A | OSBPL3 | |
| SYNE1 | HIST1H1C | NOC2L | ZNF217 | CALCOCO2 | TTC7B | PLEKHA4 | |
| SYNJ1 | TMEM63B | NOC4L | C19orf47 | ZCWPW1 | EIF5 | PLEKHA7 | |
| MBD4 | TMEM62 | NOD1 | CPVL | CLASP1 | CD2BP2 | RAP1GAP2 | |
| MBD5 | HLCS | NOLC1 | CPT1B | CA5B | ZNF500 | SLAMF8 | |
| MBIP | HMOX2 | NOL10 | CPT1A | ZDHHC8 | ZNF529 | SLAMF7 | |
| SYNGR2 | TMEM45A | NOL6 | CPSF7 | WDR7 | ARHGAP1 | RANBP17 | |
| MBNL1 | TMEM44 | NOL8 | CPSF1 | WDR70 | UGCG | C8orf4 | |
| MBOAT2 | HM13 | NOL9 | CRADD | CLCN7 | ARHGAP10 | PLEKHG4 | |
| MBTPS1 | HNRNPC | SSH1 | CPQ | CLCN6 | ARHGAP12 | AQP3 | |
| MBTPS2 | HNRNPD | SSBP4 | CREBRF | CAB39L | ZNF502 | SPRY4 | |
| SYTL4 | HNRNPDL | NPM3 | CREBBP | CABIN1 | ARHGAP17 | PLVAP | |
| SYTL2 | HMCES | SRSF9 | ZNF224 | CLCN2 | ARHGAP19 | OLFM2 | |
| MAGED2 | HMG20A | SRSF5 | CREB3L2 | CABLES1 | ARHGAP21 | BIN2 | |
| MAN2A1 | HMGB1 | NPIPB3 | C17orf75 | WDR73 | ARHGAP26 | CACHD1 | |
| MALT1 | STOML1 | NPC1 | ZNF222 | WDR74 | ARFIP1 | RAB3D | |
| MAML1 | RAN | NPDC1 | C18orf25 | WDR75 | ARFGEF1 | BICC1 | |
| MAML3 | RANBP10 | NPHP3 | CRAT | CALD1 | APOBEC3G | ZNF708 | |
| MAN1A1 | RANBP2 | NPIPA2 | ZNF211 | CHRNB1 | AREL1 | NUTM2D | |
| MAN1B1 | RANBP6 | ORC3 | CPPED1 | CAMK1 | ARFGAP3 | CACNB1 | |
| SYVN1 | RANBP9 | SPICE1 | VTA1 | CAMK1D | ZNF493 | CACNB3 | |
| SZT2 | RAP1A | SPHK2 | COX6A1P2 | ZCCHC4 | DTX3 | ADORA2A | |
| TAF1 | RALY | ORMDL2 | ZNF180 | WHAMM | ZNF496 | PNPLA7 | |
| TADA3 | RAP1GDS1 | OSBPL10 | C1orf216 | ZCCHC2 | DMXL1 | BHLHB9 | |
| TADA1 | RAPGEF1 | SPNS1 | ZNF207 | CHPF2 | DMXL2 | ADIRF | |
| TACC1 | RAPGEF2 | SPPL3 | ZNF197 | ZCCHC14 | ARHGAP9 | BGN | |
| MAN2A2 | RAPGEF3 | SPRY1 | VPS54 | WHSC1 | UBE2V2 | ZNF704 | |
| MAP3K8 | SLC43A2 | SPRED2 | CPNE8 | WDR82 | ARHGEF10 | NYNRIN | |
| MAP3K13 | RAD52 | OPA1 | C1GALT1 | CHST11 | DNAH1 | PLXNA1 | |
| MAP3K2 | RAD54L2 | SPNS2 | VPS72 | CIC | ARHGEF10L | OGN | |
| MAP3K4 | RAE1 | SPOPL | C1GALT1C1 | CALM2 | ARHGEF11 | PLXNA2 | |
| MAP3K5 | SLC43A3 | SPOP | ZNF202 | ZCRB1 | ARHGEF12 | RAD51AP1 | |
| MAP3K7 | RAF1 | SPON2 | ZNF200 | WDR90 | ZNF507 | SIPA1L3 | |
| MAP4 | RAI1 | SPOCK2 | CPNE2 | ZCCHC6 | EIF4H | PMEPA1 | |
| MAN2B1 | RALBP1 | OTUD5 | VPS8 | CHST15 | DROSHA | ARHGAP25 | |
| MAP4K2 | RALGAPA1 | OTUD6B | CPEB3 | WDR91 | UBE2V1 | ZNF354C | |
| MAP4K4 | RALGAPA2 | SPDL1 | CPEB2 | ZDHHC9 | UFSP2 | ZNF701 | |
| MAP7 | RALGAPB | OSBPL5 | CPD | ZEB1 | ASAP1 | BLNK | |
| MAP7D1 | RALGDS | OXLD1 | VRK3 | C6orf89 | ARHGAP30 | CA2 | |
| MAP3K12 | RAPGEF6 | OXSM | VSIG10 | ZFP64 | ZNF503 | ARHGAP29 | |
| MAP3K1 | RBBP8 | OXSR1 | VPS41 | CLPTM1L | DST | OBSCN | |
| MAN2C1 | RB1 | SPATS2L | CRELD1 | CLPTM1 | UFL1 | SPTLC3 | |
| MANBA | RB1CC1 | SPECC1L | CSK | WDR18 | ARHGAP32 | ARHGAP31 | |
| MANSC1 | RBBP5 | OSBPL8 | VOPP1 | C8orf33 | ARHGAP33 | TLDC1 | |
| MAP1S | RBBP6 | OSBPL9 | C12orf73 | CLNS1A | UBE2R2 | L3MBTL1 | |
| MAP2K1 | RBBP9 | OSMR | VPS13A | CLN6 | ARHGAP35 | CX3CL1 | |
| MAP2K2 | RARA | SPG21 | SPG20 | CLN3 | ZNF528 | UST | |
| MAP2K3 | SLC39A9 | SPG20 | CSF3R | CLK4 | ARVCF | TGM2 | |
| MAP2K4 | RBL1 | SPG11 | VPS13B | CLK2 | ARHGAP4 | CYB561D1 | |
| MAP2K6 | RBL2 | SPEN | VPS13C | CLK1 | ZNF527 | KLRK1 | |
| MCOLN1 | RBM10 | SPEF2 | ZNF250 | CLIP2 | ARHGAP5 | THBS2 | |
| MFSD6 | RBM12 | NUP62 | CSF1R | CLSTN1 | ARCN1 | THNSL1 | |
| MFSD9 | RARS | NUP88 | CSF1 | C7orf26 | ARAP3 | THNSL2 | |
| MFSD1 | RASA2 | NUP93 | CSE1L | C7orf43 | UBE2Q2 | KLHL26 | |
| MGA | RASA4 | NUP98 | VPS13D | CLYBL | DYM | KLHL23 | |
| MGAT4A | SLC40A1 | SRF | CRYZ | CLUH | DVL3 | KLHL17 | |
| MGAT4B | RASGRP3 | SRD5A1 | ZNF253 | CLUAP1 | ASNS | CYP2U1 | |
| MFNG | RASL11A | SREK1 | CSNK2A1 | CLU | DUSP22 | CYP4F12 | |
| METTL25 | RAD51D | SREBF2 | CSNK1E | CLTC | DUSP6 | KIRREL | |
| METTL2A | RAD51B | SREBF1 | CSNK1D | CLSTN3 | APOL2 | CYR61 | |

TABLE 5-continued

Mutational Burden Genes

| | | | | | | |
|---|---|---|---|---|---|---|
| METTL4 | SLC4A1AP | NUP35 | ZNF264 | ZFP91 | APOL3 | LAMA4 |
| METTL6 | RAB18 | NUP214 | C12orf4 | ZFP90 | UBE2J2 | CTTNBP2NL |
| METTL7A | RAD50 | NUDT5 | C12orf43 | CLIP4 | ASPH | LAMB3 |
| SUV39H2 | QSER1 | NUFIP1 | ZNF254 | CLIP1 | DYRK4 | LIMS2 |
| MFAP4 | QSOX1 | NUMA1 | C14orf159 | WDR61 | DLST | LIMCH1 |
| MFF | R3HDM1 | NUMBL | VPS16 | ZFAND4 | DYRK1B | LILRB4 |
| MFHAS1 | R3HDM2 | NUP153 | C16orf58 | CLEC16A | UHMK1 | LILRB2 |
| MGME1 | RAB11FIP1 | NUP155 | C16orf62 | ZFAND3 | DYNLT3 | LIFR |
| MGMT | RAB11FIP2 | NUP160 | ZNF236 | WDR47 | ZNF548 | LGI4 |
| MIER2 | RAB11FIP3 | NUP188 | C16orf72 | C9orf78 | DYNC1LI2 | VCAN |
| MIER3 | RAB3GAP1 | NUP205 | VPS37A | ZFAND1 | DYNC1LI1 | VAV3 |
| SURF1 | RAB3GAP2 | SRD5A3 | VPS37B | ZER1 | DMAP1 | VAV1 |
| MIIP | RAC1 | OCIAD2 | C16orf87 | WDR59 | ASPSCR1 | LEF1 |
| MINA | RAB3IP | OCRL | ZNF23 | ZEB2 | DUSP23 | LDOC1 |
| MINK1 | RACGAP1 | ODC1 | CRNKL1 | WDR6 | ASCC2 | TEAD2 |
| SUPV3L1 | RAD1 | ODF2 | ZNF25 | WDR60 | AQP1 | LDB2 |
| SUPT5H | RAD17 | SPTAN1 | CRYBG3 | WDR44 | UGGT2 | TEF |
| SUPT3H | RABGAP1L | OGDH | C14orf28 | WDR43 | ASH1L | TEK |
| MIA3 | RABGAP1 | OGFOD1 | CRY2 | CLIC4 | ZNF480 | CTH |
| MIB2 | RABEPK | OBSL1 | CRTC2 | CLIC2 | ASF1A | LARP6 |
| MICAL1 | RABEP2 | SRCAP | CRTAP | CLHC1 | UGGT1 | KIF21A |
| MICAL2 | SLC46A3 | NXPE3 | C15orf39 | WDR26 | ASCC3 | DENND5B |
| MICAL3 | RAB40C | SQLE | CROT | CLEC7A | ASCC1 | DDR2 |
| MICALL1 | SLC45A4 | SPTY2D1 | CROCC | WDR27 | ASB8 | KAZN |
| METTL23 | RABEP1 | OAS1 | BMP1 | WDR3 | AQR | KATNAL1 |
| MED10 | RBM12B | OAS3 | CXCR4 | WDR33 | ARAP1 | KALRN |
| MED13 | RBM14 | OAZ2 | DDOST | C9orf142 | ASB7 | JAM2 |
| MED13L | RFTN1 | NMT1 | ZNF436 | WDR35 | UGDH | TMC4 |
| MED14 | RFWD2 | NAT9 | ATP6V1H | ZFC3H1 | APPL2 | ITPRIPL2 |
| MED15 | RFWD3 | NAV1 | ATP7A | WDR37 | APPL1 | ITPR3 |
| MED17 | RFX1 | NAV2 | ATP8A1 | WDR4 | DUSP2 | ITIH5 |
| MED27 | RFX5 | NBAS | ATP9A | ZFAT | DMKN | ITGB7 |
| MED18 | RFX7 | NBEAL1 | DDI2 | DDX18 | DUSP16 | ITGA9 |
| MED19 | SLC35E1 | NBEAL2 | ATP9B | ERN1 | APOL6 | TLR3 |
| MED21 | RGP1 | STAU1 | ATR | AK9 | APOO | ITGA4 |
| MED22 | SLC35B3 | STAT5B | ATRN | AKAP1 | UBE2O | ITGA1 |
| MED23 | SLC35B2 | NCAM1 | ATRX | AKAP11 | ZNF473 | ISLR |
| MED24 | SLC35E2 | STAT3 | DDHD1 | ESF1 | ZNF48 | DHFRL1 |
| MECP2 | REST | NCAPD2 | ATXN1 | AKAP12 | APP | IQSEC2 |
| MCTP1 | SLC35F5 | NCAPD3 | ATP6V0D1 | AKAP13 | DUS4L | INTU |
| MCUR1 | RETSAT | STAT6 | DDX3X | ESCO1 | DUS3L | TM4SF18 |
| MDH1 | REV3L | NAPEPLD | DDX24 | ESAM | UBE3C | KCNE3 |
| MDM1 | REXO1 | NANP | DDX21 | ZNF680 | DOCK5 | KDELC1 |
| MDN1 | RFC1 | NAP1L4 | DDX19A | AKAP2 | DOCK4 | KIAA1958 |
| MDP1 | RFC2 | NAPA | DDX11 | ERV3-1 | UBR4 | DAPK2 |
| ME2 | RFC3 | NAPB | DDX10 | ZNF678 | DOCK2 | TIGD6 |
| ME3 | RFNG | NARF | ATXN2 | AKAP7 | ARL8B | KIAA1217 |
| METAP2 | RGPD8 | NARS | DDX41 | ERP44 | ZNF518B | TIGD7 |
| SVIL | RHOBTB2 | NARS2 | B3GALNT2 | TWISTNB | DNTTIP2 | KIAA0513 |
| MESDC2 | SLC30A6 | NAT10 | DCTPP1 | AK1 | UBR5 | KDR |
| METAP1 | RHOB | NCAPG2 | ZNF420 | AIP | DNPH1 | DCHS1 |
| METTL10 | RHOBTB1 | NCAPH2 | B3GAT3 | AIFM1 | DOCK7 | TLR2 |
| METTL14 | RHOBTB3 | NCBP1 | URB2 | ZNF688 | DOCK8 | TIMP3 |
| METTL17 | SLC35B1 | NCSTN | DCP1B | ZNF687 | DOPEY1 | KCNQ1 |
| MEN1 | RHOG | NDC1 | DCN | ETV6 | DNAJB6 | KCNMA1 |
| MED7 | RHOT1 | NDOR1 | DCLRE1C | ZNF684 | ARL4A | KCNJ8 |
| MEF2A | RHOT2 | STARD5 | DCLRE1A | ETS1 | UBXN2B | TLE2 |
| MEF2D | SLC2A9 | NDUFA10 | URI1 | AIFM2 | UBR3 | TLN2 |
| SWT1 | RHBDF2 | NCOR2 | DCK | ETFA | DOK4 | TCEA3 |
| MEGF6 | RGS12 | NCOR1 | ZNF426 | ETF1 | DOCK9 | INTS2 |
| MEGF8 | RGS14 | NCOA6 | B2M | TWF2 | ZNF516 | TBXAS1 |
| MEGF9 | RGS3 | STAT2 | ATXN2L | ESYT2 | DNMT3A | SYBU |
| JMJD1C | RBMX2 | NCDN | DDB1 | ESYT1 | ARNTL | CLIP3 |
| GMEB1 | SLC39A4 | NCF1 | ZNF432 | AKAP9 | ARMCX4 | MECOM |
| TPD52 | RBM5 | NCF2 | ATXN7 | TXNDC5 | DNMT1 | ME1 |
| TPCN2 | RBMX | NCF4 | ATXN7L1 | ERCC8 | DNAJC3 | CMKLR1 |
| GMDS | RBMXL1 | NCK2 | ATXN7L3 | ERCC6L2 | UBXN2A | CMPK2 |
| GMEB2 | RBPJ | NCKAP5L | AUP1 | ERCC6 | DNAJC21 | MCF2L |
| GMIP | SLC39A3 | NCOA1 | AUTS2 | ERCC5 | DNMBP | CNKSR3 |
| GMNN | SLC39A10 | NCOA2 | AVL9 | ERCC4 | ZNF514 | CNN1 |
| GLTSCR2 | SLC38A9 | NCOA3 | AXIN1 | ERCC2 | DNAJC13 | SYNM |
| GLRX5 | SLC39A6 | NAIP | UROD | TXNL1 | ARMC5 | SYNPO |
| GLS | RBM43 | STK24 | ATP13A1 | ERC1 | DNHD1 | MARCH3 |
| GNA11 | RBM42 | MYO18A | ATP13A3 | ZNF671 | ARPC3 | SYNPO2 |
| TP53I11 | RBM19 | STK3 | DERA | ERBB2 | ARMC9 | MARCH1 |
| TP53BP2 | RBM23 | MYO1D | DEPDC5 | ERAP2 | ARPC2 | CNTLN |
| GNL2 | RBM27 | MYO1F | DENND6A | ERAL1 | ZNF512B | MAPK13 |
| TP53BP1 | RBM28 | STK11IP | ATP2A2 | TXNRD1 | DOPEY2 | MAPK10 |

TABLE 5-continued

Mutational Burden Genes

| | | | | | | |
|---|---|---|---|---|---|---|
| GNPTAB | RBM3 | MYO5A | ATP2A3 | EPT1 | UCHL5 | MAP3K10 |
| GNPTG | RBM33 | MYO5C | ATP2B1 | ERG | ARHGEF6 | CLEC3B |
| GOLGA4 | RBM38 | MYO9A | ZNF440 | ERGIC1 | UBLCP1 | MEIS2 |
| GNG7 | RBM4 | MYO9B | ATP2C1 | AKNA | DPYD | MMRN2 |
| TP53I13 | RECQL5 | MYOF | DENND4C | ERMP1 | ARHGEF40 | MMP2 |
| GNAI2 | RDH5 | MYOM2 | ZNF44 | ERMARD | DPY19L1 | CHN1 |
| GNAI3 | RDX | MYO10 | ATP13A2 | ERMAP | ARHGEF7 | MMACHC |
| GNAS | RECK | MYNN | DENND4A | ERLIN1 | DPP9 | CHPF |
| GNB5 | RECQL | MYH10 | ATP11C | TXNDC11 | ARHGEF9 | CHRD |
| GNG2 | REEP4 | STK4 | ATM | TXNDC12 | ARID1A | WFS1 |
| TPM2 | SLC36A4 | STK39 | ATMIN | ERGIC2 | ARSB | MID2 |
| GFPT1 | SLC36A1 | MYH9 | ATN1 | TXNDC16 | UBN1 | MERTK |
| GET4 | REL | STK38L | DGKE | ERICH1 | UBN2 | CKAP2 |
| TRAF3IP3 | RELA | MYLK | UPF1 | ERI3 | UBQLN1 | SUSD1 |
| GFM1 | SLC38A10 | STK11 | DGKA | ERI2 | UBXN7 | SUSD2 |
| GFM2 | RC3H1 | NACC1 | DGCR8 | AKR1C1 | DPYSL2 | WDR76 |
| TRAF3IP1 | RC3H2 | NAB2 | DGCR2 | AKR1C3 | UBE4A | CKS2 |
| GFOD2 | RCBTB1 | NABP1 | ATP10D | EVA1C | ARSG | WDR5B |
| GGA1 | RCCD1 | NACA | ATP11B | EXTL3 | UBFD1 | CLEC14A |
| GGA2 | RCN1 | NACC2 | UPF2 | F2R | ARHGEF18 | WASF1 |
| GGCX | RCN2 | STK10 | DENND4B | TUBGCP6 | UBL3 | COL12A1 |
| TRAF3 | RCOR1 | NADK | DENND3 | F13A1 | ARHGEF2 | COL14A1 |
| TRAF7 | RCOR3 | NADSYN1 | DEF8 | F11R | UBL4A | TANC2 |
| GDAP1 | PRKX | NAF1 | DECR1 | AFF4 | UBL7 | CPE |
| TRAK2 | SMARCAL1 | NAGLU | DDX60L | EZH1 | DNAJB1 | CPED1 |
| TRAFD1 | SMARCAD1 | STIP1 | DDX60 | AFMID | DPP8 | LRRC8C |
| GEMIN5 | SMARCA4 | MYSM1 | DDX6 | AGA | DOT1L | |

Provided herein are systems and methods for calculating a mutational burden and/or deconvolution of the identities and proportions of cell types in a sample. In some instances, the mutational burden and/or deconvolved cell types are calculated at or above a statistical threshold. The accuracy, specificity, sensitivity, positive predictive value, negative predictive value, or any combination thereof may be determined for an assay for mutational burden and/or deconvolution, for example, by running the assay against a set of independent samples. True positive is a positive test result that detects the condition when the condition is present. True negative is a negative test result that does not detect the condition when the condition is absent. False positive is a test result that detects the condition when the condition is absent. False negative is a test result that does not detect the condition when the condition is present. Accuracy is defined as the sum of true positive and true negative divided by the sum of true positive, true negative, false positive, and false negative. Specificity is defined as true negative divided by the sum of true negative and false positive. Sensitivity is defined as true positive divided by the sum of true positive and false negative. Positive predictive value is defined as true positive divided by true positive and false positive. Negative predictive value is defined as true negative divided by the sum of true negative and false negative.

In some instances, deconvolved cell identities and proportions (of the identities) in a sample are calculated at an accuracy of at least 50%, 60%, 70%, 80%, 90%, 95%, 99% or more. In some instances, deconvolution is calculated at an accuracy of at least 50%, 60%, 70%, 80%, 90%, 95%, 99% or more for at least 100, 200, 300, 400, or 500 or more independent samples. In some instances, deconvolved cell identities and proportions (of the identities) in a sample are calculated at a sensitivity of at least 50%, 60%, 70%, 80%, 90%, 95%, 99% or more. In some instances, deconvolution is calculated at a sensitivity of at least 50%, 60%, 70%, 80%, 90%, 95%, 99% or more for at least 100, 200, 300, 400, or 500 or more independent samples. In some instances, deconvolved cell identities and proportions (of the identities) in a sample are calculated at a specificity of at least 50%, 60%, 70%, 80%, 90%, 95%, 99% or more. In some instances, deconvolution is calculated at a specificity of at least 50%, 60%, 70%, 80%, 90%, 95%, 99% or more for at least 100, 200, 300, 400, or 500 or more independent samples. In some instances, deconvolution has a correlation with the Gold Standard of at least 0.5, 0.6, 0.7, 0.8, 0.9, 0.95, 0.99 or more. In some instances, deconvolution has a correlation with the Gold Standard of at least 0.5, 0.6, 0.7, 0.8, 0.9, 0.95, 0.99 or more for at least 100, 200, 300, 400, or 500 or more independent samples.

In some instances, the mutational burden in a sample is calculated at an accuracy of at least at least 50%, 60%, 70%, 80%, 90%, 95%, 99% or more. In some instances, the mutational burden is calculated at an accuracy of at least 50%, 60%, 70%, 80%, 90%, 95%, 99% or more for at least 100, 200, 300, 400, or 500 or more independent samples. In some instances, the mutational burden in a sample is calculated at a sensitivity of at least at least 50%, 60%, 70%, 80%, 90%, 95%, 99% or more. In some instances, the mutational burden is calculated at a sensitivity of at least 50%, 60%, 70%, 80%, 90%, 95%, 99% or more for at least 100, 200, 300, 400, or 500 or more independent samples. In some instances, the mutational burden in a sample is calculated at a specificity of at least at least 50%, 60%, 70%, 80%, 90%, 95%, 99% or more. In some instances, the mutational burden is calculated at a specificity of at least 50%, 60%, 70%, 80%, 90%, 95%, 99% or more for at least 100, 200, 300, 400, or 500 or more independent samples. In some instances, the mutational burden has a correlation with the Gold Standard of at least 0.5, 0.6, 0.7, 0.8, 0.9, 0.95, or 0.99 or more. In some instances, the mutational burden has a correlation with the Gold Standard of at least 0.5, 0.6, 0.7, 0.8, 0.9, 0.95, or 0.99 or more for at least 100, 200, 300, 400, or 500 or more independent samples.

Therapeutic Applications

Provided herein are methods and systems for determining an immune-oncology profile using sequencing data, wherein the profile may be used for therapeutic applications. In some instances, the profile comprises immune modulatory molecule expression, cell type and ratio, and mutational burden. In some instances, the profile is determined for diagnosis of a disease or disorder. In some instances, the profile is determined for treatment purposes. For example, the profile is used to determine efficacy of a treatment regimen. In some instances, the profile is used to recommend a therapeutic intervention.

In some instances, determination of the immune-oncology profile occurs prior to a treatment, during a treatment, or after a treatment. In some instances, determination of the immune-oncology profile occurs one or more time points prior to a treatment, during a treatment, or after a treatment. Time points for the monitoring and response-to-treatment methods provided herein, include any interval of time. In some instances, the time points are 1 day, 2 days, 3 days, 4 days, 5 days 6 days, 1 week, 2 weeks, 3, weeks, 4 weeks, 1 month, 2 months, 3 months, 4 months, 5 months, 6 months, 7 months, 8 months, 9 months, 10 months, 11 months, 1 year, 2 years or longer apart. In some instances, samples are obtained at any number of time points, including 2, 3, 4, 5, 6, 7, 8, 9, 10, 11, 12, or more time points.

In some instances, the immune-oncology profile is used to determine a specific treatment for a disease or disorder subject. In some instances, a sample is a first sample obtained from a subject at a first time point. In some instances, the method further comprises determining the immune-oncology profile by determining the immune modulatory molecule expression, cell type and ratio, and mutational burden from a second sample obtained from the subject having the related disease or disorder at a second time point; and comparing the immune-oncology profile from the first time point to the second time point. Sometimes, immune-oncology profiles are generated for a subject at multiple time points, wherein the profiles are compared to evaluate the progression of a disease or disorder and/or a response to treatment.

In some cases, the methods and systems described herein are used for diagnosing or treating a disease or disorder, wherein the disease or disorder is cancer. In some instances, the cancer is a solid cancer or a hematopoietic cancer. Sometimes, a cancer targeted herein is a recurrent and/or a refractory cancer. In some instances, the cancer is an acute cancer or a chronic cancer. In some instances, the cancer is an accelerated refractory cancer. In some instances, the cancer is in remission. In some instances, the cancer is a stage I, stage II, stage III, or stage IV cancer. In some instances, the cancer is a juvenile cancer or adult cancer. Examples of cancers include, but are not limited to, breast cancer such as a ductal carcinoma, medullary carcinomas, colloid carcinomas, tubular carcinomas, and inflammatory breast cancer; ovarian cancer, including epithelial ovarian tumors and adenocarcinoma in the ovary; uterine cancer; cervical cancer such as adenocarcinoma in the cervix epithelial, squamous cell carcinoma and adenocarcinomas; prostate cancer, including adenocarcinoma; pancreatic cancer, including epitheliod carcinoma in the pancreatic duct tissue and adenocarcinoma in the pancreatic duct; bladder cancer, including transitional cell carcinoma, urothelial carcinomas, tumors in the urothelial cells, squamous cell carcinomas, adenocarcinomas, and small cell cancers; leukemia, including acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer, including non-small cell lung cancer (NSCLC) such as squamous cell carcinomas, adenocarcinomas, and large cell undifferentiated carcinomas, and small cell lung cancer; skin cancer, including basal cell carcinoma, melanoma, and squamous cell carcinoma; eye retinoblastoma; cutaneous or intraocular melanoma; primary liver cancer; kidney cancer; autoimmune deficiency syndrome related lymphoma, including diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system (CNS) cancers, including primary brain tumors such as astrocytoma, anaplastic astrocytoma, or glioblastoma multiforme, oligodendrogliomas, ependymomas, meningiomas, lymphomas, schwannomas, and medulloblastomas; peripheral nervous system (PNS) cancers, including acoustic neuromas and malignant peripheral nerve sheath tumors (MPNST) such as neurofibromas and schwannomas, malignant fibrous cytomas, malignant fibrous histiocytomas, malignant meningiomas, malignant mesotheliomas, and malignant mixed Müllerian tumors; oral cavity and oropharyngeal cancer such as hypopharyngeal cancer, laryngeal cancer, nasopharyngeal cancer, and oropharyngeal cancer; stomach cancer, including lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer, including thymomas, thymic carcinomas, Hodgkin disease, non-Hodgkin lymphomas carcinoids or carcinoid tumors; rectal cancer; and colon cancer.

In some cases, the methods and systems disclosed herein for determining immune modulatory molecule expression, cell type and ratio, and mutational burden are used for treating cancer. For example, at least one of immune modulatory molecule expression, cell type and ratio, and mutational burden is determined prior to cancer treatment. In some cases, at least one of immune modulatory molecule expression, cell type and ratio, and mutational burden is measured in a sample. In some instances, the sample is obtained from tumor tissues. In some cases, the sample is obtained from non-tumor tissues. In some cases, the sample is obtained from a subject who has cancer or has been diagnosed with cancer. In some cases, the sample is obtained from subjects who have not been diagnosed with cancer. In some cases, the sample is obtained from subjects who are in remission. Following determination of an immune-oncology profile based on at least one of immune modulatory molecule expression, cell type and ratio, and mutational burden, a cancer treatment may be applied. Examples of treatments for cancer include, but are not limited to, chemotherapy, radiation, surgery, or immunotherapy.

In some instances, determination of the immune-oncology profile occurs in conjunction with surgery. For example, determination of the immune-oncology profile occurs prior to tumor surgery and/or following tumor surgery. In some instances, the immune-oncology profile is indicative of the efficacy of the surgery. The immune-oncology profile may be determined any time following surgery. In some instances, the immune-oncology profile is determined 1 day, 2 days, 3 days, 4 days, 5 days 6 days, 1 week, 2 weeks, 3, weeks, 4 weeks, 1 month, 2 months, 3 months, 4 months, 5 months, 6 months, 7 months, 8 months, 9 months, 10 months, 11 months, 1 year, 2 years, or more than 2 years following surgery. In some instances, the immune-oncology profile is determined at any number of time points, including 2, 3, 4, 5, 6, 7, 8, 9, 10, 11, 12, or more time points.

In some instances, determination of the immune-oncology profile occurs in conjunction with chemotherapy. For example, determination of the immune-oncology profile occurs prior to chemotherapy and following chemotherapy. In some instances, determination of the immune-oncology profile indicates the efficacy of the chemotherapy. Examples of chemotherapy includes, but are not limited to, cyclophosphamide, paclitaxel, 5-fluorouracil, 5-aza-2'-deoxycitidine, mitomycin, doxorubicin, and mitoxantrone. The immune-oncology profile may be determined any time following chemotherapy. In some instances, the immune-oncology profile is determined 1 day, 2 days, 3 days, 4 days, 5 days 6 days, 1 week, 2 weeks, 3, weeks, 4 weeks, 1 month, 2 months, 3 months, 4 months, 5 months, 6 months, 7 months, 8 months, 9 months, 10 months, 11 months, 1 year, 2 years, or more than 2 years following chemotherapy. In some instances, the immune-oncology profile is determined at any number of time points, including 2, 3, 4, 5, 6, 7, 8, 9, 10, 11, 12, or more time points.

In some instances, determination of the immune-oncology profile occurs in conjunction with radiation treatment. For example, determination of the immune-oncology profile occurs prior to radiation treatment and/or following radiation treatment. In some instances, the immune-oncology profile indicates the efficacy of the radiation treatment. The immune-oncology profile may be determined any time following radiation treatment. In some instances, the immune-oncology profile is determined 1 day, 2 days, 3 days, 4 days, 5 days 6 days, 1 week, 2 weeks, 3, weeks, 4 weeks, 1 month, 2 months, 3 months, 4 months, 5 months, 6 months, 7 months, 8 months, 9 months, 10 months, 11 months, 1 year, 2 years, or more than 2 years following radiation treatment. In some instances, the immune-oncology profile is determined at any number of time points, including 2, 3, 4, 5, 6, 7, 8, 9, 10, 11, 12, or more time points.

Alternately or in combination with surgery, chemotherapy, or radiation, determination of the immune-oncology profile occurs in conjunction with immune therapy. In some instances, the immune therapy comprises administration of a modulatory agent for an immune checkpoint. Examples of immune checkpoint targets include, but are not limited to, 2B4 (CD244), A2aR, B7H3 (CD276), B7H4 (VTCN1), B7H6, B7RP1, BTLA (CD272), butyrophilins, CD103, CD122, CD137 (4-1BB), CD137L, CD160, CD2, CD200R, CD226, CD26, CD27, CD28, CD30, CD39, CD40, CD48, CD70, CD73, CD80 (B7.1), CD86 (B7.2), CEACAM1, CGEN-15049, CTLA-4, DR3, GAL9, GITR, GITRL, HVEM, ICOS, ICOSL (B7H2), IDO1, IDO2, ILT-2 (LILRB1), ILT-4 (LILRB2), KIR, KLRG1, LAG3, LAIR1 (CD305), LIGHT (TNFSF14), MARCO, NKG2A, NKG2D, OX-40, OX-40L, PD-1, PDL-1 (B7-H1, CD 274), PDL-2 (B7-DC, CD 273), PS, SIRPalpha (CD47), SLAM, TGFR, TIGIT, TIM1, TIM3 (HAVCR2), TIM4, or VISTA. An immune checkpoint modulatory agent in some cases is at least one of a small molecule, an antibody, a nucleic acid encoding an antibody, an antigen binding fragment, a RNA interfering agent, a peptide, a peptidomimetic, a synthetic ligand, and an aptamer. In some instances, an immune checkpoint inhibitor is administered. Examples of immune checkpoint inhibitors are Enoblituzumab (e.g., MGA271), Ipilimumab (e.g., BMS-734016, MDX-010), Tremelimumab (e.g., CP-675, CP-675,206), Lirilumab (e.g., BMS-986015, IPH2102), BMS986016, Pembrolizumab (e.g., MK-3475, SCH 900475), Nivolumab (e.g., BMS-936558, MDX-1106, ONO-4538), Pidilizumab (e.g., CT-011, MDV9300), Atezolizumab (e.g., MPDL3280A, RG7446, R05541267), BMS-936559 (e.g., MDX-1105), Durvalumab, Avelumab, and Bavituximab. In some instances, the immune therapy is CAR T cell or T cell receptor therapy.

Methods and systems provided herein for determination of an immune-oncology profile may be used for prediction of a clinical outcome in response to a therapy. In some instances, the therapy is surgery, radiation, chemotherapy, or immune therapy. In some instances, the immune-oncology profile is used to predict a level of resistance to one or more chemotherapeutic agents. In some instances, the prediction of a clinical outcome based on the immune-oncology profile has an accuracy, specificity, sensitivity, positive predictive value (PPV), a negative predictive value (NPV), or a combination thereof for a type of response. In some instances, the type of response is a positive response. In some instances, a positive response is partial remission (e.g., cancer/tumor has gotten smaller) or complete remission (e.g., all signs of cancer are gone) of the tumor. In some instances, a positive response is the cancer has stopped growing or expanding. In some instances, a positive response is a statistically higher survival rate for a treated subject population compared to an untreated subject population. In some instances, the survival rate is a 1 year, 2 year, 3 year, 4 year, 5 year, 6 year, 7 year, 8 year, 9 year, or 10 year survival rate. In some instances, the type of response is a negative response. In some instances, a negative response is the absence of a positive response. In some instances, a negative response is continued cancer progression or growth. In some instances, a negative response is the continued presence of the cancer. In some instances, a positive response is continued cancer progression or growth at the predicted rate for an untreated subject population. In some instances, a prediction of a clinical outcome (e.g., a positive or negative response) has a positive predictive value for a set of independent samples. In some instances, the PPV for a response to a therapy is at least or about 90% for at least 100 independent samples. A positive predictive value may be accurately determined in at least about 50%, 60%, 70%, 80%, 90%, 95%, or 99% of at least 100, 200, 300, 400, 500, 600, 700, 800, 900, 1000, 2000, 3000, 4000, 5000, 6000, 7000, 8000, 9000, or 10000 independent samples.

In some instances, a prediction is generated using a classifier. In some instances, the proportions of cell types/subtypes determined by deconvolution, mutational burden, immune modulatory molecule expression, or any combination thereof are associated with an outcome such as, for example, a clinical outcome, a diagnosis of disease, and/or a response to therapy. In some instances, the classifier is trained using data comprising one or more of cell type/subtype proportions, mutational burden, and immune modulatory molecule expression along with associated outcomes. In some instances, the classifier comprises a panel of cell type/subtype proportions that are predictive of an outcome. In some instances, the classifier comprises a panel of immune modulatory molecules predictive of an outcome. In some instances, the classifier comprises a panel of mutational burden predictive of an outcome.

Disclosed herein, in some instances, are systems and methods for generating and/or using a classifier to make a prediction of an outcome. The classifier can be a machine learning algorithm or model trained using data from the immune-oncology profile. The data utilized from the immune-oncology profile can include the cell type/subtype proportions or percentages (e.g., immune cell types and percentages in a tumor sample). Examples of the cell types or subtypes include M1 macrophages, M2 macrophages, CD19+ B cells, CD14+ monocytes, CD56+ NK cells, CD8+ T cells, Treg cells, CD4+ T cells, or any combination thereof. Additional examples of cell types or subtypes are found throughout the present disclosure. In some cases, the data includes expression of immune-inhibitory genes or immune escape genes which can include, for example, CTLA4, OX40, PD-1, IDO1, CD47, PD-L1, TIM-3, BTLA, ICOS, ARG1, or any combination thereof. The data can also, in certain cases, include mutational burden information relating to the sample.

The classifier or trained algorithm of the present disclosure may be used make a prediction. The prediction can be based on information from an immune-oncology profile of a sample such as at least one of percentage(s) of cell type(s)/subtype(s), level(s) of immune inhibitory or escape gene(s), or mutational burden. The prediction can comprise stratifying a sample into two or more categories. The prediction can relate to diagnosis and/or prognosis. The prediction can also be based on monitoring the success of treatment of disease. Predictions can also be based on quality of life or symptomatic response. As an example, the prediction for a tumor sample obtained from a subject includes a positive identification of the sample as pancreatic ductal adenocarcinoma (PDA). The prediction optionally also includes a corresponding prediction classifying the sample as having poor survival based on immune-oncology profile data including high PD-L1 expression level and high Treg cell percentage infiltrating the tumor sample. The categories or groups can correspond to various predicted outcomes such as predicted treatment outcome or responsiveness to treatment.

The classifier used to generate predictions includes one or more selected feature spaces such as cell type/subtype proportion/percentage, immune inhibitory gene expression level, and mutational burden. The values for these features obtained from a sample can be fed into the classifier or trained algorithm to generate one or more predictions. In some cases, the methods disclosed herein select for the variables that are of predictive value, for example, by culling the features to generate a feature subset used for generating predictions in the final classifier or model. Methods that reduce the number of variables or features can be selected from a non-limiting group of algorithms including principal component analysis (PCA), partial least squares (PLS) regression, and independent component analysis (ICA). In some cases, the methods disclosed herein analyze numerous variables directly and are selected from a non-limiting group of algorithms including methods based on machine learning processes. Machine learning processes can include random forest algorithms, bagging techniques, boosting methods, or any combination thereof. Methods may be statistical methods. Statistical methods can include penalized logistic regression, prediction analysis of microarrays, methods based on shrunken centroids, support vector machine analysis, or regularized linear discriminant analysis.

The classifier or trained algorithm of the present disclosure as described herein can comprise one feature space. The classifier or trained algorithm of the present disclosure as described herein can comprise two or more feature spaces. The two or more feature spaces may be distinct from one another. Each feature space can comprise types of information about a sample, such as cell type/subtype percentage, expression of immune inhibitory molecules or genes, or mutational burden. The accuracy of the classification may be improved by combining two or more feature spaces in a classifier rather than using a single feature space. In some cases, combining both cell type/subtype percentage and immune inhibitory gene expression results in superior accuracy than using those features individually. Sometimes, accuracy is further improved by incorporating mutational burden. Individual feature spaces may have different dynamic ranges. The difference in the dynamic ranges between feature spaces may be at least 1, 2, 3, 4, or 5 orders of magnitude. As a non-limiting example, the cell subtype percentage feature space may have a dynamic range between 0 and 100, and the immune inhibitory gene expression feature space may have a dynamic range between 0 and about 20.

A feature space can comprise a panel of cell types/subtypes and their percentage or proportion within a sample. A feature space can comprise a panel of immune inhibitory genes and their expression level. A feature space can comprise one or more representations of mutational burden. A panel of an individual feature space may be associated with an outcome such as, for example, responsiveness to treatment. For example, a positive response to an immunotherapy may be associated with certain immune cell types exceeding a threshold percentage within a tumor sample. As another example, a negative response to an immunotherapy may be associated with an immune-inhibitory gene such as PD-L1 exceeding a threshold expression level within a tumor sample. In some cases, the classifier or trained algorithm comprises a panel of cell type/subtype percentages comprising at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 20 cell types/subtypes. The classifier can comprise a panel of immune-inhibitory genes comprising at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, or at least 24 genes.

The classifier of the present disclosure may be trained with a set of samples obtained from subjects. A set of samples can comprise samples from at least 5, 10, 15, 20, 25, 30, 35, 40, 45, 50, 60, 70, 80, 90, 100, 150, 200, 250, 300, 350, 400, 450, 500, 600, 700, 800, 900, 1000, 2000, 3000, 4000, 5000, or more subjects. In some cases, the classifier is trained on a limited sample set with no more than 5, 10, 15, 20, 25, 30, 35, 40, 45, 50, 55, 60, 65, 70, 75, 80, 85, 90, 95, or 100 samples. The classifier may be trained on a limited sample set with no more than 15-20 samples or no more than 20-30 samples. The accuracy of the classifier takes on even greater importance when the sample size is small. A significant factor in the accuracy of the classifier is the quality of the data parameters input into the classifier to generate the prediction or classification. Likewise, the quality of the data input used to train the classifier is important to its predictive ability. For example, a classifier trained on a training data set having cell subtype percentages that were inaccurately determined will incorporate this inaccuracy during the training, which compromises its predictive ability with regards to new samples. When the sample size is large, a few poor data points will not have a significant impact on the resulting classifier. However, in the case when sample size is small such as around 15-25 samples, a few poor data points can negatively impact the classifier's predictive ability to a significant degree. Accordingly, the methods disclosed herein utilizing RNA normalization techniques that account for quantitative differences in RNA content amongst different cell types help generate highly accurate cell type/subtype percentages, which in turn allow for the generation of classifiers that effectively generate predictions despite being trained on small data sets such as, for example, no more than 15, 20, 25, 30, 35, 40, 45, 50, or 60 samples. This capability is critical for small-scale studies such as, for example, Phase VII clinical trials which often entail small sample sizes. Indeed, larger Phase II trials may have 60 subjects, but the experimental group may still be only 15-20 when accounting for controls (e.g., 20 negative placebo controls, 20 receiving traditional treatment, and 20 receiving experimental treatment).

Moreover, in certain instances, the methods disclosed herein utilize end-to-end sample processing and analysis for quality control. As an example, FFPE curls obtained from tumor tissues are obtained, processed, and sequenced via next generation sequencing in a continuous workflow. In this example, the features utilized by the classifier are all mined from the sequencing data. For instance, RNA expression data (RNASeq) is fed into a deconvolution algorithm to determine cell type/subtype percentages. Likewise, the expression levels of immune inhibitory genes are also obtained from the sequencing data. Mutational burden can also be determined from the sequencing data.

A classifier may generate a different prediction each time it is given new sample data. Using different samples on the same classifier can generate a different or unique output each time the classifier is run. Using the same samples on the same classifier can generate a different or unique output each time the classifier is run. The classifier may analyze a sample by comparing it against the panel of features predictive of an outcome or response. In some cases, the classifier carries out the comparing, statistical analysis, downstream analyses, or any combination thereof.

In some cases, the features (e.g., cell type percentages, immune escape gene expression, and mutational burden) are analyzed using feature selection techniques. Feature selection techniques can include filters for evaluating feature relevance by examining the data properties, wrappers that embed the model hypothesis within a feature subset search, or embedded protocols that build the search for an optimal feature set is built into a classifier algorithm. In some cases, the methods described herein comprise a feature selection step in which relevant features are selected for inclusion in the final classifier and/or irrelevant or low relevance features are culled or removed from the final classifier.

Examples of filters that can be beneficial for use in the methods of the present disclosure include parametric methods such as two sample t-tests, analysis of variance (ANOVA) analyses, Gamma distribution models, or Bayesian models. Filters can include model free methods such as Wilcoxon rank sum tests, rank products methods, random permutation methods, between-within class sum of squares tests, or threshold number of misclassification. In some cases, filters include multivariate methods such as bivariate analysis, correlation based feature selection methods, minimum redundancy maximum relevance, Markov blanket filter, and uncorrelated shrunken centroid methods.

Wrappers that may be beneficial for use in the methods of the present disclosure can include sequential search methods, estimation of distribution algorithms, or genetic algorithms. Embedded protocols that may be beneficial for use in the methods of the present disclosure can include random forest algorithms, weights of logistic regression algorithms, or weight vector of support vector machine algorithms.

The statistical results obtained from the methods described herein can provide the likelihood the prediction is accurate. In some cases, the prediction is presented as a diagnosis along with a likelihood of accuracy such as, for example, a prediction of a positive response to a therapeutic cancer treatment with at least a 70%, 75%, 80%, 85%, 90%, or 95% estimated accuracy. The predictions may be analyzed using statistical tools including students T test, two sided T test, Pearson rank sum analysis, hidden Markov model analysis, analysis of q-q plots, principal component analysis, one way analysis of variance (ANOVA), two way ANOVA, and other statistical methods.

Computer Systems

Figure 8:
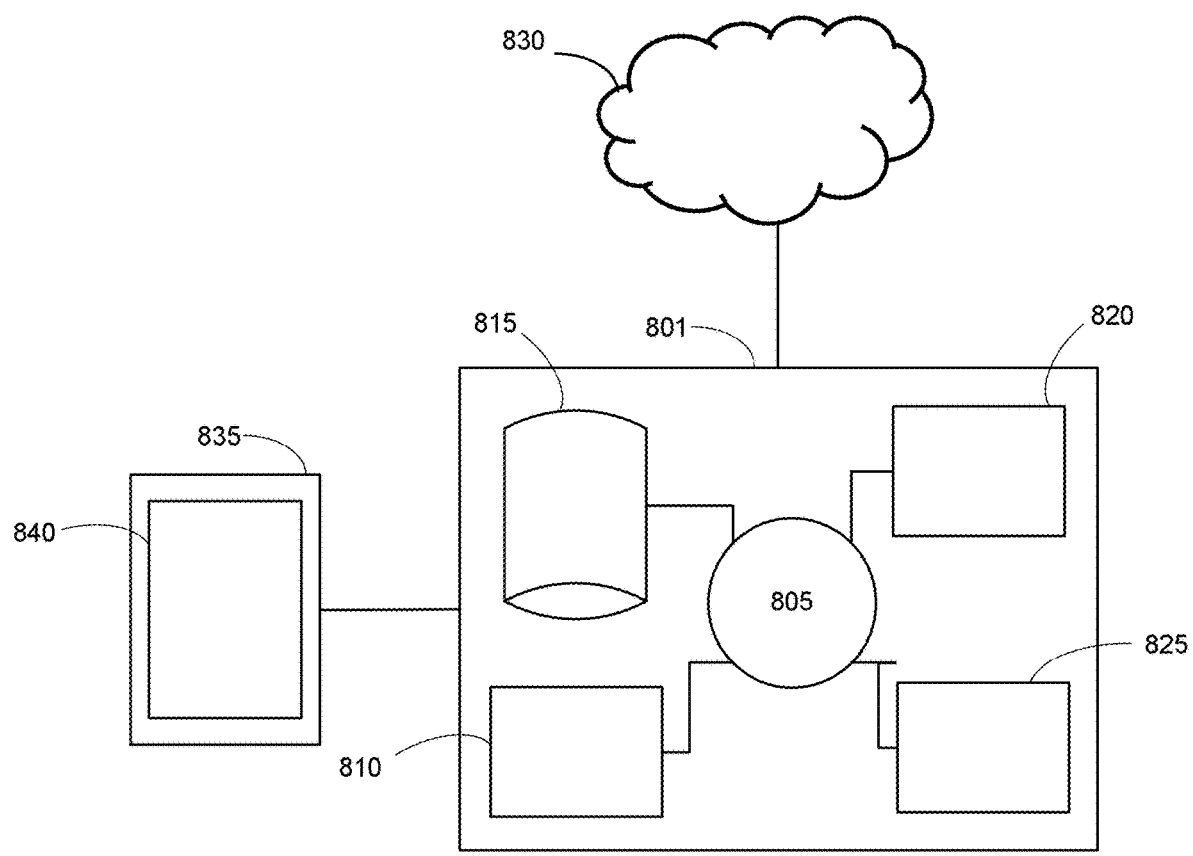
FIG. 8 schematically illustrates a computer system that is programmed or otherwise configured to implement methods provided herein.

The present disclosure provides computer systems that are programmed to implement methods of the disclosure. FIG. 8 shows a computer system 801 that is programmed or otherwise configured to carry out executable instructions. The computer system may be programmed to process nucleic acid sequencing information to generate a classifier comprising a panel of genetic variations predictive of adverse response to chemotherapy, by associating the nucleic acid sequencing information with adverse response to chemotherapy. The computer system may be programmed with a classifier for analyzing genetic information to generate a prediction of an adverse response to one or more chemotherapeutic agents. The computer system 801 can regulate various aspects of the methods of the present disclosure, such as, for example, training the algorithm with the nucleic acid sequencing information of a set of samples to generate a trained algorithm or classifier. The computer system 801 may determine the positive predictive value of a classifier by analyzing a set of independent samples with the classifier and comparing the actual incidents of adverse response to the predicted risk of adverse response. The computer system 801 can be an electronic device of a user or a computer system that is remotely located with respect to the electronic device. The electronic device can be a mobile electronic device.

The computer system 801 includes a central processing unit (CPU, also "processor" and "computer processor" herein) 805, which can be a single core or multi core processor, or a plurality of processors for parallel processing. The computer system 801 also includes memory or memory location 810 (e.g., random-access memory, read-only memory, flash memory), electronic storage unit 815 (e.g., hard disk), communication interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communication bus (solid lines), such as a motherboard. The storage unit 815 can be a data storage unit (or data repository) for storing data. The computer system 801 can be operatively coupled to a computer network ("network") 830 with the aid of the communication interface 820. The network 830 can be the Internet, an internet and/or extranet, or an intranet and/or extranet that is in communication with the Internet. The network 830 in some cases is a telecommunication and/or data network. The network 830 can include one or more computer servers, which can enable distributed computing, such as cloud computing. The network 830, in some cases with the aid of the computer system 801, can implement a peer-to-peer network, which may enable devices coupled to the computer system 801 to behave as a client or a server.

The CPU 805 can execute a sequence of machine-readable instructions, which can be embodied in a program or software. The instructions may be stored in a memory location, such as the memory 810. The instructions can be directed to the CPU 805, which can subsequently program or otherwise configure the CPU 805 to implement methods of the present disclosure. Examples of operations performed by the CPU 805 can include fetch, decode, execute, and writeback.

The CPU 805 can be part of a circuit, such as an integrated circuit. One or more other components of the system 801 can be included in the circuit. In some cases, the circuit is an application specific integrated circuit (ASIC).

The storage unit 815 can store files, such as drivers, libraries and saved programs. The storage unit 815 can store user data, e.g., user preferences and user programs. The computer system 801 in some cases can include one or more additional data storage units that are external to the computer system 801, such as located on a remote server that is in communication with the computer system 801 through an intranet or the Internet.

The computer system 801 can communicate with one or more remote computer systems through the network 830. For instance, the computer system 801 can communicate with a remote computer system of a user (e.g., a laptop or a smart phone). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 801 via the network 830.

Methods as described herein can be implemented by way of machine (e.g., computer processor) executable code stored on an electronic storage location of the computer system 801, such as, for example, on the memory 810 or electronic storage unit 815. The machine executable or machine readable code can be provided in the form of software. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 801, can be embodied in programming Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk.

"Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases or other components shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 801 can include or be in communication with an electronic display 835 that comprises a user interface (UI) 840 for providing, for example, reports or results of risk stratification analysis of the nucleic acid sequencing information of a sample. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 805. The algorithm can, for example, analyze the nucleic acid sequencing information obtained from a sample to stratify a risk of adverse response to chemotherapy (e.g., one or more chemotherapeutic agents) for the subject from whom the sample was obtained.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention.

Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLES

The following examples are given for the purpose of illustrating various embodiments of the disclosure and are not meant to limit the present disclosure in any fashion. The present examples, along with the methods described herein are presently representative of certain embodiments, and are not intended as limitations on the scope of the disclosure. Changes therein and other uses which are encompassed within the spirit of the disclosure as defined by the scope of the claims will occur to those skilled in the art.

Example 1: Classification of a Tumor Microenvironment

Figure 4A:
FIG. 4A, FIG. 4B, FIG. 4C, and FIG. 4D depict methods for identifying tumor mutational burden.
Figure 4B:
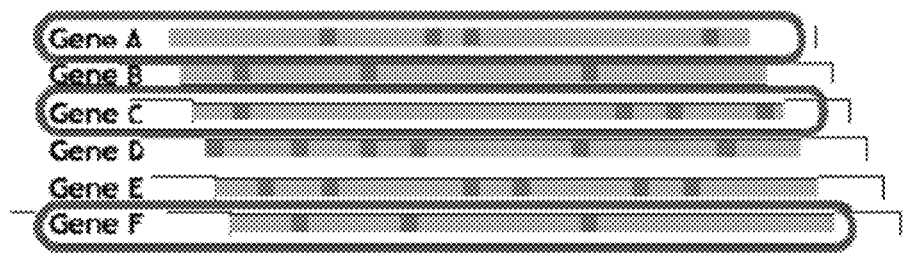
Figure 4C:
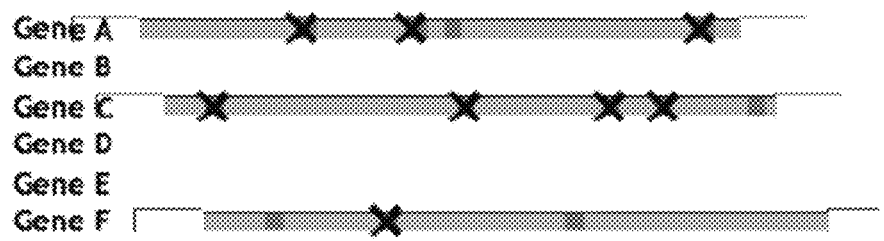
Figure 4D:
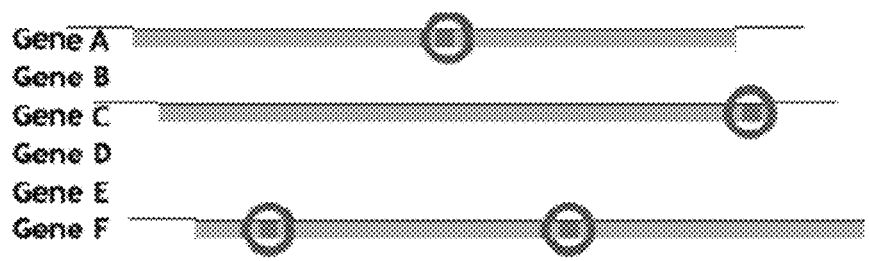

A tumor microenvironment was characterized by determining immune modulatory molecule expression levels, cell type and ratio, and tumor mutational burden.
 RNA Extraction
 RNA was extracted from formalin fixed paraffin embedded (FFPE) samples using the RNeasy kit (Qiagen) according to manufacturer's instructions.
 Generation of Sequencing Library
 Following RNA extraction, a sequencing library for next generation sequencing was generated according to manufacturer's instructions (Illumina). Coding regions were captured using Illumina Access kits.
 Next Generation Sequencing
 The enriched genes were sequenced on an Illumina's NextSeq sequencing machine to generate sequencing data and expression data.
 Inhibitory Molecule Expression
 The sequencing and expression data is used to determine the expression level of selected immune modulatory molecules including PD-1, PD-L1, CTLA-4, OX40, TIM-3, BTLA, ICOS, CD47, IDO1, and ARG1.
 Cell Type and Ratio Deconvolution
 Following next generation sequencing, sequencing data was analyzed for cell type and by ratio deconvolution. The use of next generation sequencing to generate sequencing and expression data for use in deconvolving cell types/subtypes as described herein is a new approach that provides superior performance compared to, for example, conventional gene expression systems such as those using microarrays. In addition, routine studies looking at immune cell percentages in tissue use a conventional approach of utilizing public databases of microarray expression data, which may be able to identify changes in cell proportions between different samples, but are ineffective for accurately determining the true percentage of a cell type/subtype in a given sample.
 Ratio deconvolution was carried out using a deconvolution matrix comprising a set of cell expression signatures or "fingerprints." The cell expression signatures or "fingerprints" were generated using sequencing data obtained from samples substantially composed of specific cell types (e.g., a CD4+naïve cell fingerprint obtained from a purified population of CD4+naïve cells). The cell-specific fingerprints were then placed into the deconvolution matrix. This matrix was then applied to the complex data set of RNA sequencing and gene expression data to allow for identification of cell types in the data and the relative proportions of each cell type. Included in the cell expression signatures or fingerprints were genes that were significantly differentially expressed in pairwise cell type differential expression analysis as well as those genes that were expressed at a consistent level within cell type across biological replicates.
 Ratio deconvolution was also performed. The process of determining individual components from bulk sequencing and expression profiles was accomplished by solving the matrix equation: $Ax=b$ where A was the cell expression fingerprints, x was the cell percentages, and b was the bulk expression counts. A vector regression method with data normalization was performed. See FIG. 3. Briefly, to deconvolve a mixture with N cell types using M genes, the problem is set up according to FIG. 3. Cell fractions were determined and normalization across rows was performed. The expression counts of each gene were normalized to be in the range of 0 to 1 across each cell type and the sample in question such as a mixture of cells. All genes were weighted equally regardless of their absolute expression value.
 Tumor Mutational Burden Calculation
 Tumor mutational burden was calculated. Following RNA sequencing, all the variants including somatic and germline were determined as shown in FIG. 4A with the variants indicated by the dark squares along the representative gene sequences. Total somatic mutational burden was thus determined without use of a paired normal. A panel of genes (~4000) was then used for subsequent analysis since they were determined to correlate with mutational burden across the genome. This concept is illustrated in FIG. 4B in which the correlated genes A, C, and F are circled. Several germline variation databases were used to identify the initial variant calls that were germline variants based on a frequency of greater than 0.01%, and the identified germline variants were then excluded from mutational burden analysis. As shown in FIG. 4C, the excluded germline variants are crossed out with an "X". From the remaining variants (which are circled in FIG. 4D) on the panel of genes, the total somatic mutational burden was extrapolated.
 Tumor Microenvironment Summary Report
 Data from the immune modulatory molecule expression, cell type and ratio deconvolution, and tumor mutational burden calculation was then compiled to generate a summary of these metrics in the tumor microenvironment. The summary was presented in an immune-oncology profile that displayed the information in a graphical output. The immune modulatory molecule expression was displayed in a bar graph alongside a reference or control expression level. A general breakdown of the cell types (immune, tumor, and stromal cells) and their relative percentages/proportions of the overall cell population in the sequenced sample were displayed in a pie chart. A more specific breakdown based on the percentages of specific cell types (T cells, CD4+ cells, myeloid cells, NK cells, and B cells) and cell sub-types (e.g., CD4+ and CD8+ T cells) in the sample was graphically displayed. Finally, the mutational burden was displayed as an indicator or marker on an axis ranging from low mutational burden (0 mutations per Megabase) to high mutational burden (2000 mutations per Megabase).

Example 2: Mutational Burden Analysis

Genes that provide improved resolution and accuracy for mutational burden analysis were determined. All the human genes were ranked in order using a weighted average of their likelihood to be mutated using data from public databases as well as by their consistency of expression across multiple tissues. Three different cancer types were analyzed with about 50 samples of each cancer. The accuracy was determined with an increasing number of genes from Table 5.

From Table 6, correlation with a Gold Standard mutational burden increased with about 2000 genes and then started to plateau. Mutational burden was compared to the Gold Standard mutational burden calculated using paired normal analysis of DNA. Specifically, the Gold Standard mutational burden measures somatic mutations using DNA sequence data obtained from the sample by comparing allele frequencies in normal and tumor sample alignments, annotating the identified mutations, and aggregating the mutations.

TABLE 6

| Genes | Correlation with Gold Standard | | |
|---|---|---|---|
| | HNSC | Lung | Breast |
| 100 | 0.65 | 0.32 | 0.46 |
| 250 | 0.75 | 0.54 | 0.82 |
| 500 | 0.84 | 0.58 | 0.84 |
| 1000 | 0.87 | 0.7 | 0.9 |
| 2000 | 0.9 | 0.85 | 0.91 |
| 4000 | 0.93 | 0.91 | 0.91 |

Example 3: Characterization of a Glioblastoma Tumor Microenvironment

Figure 5A:
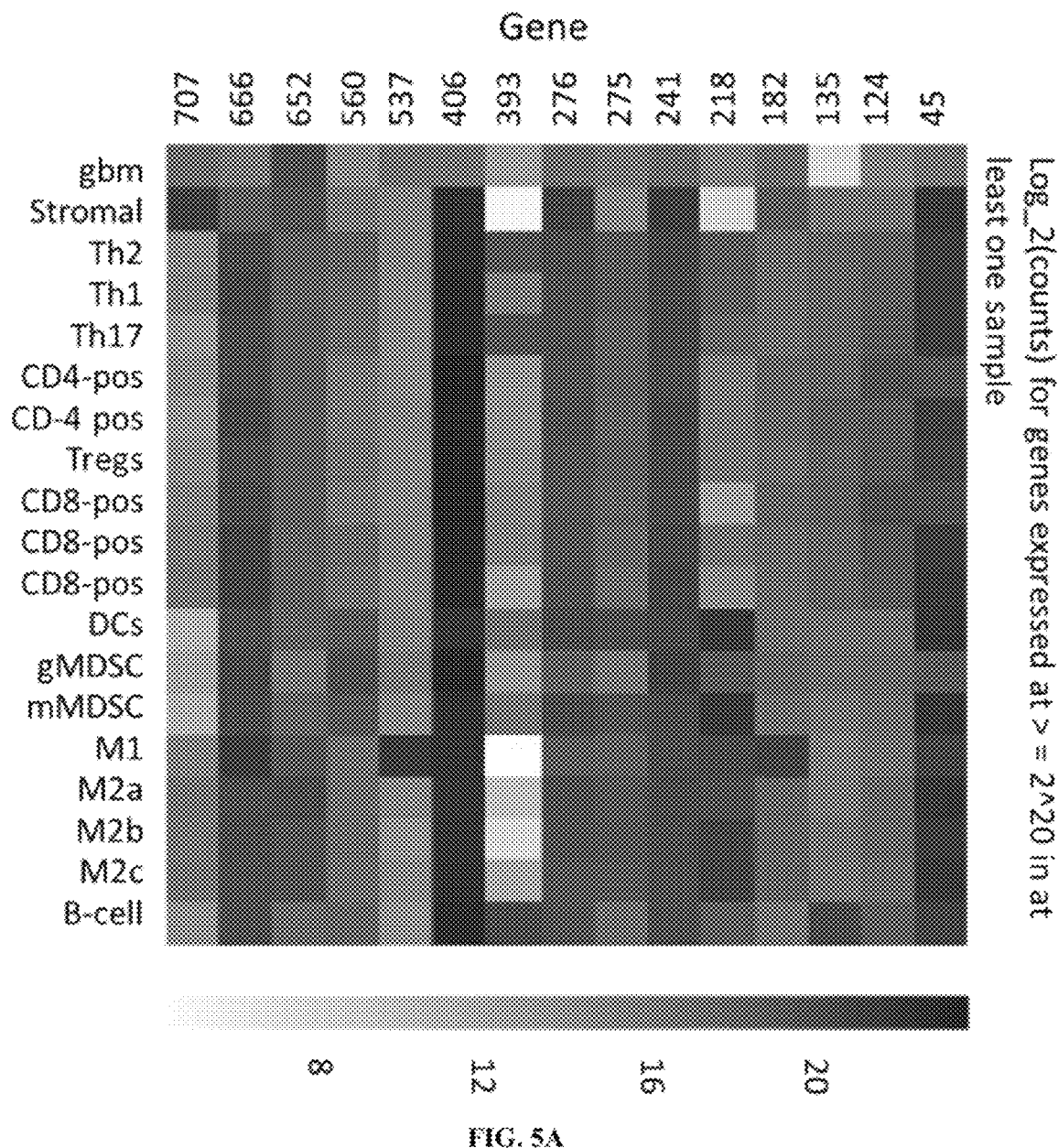
FIG. 5A and FIG. 5B depict gene expression levels in glioblastoma.

Using similar methods as described in Examples 1-2, a glioblastoma tumor microenvironment was characterized. As seen in FIG. 5A, different cell types were on the y-axis, while genes were on the x-axis. Gene expression level was represented by color with a darker purple color indicating relatively higher expression. In black and white, the darker shade indicates higher expression, while the lighter shade indicates lower expression. Gene 406 was identified as distinguishing a glioblastoma cancer cell type and immune cell types.

Figure 5B:
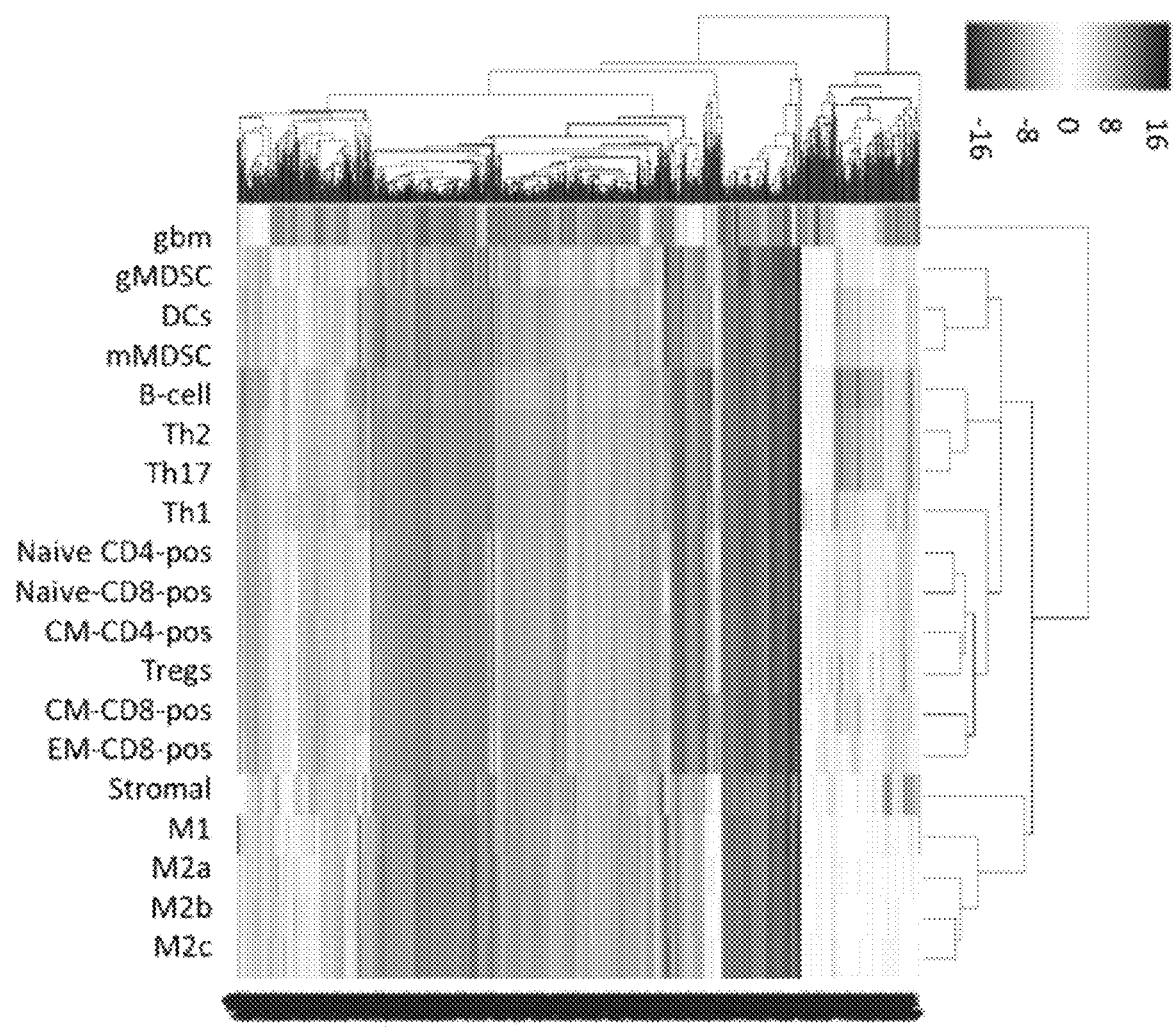

A similar gene matrix was also generated using about 800 genes (FIG. 5B). Referring to FIG. 5B, expression levels of multiple genes was determined and used to characterize the glioblastoma tumor microenvironment. The genes listed on the y-axis in FIG. 5B from top down include gbm, gMDSC, DCs, mMDSC, B-cell, Th2, Th17, Th1, Naïve-CD4-pos, Naïve-CD8-pos, CM-CD4-pos, Tregs, CM-CD8-pos, EM-CD8-pos, Stromal, M1, M2a, M2b, and M2c. The legend in FIG. 5B shows decreased expression indicated by a blue color, increased expression indicated by a red/orange color, and white being neutral or no change in expression. Most of the visible expression data indicates no change or increased expression.

Figure 6:
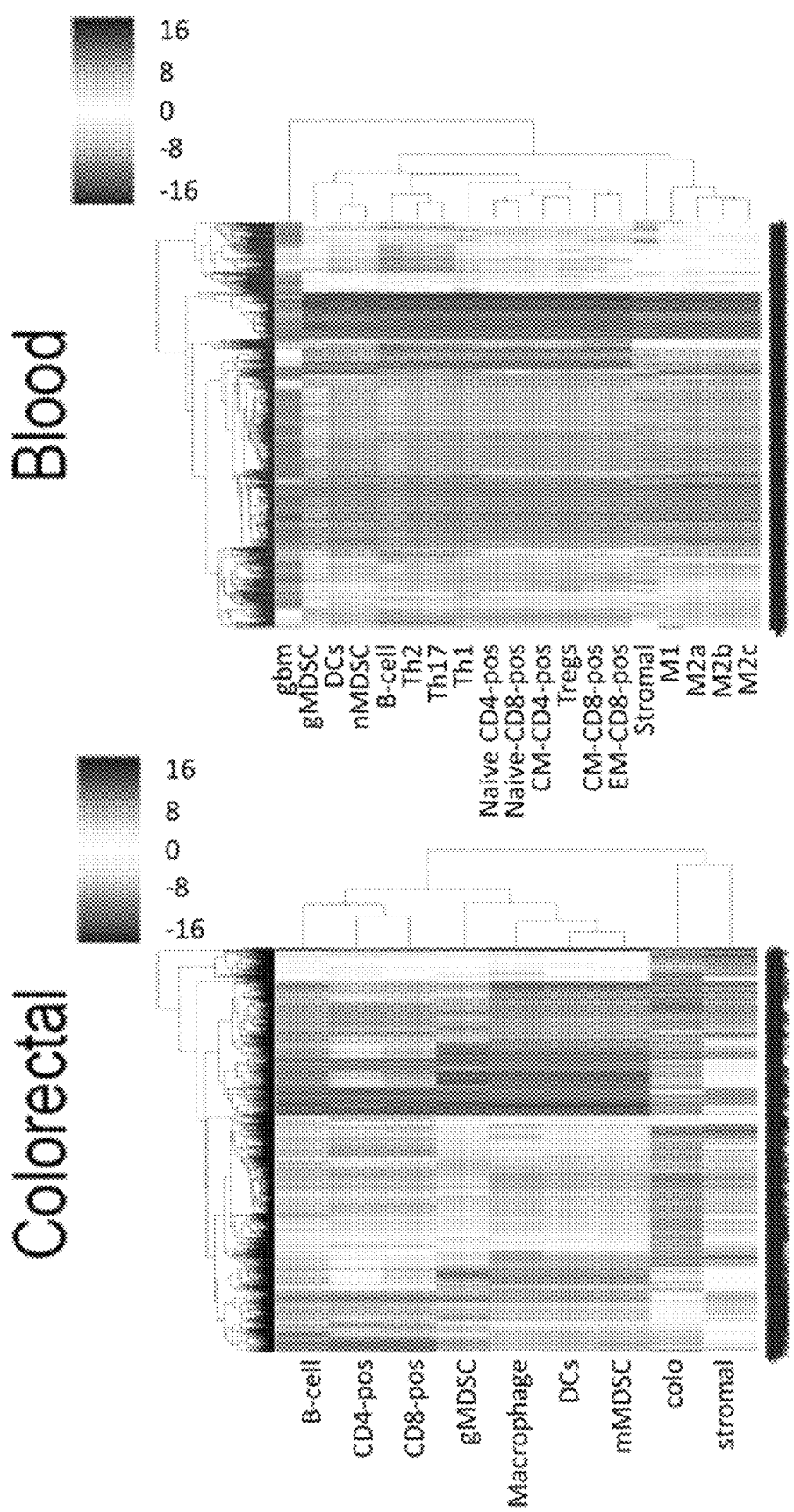
FIG. 6 depicts gene expression levels in colorectal and blood cancers.

Example 4: Characterization of Tumor Microenvironment for Various Types of Cancers A tumor microenvironment was determined for various cancer types. Using similar methods as described in Examples 1-2, expression levels of multiple genes was identified in colorectal and blood cancers (FIG. 6). Gene expression levels were used to characterize the colorectal and blood cancer microenvironment. The genes listed on the y-axis in FIG. 6 for colorectal cancer from top down include B-cell, CD4-pos, CD8-pos, gMDSC, Macrophage, DCs, mMDSC, and stromal. The genes listed on the y-axis in FIG. 6 for blood from top down include gbm, gMDSC, DCs, mMDSC, B-cell, Th2, Th17, Th1, Naïve-CD4-pos, Naïve-CD8-pos, CM-CD4-pos, Tregs, CM-CD8-pos, EM-CD8-pos, Stromal, M1, M2a, M2b, and M2c. The legend in FIG. 6 shows decreased expression indicated by a blue color, increased expression indicated by a red/orange color, and white being neutral or no change in expression. Most of the visible expression data indicates no change or increased expression.

Example 5: Transformation of RNA Sequencing Data

The amount of RNA per immune cell type was determined.

RNA Per Cell Calculations

Figure 9:
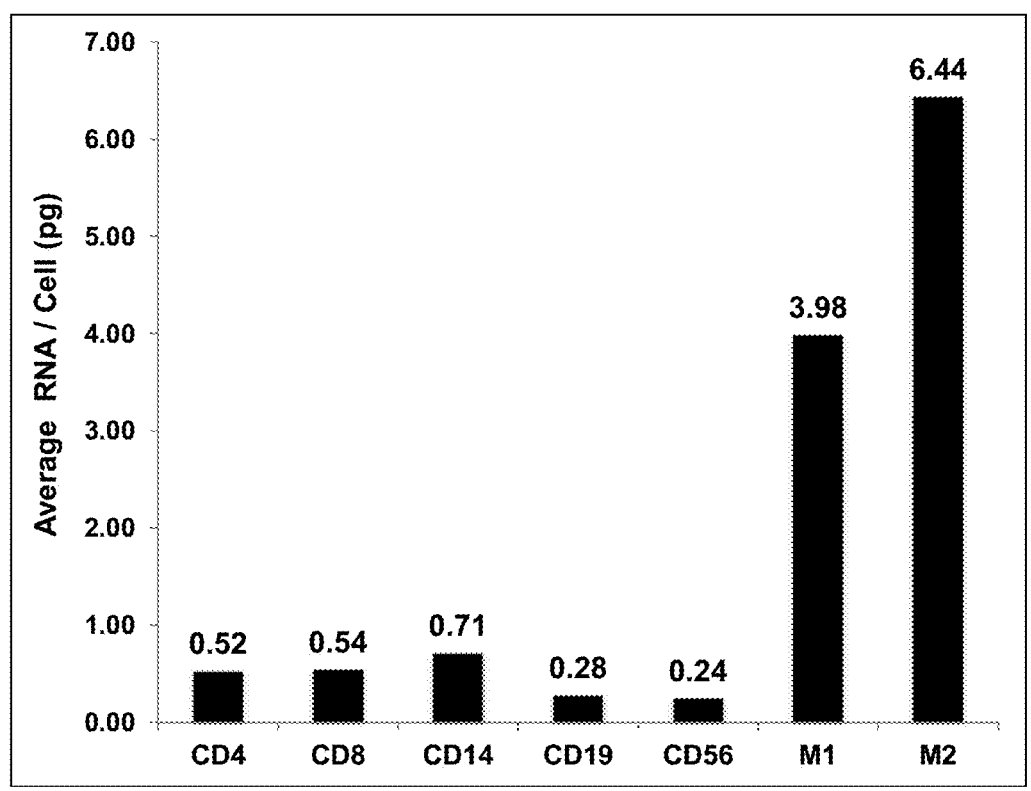
FIG. 9 shows the average amount of total RNA per cell for each immune cell type.

Immune cell types (CD4+ T cells, CD8+ T cells, B-cells, Monocytes, Treg and natural killer cells) were purified by flow cytometry from multiple peripheral blood mononuclear cell (PBMC) donors. Macrophages M1 and M2 were differentiated in cell culture from monocyte cell donors and purified using fluorescent activated cell sorting (FACs) to obtain pure M1 and M2 populations. RNA was extracted from the purified cells and sequenced. The number of cells obtained from FACS was recorded with the amount of RNA extracted from each cell enabling calculations for the amount of RNA per cell for each cell type. FIG. 9 shows the average amount of total RNA per cell for each immune cell type.

Cell Correction Methods

The effect on cell percentages and ratios calculated from deconvolution using SVM (support vector machines) when the different cell types contained distinct amounts of total RNA were determined. Cell mixtures were generated in duplicate from Macrophages M1 and M2 spiked into perinuclear blood mononuclear cell (PBMC) samples in decreasing ratios. These cell mixtures represent a "gold standard" or sample where the true answer (percentages of cell types in the mixture) was known before deconvolution. The cell mixture ratios are shown for PBMC samples comprising 500,000 cells in Table 7.

TABLE 7

| Sample Name | % Macrophage | % PBMC |
|---|---|---|
| M1-100 | 100 | 0 |
| M1-50 | 50 | 50 |
| M1-25 | 25 | 75 |
| M1-10 | 10 | 90 |
| M1-5 | 5 | 95 |
| M1-2 | 2 | 98 |
| M1-0 | 0 | 100 |
| M2-100 | 100 | 0 |
| M2-50 | 50 | 50 |
| M2-25 | 25 | 75 |
| M2-10 | 10 | 90 |
| M2-5 | 5 | 95 |
| M2-2 | 2 | 98 |
| M2-0 | 0 | 100 |
| *M1M2-100 | 100 | 0 |
| M1M2-50 | 50 | 50 |
| M1M2-25 | 25 | 75 |
| M1M2-10 | 10 | 90 |
| Ivi1M2-5 | 5 | 95 |

TABLE 7-continued

| Sample Name | % Macrophage | % PBMC |
|---|---|---|
| M1M2-2 | 2 | 98 |
| M1M2-0 | 0 | 100 |

*M1M2 = 50% M1 + 50% M2 mix

Figure 10A:
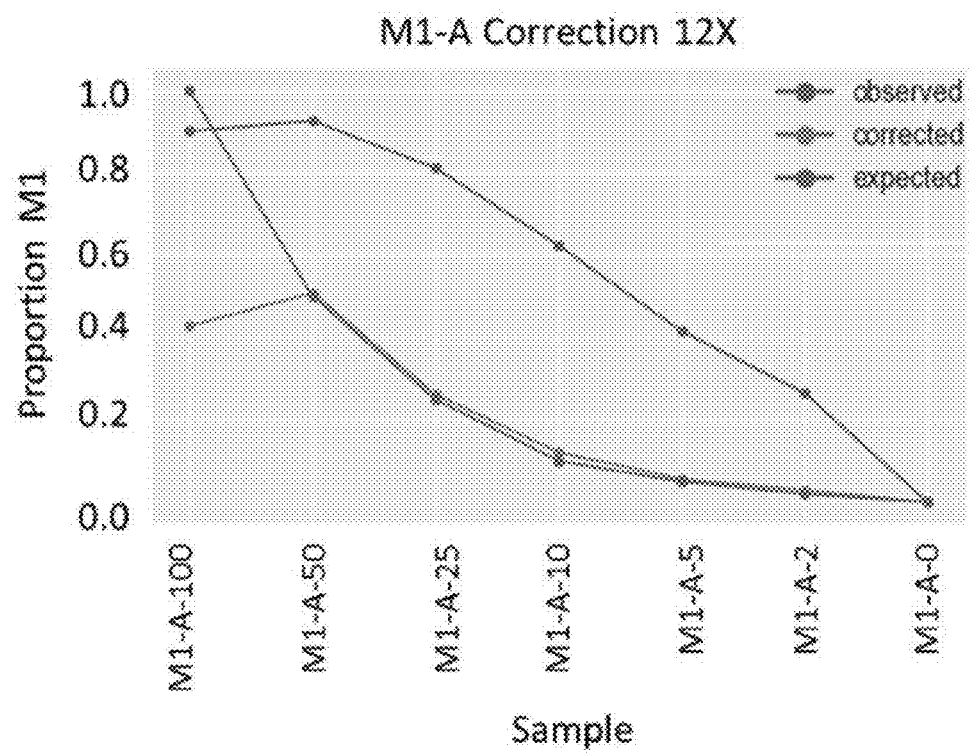
FIG. 10A shows a graph of the observed, expected, and corrected number of M1 macrophages calculated at different dilution points through deconvolution.
Figure 10B:
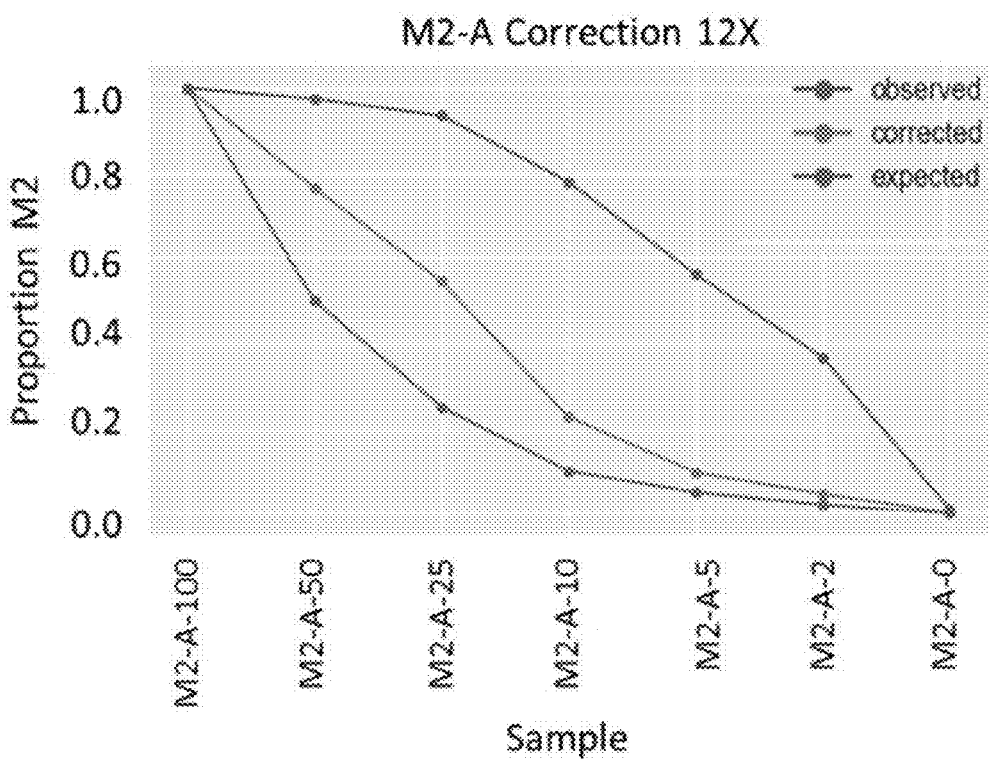
FIG. 10B shows a graph of the observed, expected, and corrected number of M2 macrophages calculated at different dilution points through deconvolution.
Figure 10C:
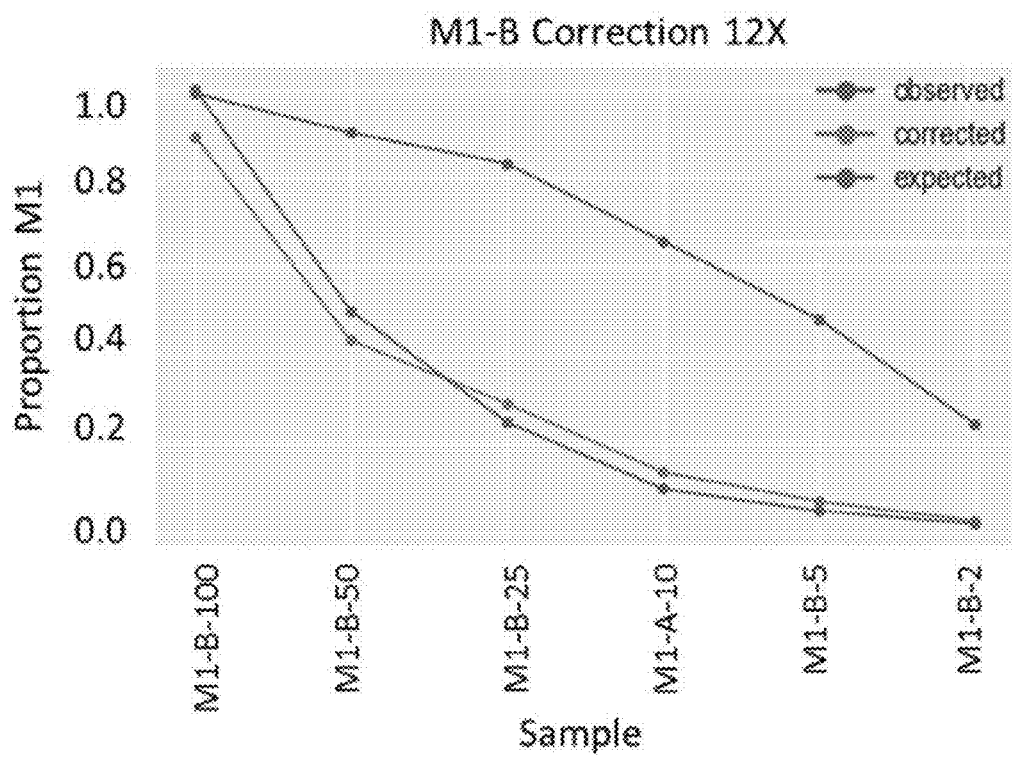
FIG. 10C shows another graph of the observed, expected, and corrected number of M1 macrophages calculated at different dilution points through deconvolution.
Figure 10D:
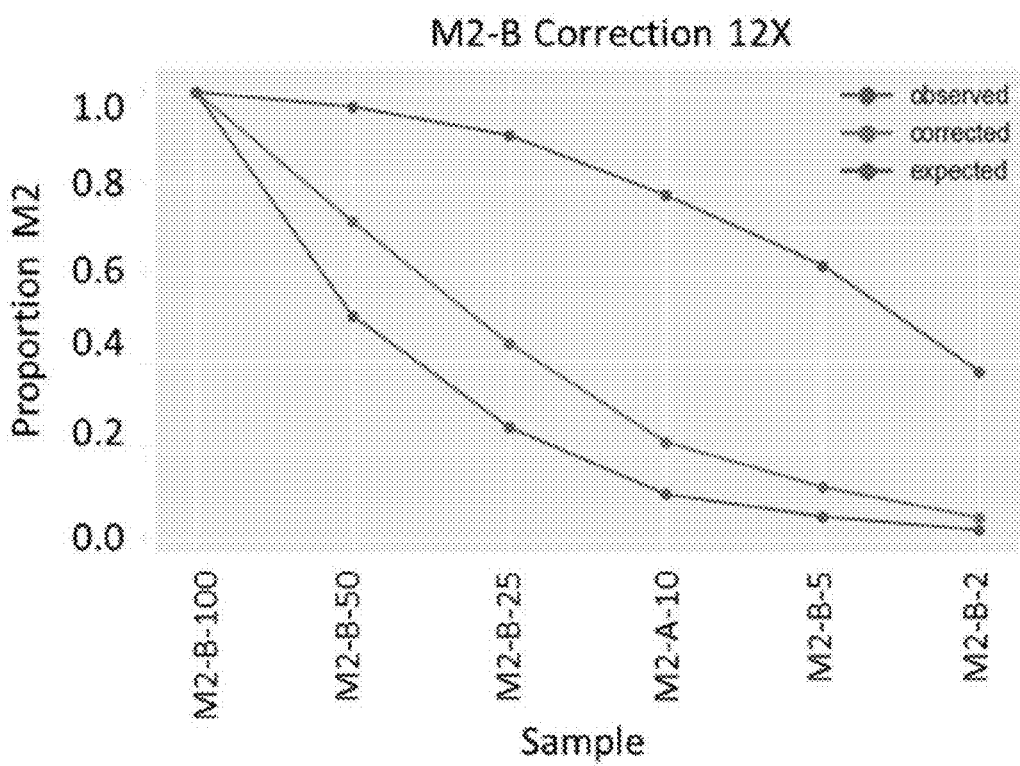
FIG. 10D shows another graph of the observed, expected, and corrected number of M2 macrophages calculated at different dilution points through deconvolution.
Figure 10E:
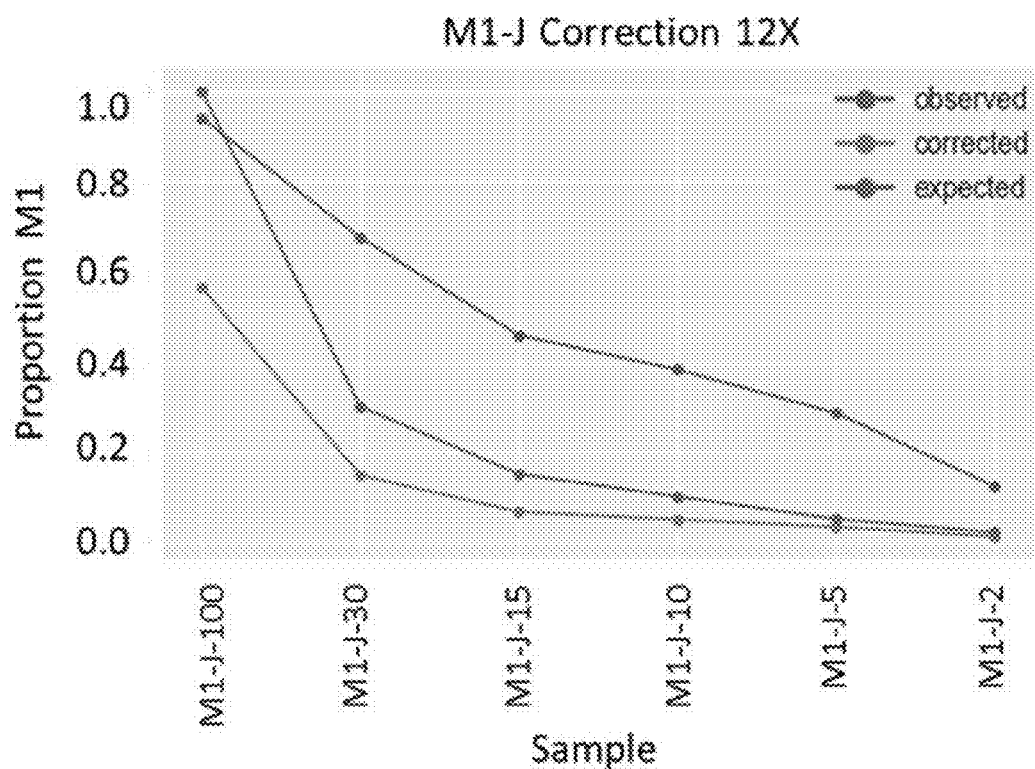
FIG. 10E shows another graph of the observed, expected, and corrected number of M1 macrophages calculated at different dilution points through deconvolution.
Figure 10F:
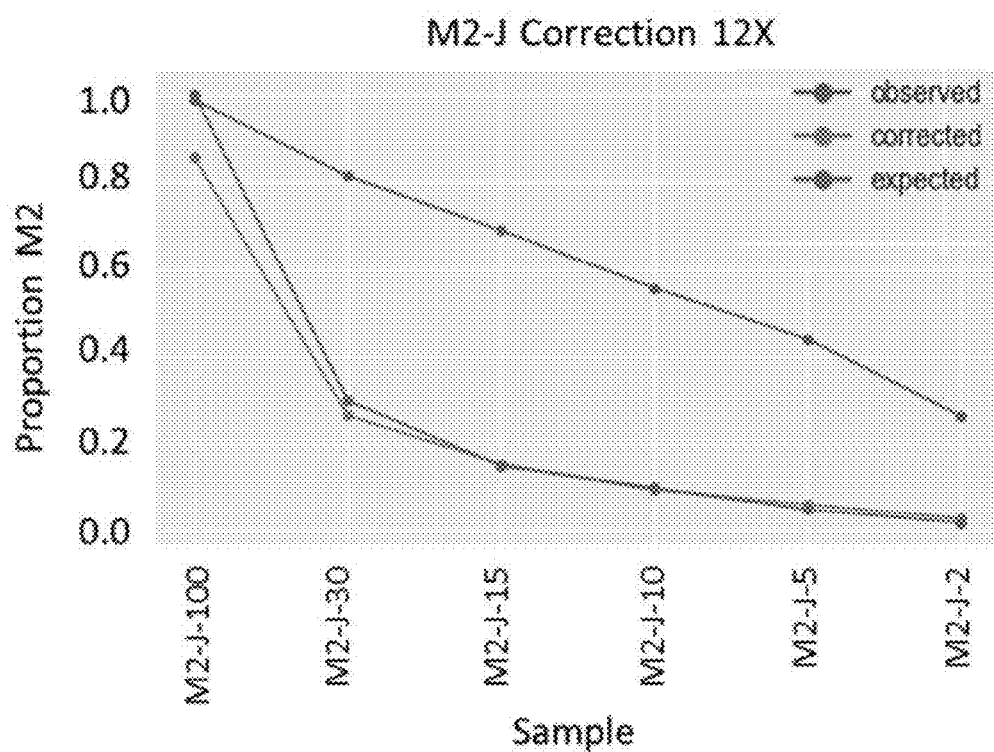
FIG. 10F shows another graph of the observed, expected, and corrected number of M2 macrophages calculated at different dilution points through deconvolution.

Total RNA was extracted from the cell mixtures and sequenced. Following sequencing, the resulting data was analyzed for M1 and M2 cell percentages, using SVM-based deconvolution as described herein, and the computed cell type percentages were compared to the known percentages (ground truth). As seen in FIGS. 10A-10F, since the total RNA amount contained in macrophages is much higher than observed in other immune cells, the deconvolution method resulted in the calculation of a higher percentage of macrophage cells than as compared to truth. When observing FIG. 10A as a non-color drawing, at the leftmost data points on the chart, the M1 proportion data is shown in order from top to bottom in order as "expected", "observed", and "corrected". In FIG. 10B, the highest M2 proportions are "observed" followed by "corrected" and then "expected". In FIG. 10C, at the leftmost data points on the chart, the highest data point corresponds to expected followed by observed and then corrected. In FIG. 10D, the highest M2 proportions are "observed" followed by "corrected" and then "expected". In FIG. 10E, at the leftmost data points on the chart, the highest data point corresponds to "expected" followed by "observed" and then "corrected". In FIG. 10F, at the leftmost data points on the chart, the highest data point corresponds to "expected" followed by "observed" and then "corrected". Based on these results, a method for correcting cell percentages for any cell type as required based on cellular RNA amount was developed. The equation below is one method for correcting cell percentages following deconvolution:

$$(1 - o_k)i_k m_k - \sum_{j \neq k} o_k m_j i_j = 0 \quad \text{Equation 1}$$

$$\sum i_k = 1 \quad \text{Equation 2}$$

Equation 1 was used for each of k cell types. Referring to the equation, $o_k$ is the observed output $i_k$ is the actuation output, and $m_k$ is the multiplier. For each cell type equation, the sum subtracted is over the o, m, i values for the "other" cell types. All k equations of equation 1 were set to 1. The second equation is the constraint that all inputs add to 1.

Correction of Macrophages M1 and M2 Percentages

Because the amount of RNA in macrophage cells was much higher than that seen in other immune cell types, the analysis algorithms compute this increased amount of RNA as a greater percentage of cells than expected. In order to bring the percentage of macrophage cells in line with the expected percent, Equation 1 and Equation 2 were used. This correction translated the percentages from "transcript space" to "cell space" by applying a correction based on amount of RNA (transcripts) per cell. Once the equation is applied to the M1 and M2 cell percentage cells, the percentages highly resemble the expected percentages. The factor of correction used here was 12×. Results using methods as described herein are seen in Table 8.

TABLE 8

| Cell Type | Amount of RNA per Cell (pg/cell) | Cell correction value for deconvolution (normalized to CD4+ T cell) |
|---|---|---|
| CD4+ T cell | 0.52 | 1.00 |
| CD8+ T cell | 0.54 | 1.03 |
| Monocyte | 0.71 | 1.35 |
| B-cell | 0.28 | 0.53 |
| NK | 0.24 | 0.47 |
| M1 Macro | 3.98 | 7.59 |
| M2 Macro | 6.44 | 12.26 |

Example 6—Cell Percentage Accuracy

Figure 11:
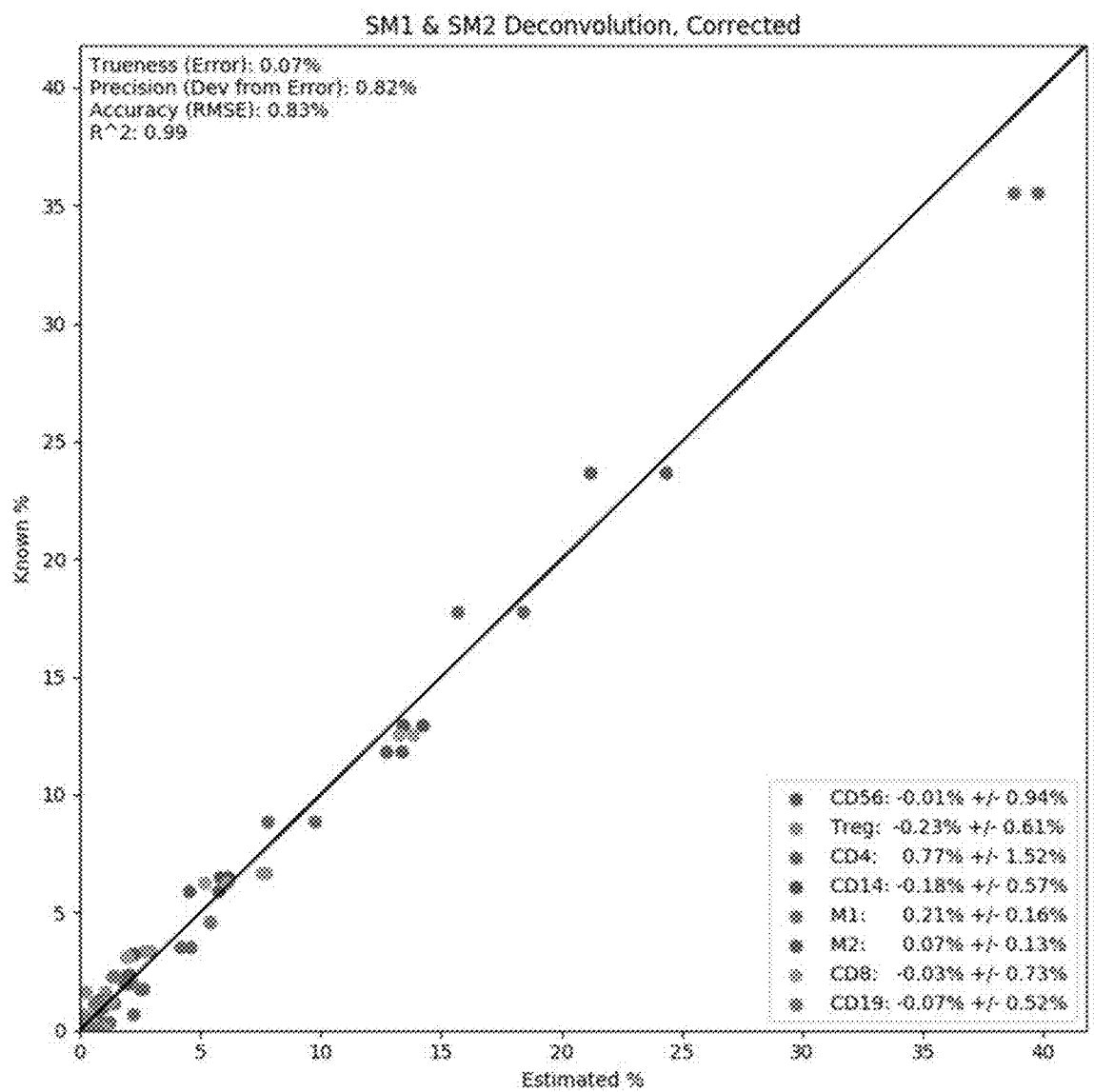
FIG. 11 shows a graph plotting a comparison of known cell percentages to estimated cell percentages obtained using the deconvolution methods described herein.

The estimated cell percentages generated according to the methods disclosed herein were compared to known cell percentages calculated using flow cytometry to determine the accuracy of the deconvolution algorithm, as shown in FIG. 11. The percentage of immune cells in complex mixtures was measured using flow cytometry (y-axis=Known %) and compared to the estimated percentage of immune cell types from RNA sequencing data of the complex mixtures (x-axis=Estimated %). As shown in the graph, the cell percent estimates exhibit high trueness, precision, accuracy and correlation in comparison to the known percent.

This experiment estimating cell percentages and calculating true cell percentages using flow cytometry and was performed in triplicate, and one of the replicates was used to train for cell corrections in comparison to the known percent from flow. The data shown in FIG. 11 represents an assessment of the trained model using testing data (using the training corrections). Thus, this method corrected for deviations from the true cell percentages by training the model as opposed to using cell corrections based on RNA content/quantity per cell. The high accuracy of the model is indicated by the deviations indicated in FIG. 11, which are also shown in Table 9 below.

TABLE 9 estimated cell percentage deviation from true cell percentage

| Cell type/subtype | % Deviation of Estimated Percentage from Known Percentage |
|---|---|
| CD56 | −0.01% +/− 0.94% |
| Treg | −0.23% +/− 0.61% |
| CD4 | 0.77% +/− 1.52% |
| CD14 | −0.18% +/− 0.57% |
| M1 | 0.21% +/− 0.16% |
| M2 | 0.07% +/− 0.13% |
| CD8 | −0.03% +/− 0.73% |
| CD19 | −0.07% +/− 0.52% |

Example 7—Clinical Sample Classification for Diagnosis and Prognosis

An immune-oncology profile that includes the relative quantities of 8 cell types and expression level for 10 immune-inhibitory genes (e.g., "escape genes") was determined for 15-20 biological samples obtained from human subjects according to the methods described herein. The samples were previously categorized into two groups: subjects who were responsive to a stated therapy and subjects who were not responsive to the therapy.

The immune-oncology profile was used to understand differences across two groups of samples based on single or a combination of analytes used as predictive biomarker(s). Specifically, the immune-oncology profile analyte information was used to train a machine learning algorithm for classifying samples into the two groups.

The machine learning algorithm was used to generate classifiers based on individual analytes and multiple analytes. Single analyte biomarkers were used to solve for a threshold that maximizes the sensitivity and sensitivity simultaneously. With a large enough (normal) distribution of samples, this criteria may maximize the accuracy. Based on the small sample set (~10 in each group), which is typical in many studies such as early phase clinical trials, this optimization metric best approximates where the maximal accuracy may be if more samples were available.

Multi analyte biomarkers were found by optimizing the same statistics. Instead of using a linear threshold for single analytes, a random forest model was optimized to maximize the above predictive statistics. The algorithms chose the random forest model with the best set of individual analytes and the best set of hyper-parameters (e.g., the tuning knobs of the random forest technique).

Figure 12A:
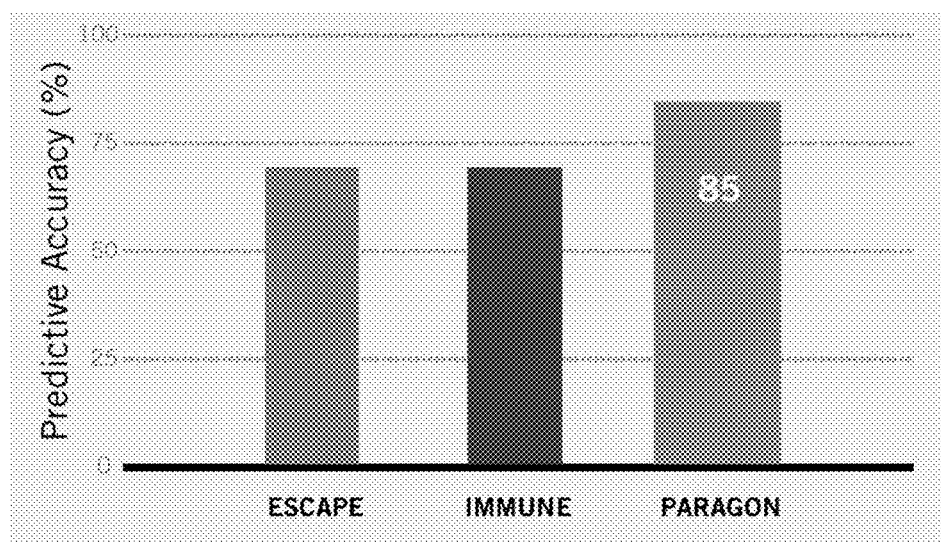
FIG. 12A shows a bar plot indicating the predictive accuracy of an "escape" biomarker, an "immune" biomarker, and a multi-analyte "paragon" classifier.

The predictive accuracies calculated for the most predictive escape gene ("escape") and the most predictive immune cell type ("immune"). Also shown is the predictive accuracy of using one or more analytes in the Paragon Assay ('PARAGON"). This "marker" is created by learning a machine learning model that incorporates information from one or more analytes. These results are shown in the predictive accuracy bar plot in FIG. 12A. The "escape" biomarker and "immune" biomarker both generated a predictive accuracy of just under 75%. Meanwhile, the "paragon" multi-analyte classifier resulted in an 85% predictive accuracy, demonstrating how the multi-analyte approach produced superior accuracy in the context of small sample sizes.

Figure 12B:
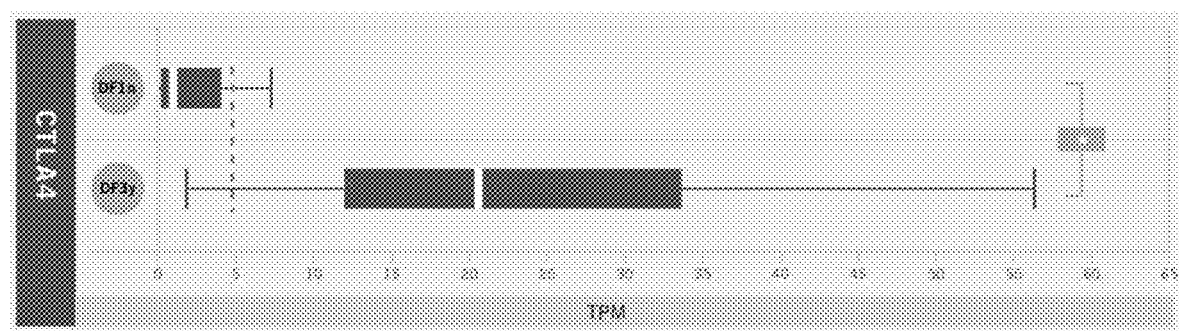
FIG. 12B shows box-and-whisker plots that visualize the statistics for groups of samples for the most predictive "escape" biomarker.

FIG. 12B shows box-and-whisker plots that visualize the statistics for groups of samples for the 2 most predictive analytes. The left and right sides of the box indicate the 1st and 3rd quartiles of the respective data set. The median is indicated by the white line inside the box. The minimum and maximum inlier data points are denoted by the ends of the whiskers, while outliers are shown as empty circles. The optimal threshold for a given analyte is shown as a vertical dotted line. Wilcoxon rank-sum testing is used to test the null hypothesis that the two groups are sampled from the same distribution. Significance of rejecting this hypothesis is denoted for p-values of <0.05, <0.01, and <0.001 by 1, 2, and 3 stars, respectively.

Figure 12C:
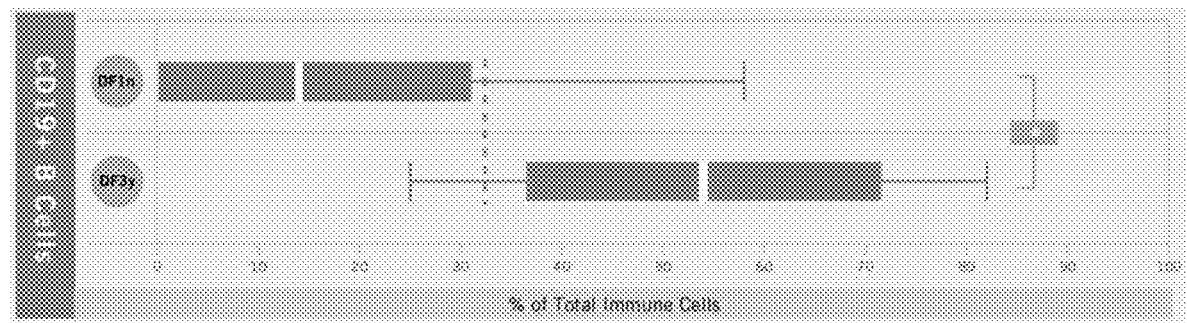
FIG. 12C shows box-and-whisker plots that visualize the statistics for groups of samples for the most predictive "immune" biomarker.
Figure 13:
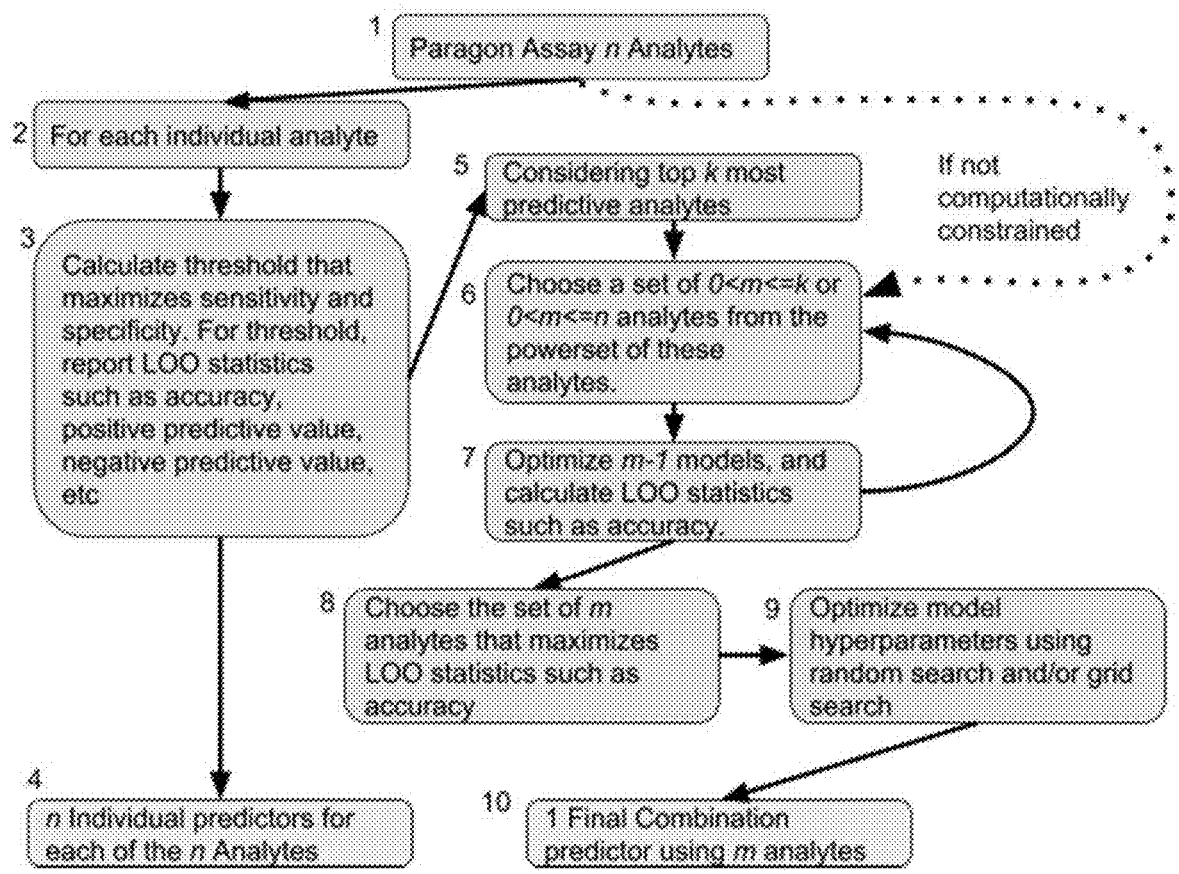
FIG. 13 depicts an example flow chart illustrating methods of generating single-analyte and multi-analyte classifiers as described in Example 7.

In this case, the "escape" biomarker identified as being the most predictive of the list of 10 immune-inhibitory genes assessed by the algorithm was CTLA4, which produced the just below 75% predictive accuracy when used to group a sample based on a threshold CTLA4 expression level. As shown in FIG. 12B, the dotted line indicates a threshold value of about 5 TPM (transcripts per kilobase million) separating the two groups or categories of samples. Likewise, the cell type identified as the most predictive "immune" biomarker was CD19+ B cells. As shown in FIG. 12C, a threshold value just above 30% separates the two sample categories. A flow chart illustrating the generation of a single-analyte classifier and a multi-analyte classifier is shown in FIG. 13. In single-analyte/biomarker analysis, the individual analyte is assessed by determining the threshold that maximizes sensitivity and specificity (steps 1-4 in FIG. 13). Separate predictors or classifiers are generated for each analyte. In multi-analyte analysis, the most predictive analytes are combined to generate a combination predictor or classifier based on multiple analytes (e.g., multiple immune escape gene(s) and/or immune cell(s) percentages infiltrating the tumor sample) (steps 5-10).

The statistical performance of these models was tested using the leave-one-out cross validation to calculate the accuracy, positive predictive value (ppv), and negative predictive value (npv) for each analyte. For a dataset limited in size, leave-one-out cross validation gives the best approximation to how an estimator will generalize to future, independent samples. The process works by iterating n times (where there are n data points), each time learning a threshold considering n−1 points and testing the prediction of the nth, left out, point. Then, all n predictions were considered to calculate prediction statistics. Thresholds were determined by optimizing equally for sensitivity and specificity using all samples. For data points that are normally distributed, this threshold may be the same threshold optimized for accuracy. The results of the statistical assessment of the model and/or analyte performance are shown below in Table 10.

TABLE 10

| Analyte | ppv (%) | DF1n Median (TPM) | DF3y Median (TPM) | npv (%) | accuracy (%) | threshold (TPM) | p-value |
|---|---|---|---|---|---|---|---|
| CTLA4 | 71.42 | 0.97 | 20.59 | 66.66 | 69.23 | 4.78 | 0.0151 |
| OX40 | 71.42 | 3.65 | 7.79 | 66.66 | 69.23 | 5.56 | 0.0864 |
| PD-1 | 66.66 | 1.12 | 2.52 | 57.14 | 61.53 | 1.35 | 0.253 |
| IDO1 | 57.14 | 7.22 | 3.13 | 50 | 53.84 | 5.46 | 0.475 |
| CD47 | 57.14 | 71.77 | 51.14 | 50 | 53.84 | 65 | 0.475 |
| PD-L1 | 57.14 | 3.64 | 3.89 | 50 | 53.84 | 3.77 | 0.475 |
| TIM-3 | 57.14 | 15.8 | 13.83 | 50 | 53.84 | 13.71 | 0.5677 |
| BTLA | 57.14 | 0.29 | 0.28 | 50 | 53.84 | 0.33 | 0.775 |
| ICOS | 57.14 | 2.23 | 1.56 | 50 | 53.84 | 1.58 | 0.8303 |
| ARG1 | 57.14 | 12.23 | 17.78 | 50 | 53.84 | 14.57 | 0.8864 |
| M2 Macrophages | 71.42 | 16.5 | 2 | 66.66 | 69.23 | 11.11 | 0.0455 |
| CD19+ B Cells | 71.42 | 14 | 54 | 66.66 | 69.23 | 32.39 | 0.0455 |
| CD14+ Monocytes | 71.42 | 39.5 | 12 | 66.66 | 69.23 | 28.87 | 0.2246 |
| CD56+ NK Cells | 80 | 0 | 7 | 62.5 | 69.23 | 0 | 0.3531 |
| CD+ T Cells | 100 | 0 | 0 | 54.54 | 61.53 | 0 | 0.3913 |
| Treg Cells | 100 | 0 | 0 | 50 | 53.84 | 0 | 0.6682 |
| CD4+ T Cells | 57.14 | 5.5 | 7 | 50 | 53.84 | 7.24 | 0.7209 |
| M1 Macrophages | 50 | 3.5 | 3 | 42.85 | 46.15 | 3.01 | 0.775 |
| Paragon | 100 | N/A | N/A | 75 | 84.61 | N/A | N/A |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method for treating a subject having or suspected of having cancer, comprising:
   (a) obtaining gene expression data comprising (i) a first data set corresponding to an expression level of at least one immune modulatory gene of said subject, said at least one immune modulatory gene comprising CTLA4, OX40, PD-1, IDO1, CD47, PD-L1, TIM-3, BTLA, ICOS, ARG1, or any combination thereof, and (ii) a second data set corresponding to expression levels of a plurality of expression signature genes from a biological sample of said subject;
   (b) using a deconvolution algorithm to process said second data set corresponding to said expression levels of said plurality of expression signature genes to output data identifying and quantifying a percentage of at least one cell type that is present in said biological sample, said at least one cell type comprising an immune cell type;
   (c) computer processing said first data set and said second data set to analyze said expression level of said at least one immune modulatory gene and said percentage of said at least one cell type from (b) to output a determination that said subject will be responsive or nonresponsive to an immunotherapy, wherein said determination indicates that said subject will be responsive to said immunotherapy; and
   (d) administering said immunotherapy to said subject based at least upon said determination that said subject will be responsive to said immunotherapy.

2. The method of claim 1, wherein the immune cell type comprises M1 macrophages, M2 macrophages, CD19+ B cells, CD14+ monocytes, CD56+ NK cells, CD8+ T cells, Treg cells, or CD4+ T cells.

3. The method of claim 1, wherein the computer processing of said first data set and said second data set in (c) is performed using a random forest machine learning algorithm or model.

4. The method of claim 1, wherein the deconvolution algorithm in (b) applies a deconvolution matrix to process said expression levels of said plurality of expression signature genes to identify and quantify the percentage of the at least one cell type.

5. The method of claim 4, wherein the deconvolution matrix comprises a plurality of immune cell expression signature genes.

6. The method of claim 4, wherein the deconvolution matrix comprises a plurality of tumor cell expression signature genes.

7. The method of claim 4, wherein the deconvolution matrix comprises a plurality of cell types, each cell type comprising a plurality of expression signature genes, wherein expression count for each expression signature gene is normalized across the plurality of cell types.

8. The method of claim 1, wherein the deconvolution algorithm processes said expression levels of said plurality of expression signature genes using linear least-squares regression (LLSR), quadratic programming (QP), perturbation model for gene expression deconvolution (PERT), robust linear regression (RLR), microarray microdissection with analysis of differences (MMAD), digital sorting algorithm (DSA), or support vector regression.

9. The method of claim 8, wherein the deconvolution algorithm performs an RNA normalization step to compensate for variation in RNA quantity amongst the at least one cell type in order to improve accuracy of the percentage of the at least one cell type.

10. The method of claim 9, wherein the deconvolution algorithm is a machine learning algorithm trained using comparison data comprising an actual percentage of the at least one cell type.

11. The method of claim 1, further comprising obtaining the gene expression data from the biological sample using next generation ribonucleic acid sequencing.

12. The method of claim 1, further comprising processing the gene expression data to determine mutational burden for the biological sample and inputting the mutational burden into a machine learning algorithm for analysis in order to enhance classification of the biological sample.

13. The method of claim 1, wherein the computer processing of said first data set and said second data set is performed using a machine learning algorithm that provides said determination with an accuracy of at least 85%.

* * * * *